US012806249B2

(12) United States Patent
Li et al.

(10) Patent No.: US 12,806,249 B2
(45) Date of Patent: Nov. 24, 2026

(54) HUMAN AMYLIN ANALOG, AND DERIVATIVE THEREOF AND USE THEREOF

(71) Applicants: Hangzhou Sciwind Biosciences Co., Ltd., Hangzhou (CN); Sciwind Biosciences (Beijing) Co., Ltd., Beijing (CN)

(72) Inventors: Yan Li, Beijing (CN); Hai Pan, Beijing (CN); Sujuan Hao, Beijing (CN); Zhaoying Li, Beijing (CN); Biao Li, Beijing (CN); Haixia Zou, Beijing (CN); Xinle Wu, Beijing (CN)

(73) Assignees: Hangzhou Sciwind Biosciences Co., Ltd., Hangzhou (CN); Sciwind Biosciences (Beijing) Co., Ltd., Beijing (CN)

( * ) Notice: Subject to any disclaimer, the term of this patent is extended or adjusted under 35 U.S.C. 154(b) by 0 days.

(21) Appl. No.: 19/387,401

(22) Filed: Nov. 12, 2025

(65) Prior Publication Data

US 2026/0166128 A1 Jun. 18, 2026

Related U.S. Application Data

(63) Continuation of application No. 18/869,726, filed as application No. PCT/CN2023/096811 on May 29, 2023.

(30) Foreign Application Priority Data

May 27, 2022 (CN) ........................ 202210588910.0

(51) Int. Cl.

| | |
|---|---|
| ***A61K 38/22*** | (2006.01) |
| ***A61K 9/20*** | (2006.01) |
| ***A61K 45/06*** | (2006.01) |
| ***A61K 47/54*** | (2017.01) |
| ***A61P 3/04*** | (2006.01) |
| ***C07K 14/575*** | (2006.01) |

(52) U.S. Cl.

CPC ............ *A61K 38/22* (2013.01); *A61K 9/2013* (2013.01); *A61K 45/06* (2013.01); *A61K 47/542* (2017.08); *A61P 3/04* (2018.01); *C07K 14/575* (2013.01)

(58) Field of Classification Search

None

See application file for complete search history.

(56) References Cited

U.S. PATENT DOCUMENTS

| | | | |
|---|---|---|---|
| 8,575,090 | B2 | 11/2013 | Schaeffer et al. |
| 8,895,504 | B2 | 11/2014 | Kruse et al. |
| 9,193,776 | B2 | 11/2015 | Soares |
| 10,174,082 | B2 | 1/2019 | Kruse et al. |
| 10,766,940 | B2 | 9/2020 | Jhamandas et al. |
| 11,390,654 | B2 | 7/2022 | Soares |
| 11,541,123 | B2 | 1/2023 | Coskun et al. |
| 2016/0272693 | A1 | 9/2016 | Just et al. |
| 2018/0071366 | A1 | 3/2018 | Mathiesen et al. |
| 2020/0115430 | A1 | 4/2020 | Blackwell et al. |
| 2022/0204580 | A1 | 6/2022 | Bednarek et al. |
| 2023/0061959 | A1 | 3/2023 | Adocia |
| 2023/0331803 | A1 | 10/2023 | Kruse et al. |
| 2026/0115256 | A1 | 4/2026 | Li et al. |

FOREIGN PATENT DOCUMENTS

| | | | |
|---|---|---|---|
| CN | 101413009 | A | 4/2009 |
| CN | 103596972 | A | 2/2014 |
| CN | 107699588 | A | 2/2018 |
| CN | 109485720 | A | 3/2019 |
| CN | 111171134 | A | 5/2020 |
| CN | 112661663 | B | 9/2021 |
| CN | 113621045 | A | 11/2021 |
| CN | 114249808 | A | 3/2022 |
| CN | 115947822 | A | 4/2023 |
| CN | 116327890 | A | 6/2023 |
| EP | 4148064 | A1 | 3/2023 |
| WO | WO-2008028859 | A1 | 3/2008 |
| WO | WO-2011064282 | A1 | 6/2011 |
| WO | WO-2012162542 | A1 | 11/2012 |
| WO | WO-2015040182 | A2 | 3/2015 |
| WO | WO-2019170895 | A1 | 9/2019 |
| WO | WO-2020023386 | A1 | 1/2020 |

(Continued)

OTHER PUBLICATIONS

Rejili et al. (2026). Vascular Pharmacology. 162:107563; 16 pages.*

Co-pending U.S. Appl. No. 18/869,726, inventors Yan; Li et al., filed Nov. 26, 2024.

EA202493121 Office Action dated May 12, 2025, and an English translation.

Mccartney, Fiona, et al. Labrasol is an efficacious intestinal permeation enhancer across rat intestine: ex vivo and in vivo rat studies. Journal of Controlled Release 310: 115-126. (2019).

(Continued)

*Primary Examiner* — Christine J Saoud
*Assistant Examiner* — Jon M Lockard
(74) *Attorney, Agent, or Firm* — WILSON SONSINI GOODRICH & ROSATI

(57) ABSTRACT

The present disclosure relates to a polypeptide analog or a derivative thereof, and a preparation method and use thereof, and particularly to an agonistic polypeptide analog or a derivative thereof of an insulin amyloid polypeptide receptor. The polypeptide analog or the derivative thereof provided by the present disclosure has good agonistic activity on the insulin amyloid polypeptide receptor, has the characteristics of good stability, high activity, etc. at the same time, and can be used for treating and preventing diseases related to the insulin amyloid polypeptide receptor, such as body weight abnormality, especially obesity and overweight.

7 Claims, 7 Drawing Sheets

Specification includes a Sequence Listing.

(56) References Cited

FOREIGN PATENT DOCUMENTS

| | | | |
|---|---|---|---|
| WO | WO-2022129526 | A1 | 6/2022 |
| WO | WO-2023288313 | A1 | 1/2023 |
| WO | WO-2023028466 | A1 | 3/2023 |
| WO | WO-2023227133 | A1 | 11/2023 |
| WO | WO-2024022465 | A1 | 2/2024 |
| WO | WO-2024164776 | A1 | 8/2024 |
| WO | WO-2024208277 | A1 | 10/2024 |
| WO | WO-2024245233 | A1 | 12/2024 |

OTHER PUBLICATIONS

PCT/CN2023/096811 International Preliminary Report on Patentability dated Dec. 12, 2024.

PCT/CN2023/096811 International Search Report and Written Opinion dated Jul. 28, 2023.

PCT/CN2024/095763 International Search Report and Written Opinion dated Aug. 16, 2024.

Sambrook, et al. Molecular Cloning: A Laboratory Manual. 2nd Edition, 1989.

Uhl, Philipp, et al. Coating of PLA-nanoparticles with cyclic, arginine-rich cell penetrating peptides enables oral delivery of liraglutide. Nanomedicine: Nanotechnology, Biology and Medicine 24: 102132. (2020).

Vivek, Gupta. et al. Mucoadhesive intestinal devices for oral delivery of salmon calcitonin. Journal of Controlled Release. (172)3:753-762. (2013).

Yan, Li-Mei. et al. Design of a mimic of nonamyloidogenic and bioactive human islet amyloid polypeptide (IAPP) as nanomolar affinity inhibitor of IAPP cytotoxic fibrillogenesis. Proceedings of the National Academy of Sciences of the United States of America 103(7):2046-2051 (2006).

Co-Pending U.S. Appl. No. 19/387,401; Inventors Yan Li, et al, filed Nov. 12, 2025.

Co-pending U.S. Appl. No. 19/387,401, inventors Li; Yan et al., filed Nov. 12, 2025.

EA202593077 Office Action dated Jan. 28, 2026, and a partial English translation.

EP Serial No. 23811203.1 Partial Supplementary Search Report dated Apr. 30, 2026.

Kruse, Thomas. et al. Development of Cagrilintide, a Long-Acting Amylin Analogue. Journal of medicinal chemistry 64(15):11183-11194 (2021).

* cited by examiner

SEQUENCE LISTING

```
Sequence total quantity: 310
SEQ ID NO: 1             moltype = AA  length = 37
FEATURE                  Location/Qualifiers
source                   1..37
                         mol_type = protein
                         organism = synthetic construct
SEQUENCE: 1
KCNTATCATQ RLAEFLRHSS NNFGPILPPT NVGSNTP                        37

SEQ ID NO: 2             moltype = AA  length = 37
FEATURE                  Location/Qualifiers
source                   1..37
                         mol_type = protein
                         organism = synthetic construct
SITE                     37
                         note = (2S,4R)-4-hydroxypyrrolidine-2-carboxamide
SEQUENCE: 2
KCNTATCATQ RLADFLRHSS NNLGPILPPT NVGSNTX                        37

SEQ ID NO: 3             moltype = AA  length = 37
FEATURE                  Location/Qualifiers
source                   1..37
                         mol_type = protein
                         organism = synthetic construct
SITE                     37
                         note = (2S,4R)-4-hydroxypyrrolidine-2-carboxamide
SEQUENCE: 3
KCNTATCATQ RLADFLRHSS NNLKPILPPT NVGSNTX                        37

SEQ ID NO: 4             moltype = AA  length = 37
FEATURE                  Location/Qualifiers
source                   1..37
                         mol_type = protein
                         organism = synthetic construct
SITE                     37
                         note = (2S,4R)-4-hydroxypyrrolidine-2-carboxamide
SEQUENCE: 4
RCNTATCATQ RLADFLRHSK NNLGPILPPT NVGSNTX                        37

SEQ ID NO: 5             moltype = AA  length = 37
FEATURE                  Location/Qualifiers
source                   1..37
                         mol_type = protein
                         organism = synthetic construct
SEQUENCE: 5
RCNTATCATQ RLAEFLRHSS KNLGPILPPT NVGSNTP                        37

SEQ ID NO: 6             moltype = AA  length = 37
FEATURE                  Location/Qualifiers
source                   1..37
                         mol_type = protein
```

```
                         organism = synthetic construct
SEQUENCE: 6
RCNTATCATQ RLAEFLRHSS NKLGPILPPT NVGSNTP                     37

SEQ ID NO: 7             moltype = AA  length = 37
FEATURE                  Location/Qualifiers
source                   1..37
                         mol_type = protein
                         organism = synthetic construct
SEQUENCE: 7
RCNTATCATQ RLAEFLRHSS NNKGPILPPT NVGSNTP                     37

SEQ ID NO: 8             moltype = AA  length = 37
FEATURE                  Location/Qualifiers
source                   1..37
                         mol_type = protein
                         organism = synthetic construct
SEQUENCE: 8
RCNTATCATQ RLAEFLRHSS NNLKPILPPT NVGSNTP                     37

SEQ ID NO: 9             moltype = AA  length = 37
FEATURE                  Location/Qualifiers
source                   1..37
                         mol_type = protein
                         organism = synthetic construct
SEQUENCE: 9
RCNTATCATQ RLAEFLRHSS NNLGKILPPT NVGSNTP                     37

SEQ ID NO: 10            moltype = AA  length = 37
FEATURE                  Location/Qualifiers
source                   1..37
                         mol_type = protein
                         organism = synthetic construct
SEQUENCE: 10
RCNTATCATQ RLAEFLRHSS NNLKPILSST NVGSNTP                     37

SEQ ID NO: 11            moltype = AA  length = 37
FEATURE                  Location/Qualifiers
source                   1..37
                         mol_type = protein
                         organism = synthetic construct
SEQUENCE: 11
RCNTATCATQ RLAEFLRHSS NNLKAILPST NVGSNTP                     37

SEQ ID NO: 12            moltype = AA  length = 37
FEATURE                  Location/Qualifiers
source                   1..37
                         mol_type = protein
                         organism = synthetic construct
SEQUENCE: 12
RCNTATCATQ RLAEFLRHSS NNLKAILSPT NVGSNTP                     37

SEQ ID NO: 13            moltype = AA  length = 37
FEATURE                  Location/Qualifiers
source                   1..37
                         mol_type = protein
                         organism = synthetic construct
SEQUENCE: 13
RCNTATCATQ RLAEFLRHSS NNLKPILPST NVGSNTP                     37

SEQ ID NO: 14            moltype = AA  length = 37
FEATURE                  Location/Qualifiers
source                   1..37
                         mol_type = protein
                         organism = synthetic construct
SEQUENCE: 14
RCNTATCATQ RLAEFLRHSS NNLKPILSPT NVGSNTP                     37

SEQ ID NO: 15            moltype = AA  length = 37
FEATURE                  Location/Qualifiers
source                   1..37
                         mol_type = protein
                         organism = synthetic construct
SEQUENCE: 15
RCNTATCATQ RLAEFLRHSS NNLKAILPPT NVGSNTP                     37

SEQ ID NO: 16            moltype = AA  length = 37
FEATURE                  Location/Qualifiers
source                   1..37
```

```
                         mol_type = protein
                         organism = synthetic construct
SEQUENCE: 16
RCNTATCATQ RLAEFLRHSS NNLKPILPPT NVGSNTY                          37

SEQ ID NO: 17            moltype = AA  length = 37
FEATURE                  Location/Qualifiers
source                   1..37
                         mol_type = protein
                         organism = synthetic construct
SEQUENCE: 17
RCNTATCATQ RLAEFLRHSS NNLKAILSST NVGSNTY                          37

SEQ ID NO: 18            moltype = AA  length = 37
FEATURE                  Location/Qualifiers
source                   1..37
                         mol_type = protein
                         organism = synthetic construct
SEQUENCE: 18
RCNTATCATQ RLAEFLRHSS NNLKPILSST NVGSNTY                          37

SEQ ID NO: 19            moltype = AA  length = 37
FEATURE                  Location/Qualifiers
source                   1..37
                         mol_type = protein
                         organism = synthetic construct
SEQUENCE: 19
RCNTATCATQ RLAEFLRHSS NNLKAILPST NVGSNTY                          37

SEQ ID NO: 20            moltype = AA  length = 37
FEATURE                  Location/Qualifiers
source                   1..37
                         mol_type = protein
                         organism = synthetic construct
SEQUENCE: 20
RCNTATCATQ RLAEFLRHSS NNLKAILSPT NVGSNTY                          37

SEQ ID NO: 21            moltype = AA  length = 37
FEATURE                  Location/Qualifiers
source                   1..37
                         mol_type = protein
                         organism = synthetic construct
SEQUENCE: 21
RCNTATCATQ RLAEFLRHSS NNLKPILPST NVGSNTY                          37

SEQ ID NO: 22            moltype = AA  length = 37
FEATURE                  Location/Qualifiers
source                   1..37
                         mol_type = protein
                         organism = synthetic construct
SEQUENCE: 22
RCNTATCATQ RLAEFLRHSS NNLKPILSPT NVGSNTY                          37

SEQ ID NO: 23            moltype = AA  length = 37
FEATURE                  Location/Qualifiers
source                   1..37
                         mol_type = protein
                         organism = synthetic construct
SEQUENCE: 23
RCNTATCATQ RLAEFLRHSS NNLKAILPPT NVGSNTY                          37

SEQ ID NO: 24            moltype = AA  length = 37
FEATURE                  Location/Qualifiers
source                   1..37
                         mol_type = protein
                         organism = synthetic construct
SEQUENCE: 24
RCNTATCATQ RLAEFLRHSS NNLKPILPPT NVGSGTP                          37

SEQ ID NO: 25            moltype = AA  length = 37
FEATURE                  Location/Qualifiers
source                   1..37
                         mol_type = protein
                         organism = synthetic construct
SEQUENCE: 25
RCNTATCATQ RLAEFLRHSS NNLKAILSST NVGSGTP                          37

SEQ ID NO: 26            moltype = AA  length = 37
FEATURE                  Location/Qualifiers
```

```
source                  1..37
                        mol_type = protein
                        organism = synthetic construct
SEQUENCE: 26
RCNTATCATQ RLAEFLRHSS NNLKPILSST NVGSGTP                            37

SEQ ID NO: 27           moltype = AA  length = 37
FEATURE                 Location/Qualifiers
source                  1..37
                        mol_type = protein
                        organism = synthetic construct
SEQUENCE: 27
RCNTATCATQ RLAEFLRHSS NNLKAILPST NVGSGTP                            37

SEQ ID NO: 28           moltype = AA  length = 37
FEATURE                 Location/Qualifiers
source                  1..37
                        mol_type = protein
                        organism = synthetic construct
SEQUENCE: 28
RCNTATCATQ RLAEFLRHSS NNLKAILSPT NVGSGTP                            37

SEQ ID NO: 29           moltype = AA  length = 37
FEATURE                 Location/Qualifiers
source                  1..37
                        mol_type = protein
                        organism = synthetic construct
SEQUENCE: 29
RCNTATCATQ RLAEFLRHSS NNLKPILPST NVGSGTP                            37

SEQ ID NO: 30           moltype = AA  length = 37
FEATURE                 Location/Qualifiers
source                  1..37
                        mol_type = protein
                        organism = synthetic construct
SEQUENCE: 30
RCNTATCATQ RLAEFLRHSS NNLKPILSPT NVGSGTP                            37

SEQ ID NO: 31           moltype = AA  length = 37
FEATURE                 Location/Qualifiers
source                  1..37
                        mol_type = protein
                        organism = synthetic construct
SEQUENCE: 31
RCNTATCATQ RLAEFLRHSS NNLKAILPPT NVGSGTP                            37

SEQ ID NO: 32           moltype = AA  length = 37
FEATURE                 Location/Qualifiers
source                  1..37
                        mol_type = protein
                        organism = synthetic construct
SEQUENCE: 32
KCNTATCATQ RLAEFLRHSS NNLKPILPPT NVGSNTP                            37

SEQ ID NO: 33           moltype = AA  length = 37
FEATURE                 Location/Qualifiers
source                  1..37
                        mol_type = protein
                        organism = synthetic construct
SEQUENCE: 33
KCNTATCATQ RLAEFLRHSS NNLKPILSST NVGSNTP                            37

SEQ ID NO: 34           moltype = AA  length = 37
FEATURE                 Location/Qualifiers
source                  1..37
                        mol_type = protein
                        organism = synthetic construct
SEQUENCE: 34
KCNTATCATQ RLAEFLRHSS NNLKAILPST NVGSNTP                            37

SEQ ID NO: 35           moltype = AA  length = 37
FEATURE                 Location/Qualifiers
source                  1..37
                        mol_type = protein
                        organism = synthetic construct
SEQUENCE: 35
KCNTATCATQ RLAEFLRHSS NNLKAILSPT NVGSNTP                            37

SEQ ID NO: 36           moltype = AA  length = 37
```

-continued

```
FEATURE                Location/Qualifiers
source                 1..37
                       mol_type = protein
                       organism = synthetic construct
SEQUENCE: 36
KCNTATCATQ RLAEFLRHSS NNLKPILPST NVGSNTP                      37

SEQ ID NO: 37          moltype = AA  length = 37
FEATURE                Location/Qualifiers
source                 1..37
                       mol_type = protein
                       organism = synthetic construct
SEQUENCE: 37
KCNTATCATQ RLAEFLRHSS NNLKPILSPT NVGSNTP                      37

SEQ ID NO: 38          moltype = AA  length = 37
FEATURE                Location/Qualifiers
source                 1..37
                       mol_type = protein
                       organism = synthetic construct
SEQUENCE: 38
KCNTATCATQ RLAEFLRHSS NNLKAILPPT NVGSNTP                      37

SEQ ID NO: 39          moltype = AA  length = 37
FEATURE                Location/Qualifiers
source                 1..37
                       mol_type = protein
                       organism = synthetic construct
SITE                   37
                       note = (2S,4R)-4-hydroxypyrrolidine-2-carboxamide
SEQUENCE: 39
RCNTATCATQ RLAEFLRHSS NNLKPILPPT NVGSNTX                      37

SEQ ID NO: 40          moltype = AA  length = 37
FEATURE                Location/Qualifiers
source                 1..37
                       mol_type = protein
                       organism = synthetic construct
SITE                   37
                       note = (2S,4R)-4-hydroxypyrrolidine-2-carboxamide
SEQUENCE: 40
RCNTATCATQ RLAEFLRHSS NNLKPILPPT NVGSGTX                      37

SEQ ID NO: 41          moltype = AA  length = 37
FEATURE                Location/Qualifiers
source                 1..37
                       mol_type = protein
                       organism = synthetic construct
SEQUENCE: 41
RCNTATCATQ RLADFLRHSS NNLKPILPPT NVGSNTP                      37

SEQ ID NO: 42          moltype = AA  length = 37
FEATURE                Location/Qualifiers
source                 1..37
                       mol_type = protein
                       organism = synthetic construct
SITE                   14
                       note = (S)-2-aminohexanedioic acid
SEQUENCE: 42
RCNTATCATQ RLAXFLRHSS NNLKPILPPT NVGSNTP                      37

SEQ ID NO: 43          moltype = AA  length = 37
FEATURE                Location/Qualifiers
source                 1..37
                       mol_type = protein
                       organism = synthetic construct
SITE                   14
                       note = (S)-2,4-diaminobutanoic acid
SEQUENCE: 43
RCNTATCATQ RLAXFLRHSS NNLKPILPPT NVGSNTP                      37

SEQ ID NO: 44          moltype = AA  length = 37
FEATURE                Location/Qualifiers
source                 1..37
                       mol_type = protein
                       organism = synthetic construct
SITE                   14
                       note = (S)-2,3-diaminopropanoic acid
SEQUENCE: 44
```

-continued

```
RCNTATCATQ RLAXFLRHSS NNLKPILPPT NVGSNTP                    37

SEQ ID NO: 45          moltype = AA  length = 37
FEATURE                Location/Qualifiers
source                 1..37
                       mol_type = protein
                       organism = synthetic construct
SITE                   17
                       note = (S)-2,5-diaminopentanoic acid
SEQUENCE: 45
RCNTATCATQ RLAEFLXHSS NNLKPILPPT NVGSNTP                    37

SEQ ID NO: 46          moltype = AA  length = 37
FEATURE                Location/Qualifiers
source                 1..37
                       mol_type = protein
                       organism = synthetic construct
SEQUENCE: 46
RCNTATCATQ RLAEFLRHSS NNLKPILPPT NVGSNTP                    37

SEQ ID NO: 47          moltype = AA  length = 37
FEATURE                Location/Qualifiers
source                 1..37
                       mol_type = protein
                       organism = synthetic construct
SEQUENCE: 47
RCNTATCATQ RLADFLRHSS NNLKPILPPT NVGSNTP                    37

SEQ ID NO: 48          moltype = AA  length = 36
FEATURE                Location/Qualifiers
source                 1..36
                       mol_type = protein
                       organism = synthetic construct
SEQUENCE: 48
CNTATCATQR LAEFLRHSSN NLKPILPPTN VGSNTP                     36

SEQ ID NO: 49          moltype = AA  length = 36
FEATURE                Location/Qualifiers
source                 1..36
                       mol_type = protein
                       organism = synthetic construct
SEQUENCE: 49
CNTATCATQR LADFLRHSSN NLKPILPPTN VGSNTP                     36

SEQ ID NO: 50          moltype = AA  length = 37
FEATURE                Location/Qualifiers
source                 1..37
                       mol_type = protein
                       organism = synthetic construct
SITE                   37
                       note = (2S,4R)-4-hydroxypyrrolidine-2-carboxamide
SEQUENCE: 50
RCNTATCATQ RLADFLRHSS NNLKPILPPT NVGSNTX                    37

SEQ ID NO: 51          moltype = AA  length = 36
FEATURE                Location/Qualifiers
source                 1..36
                       mol_type = protein
                       organism = synthetic construct
SITE                   36
                       note = (2S,4R)-4-hydroxypyrrolidine-2-carboxamide
SEQUENCE: 51
CNTATCATQR LAEFLRHSSN NLKPILPPTN VGSNTX                     36

SEQ ID NO: 52          moltype = AA  length = 36
FEATURE                Location/Qualifiers
source                 1..36
                       mol_type = protein
                       organism = synthetic construct
SITE                   36
                       note = (2S,4R)-4-hydroxypyrrolidine-2-carboxamide
SEQUENCE: 52
CNTATCATQR LADFLRHSSN NLKPILPPTN VGSNTX                     36

SEQ ID NO: 53          moltype = AA  length = 37
FEATURE                Location/Qualifiers
source                 1..37
                       mol_type = protein
                       organism = synthetic construct
```

```
SITE                    37
                        note = (2S,4S)-4-hydroxypyrrolidine-2-carboxamide
SEQUENCE: 53
RCNTATCATQ RLAEFLRHSS NNLKPILPPT NVGSNTX                            37

SEQ ID NO: 54           moltype = AA  length = 37
FEATURE                 Location/Qualifiers
source                  1..37
                        mol_type = protein
                        organism = synthetic construct
SITE                    37
                        note = (2S,4S)-4-hydroxypyrrolidine-2-carboxamide
SEQUENCE: 54
RCNTATCATQ RLADFLRHSS NNLKPILPPT NVGSNTX                            37

SEQ ID NO: 55           moltype = AA  length = 37
FEATURE                 Location/Qualifiers
source                  1..37
                        mol_type = protein
                        organism = synthetic construct
SITE                    37
                        note = (S)-piperidine-2-carboxamide
SEQUENCE: 55
RCNTATCATQ RLAEFLRHSS NNLKPILPPT NVGSNTX                            37

SEQ ID NO: 56           moltype = AA  length = 37
FEATURE                 Location/Qualifiers
source                  1..37
                        mol_type = protein
                        organism = synthetic construct
SITE                    37
                        note = (S)-piperidine-2-carboxamide
SEQUENCE: 56
RCNTATCATQ RLADFLRHSS NNLKPILPPT NVGSNTX                            37

SEQ ID NO: 57           moltype = AA  length = 37
FEATURE                 Location/Qualifiers
source                  1..37
                        mol_type = protein
                        organism = synthetic construct
SITE                    37
                        note = (S)-azetidine-2-carboxamide
SEQUENCE: 57
RCNTATCATQ RLAEFLRHSS NNLKPILPPT NVGSNTX                            37

SEQ ID NO: 58           moltype = AA  length = 37
FEATURE                 Location/Qualifiers
source                  1..37
                        mol_type = protein
                        organism = synthetic construct
SITE                    37
                        note = (S)-azetidine-2-carboxamide
SEQUENCE: 58
RCNTATCATQ RLADFLRHSS NNLKPILPPT NVGSNTX                            37

SEQ ID NO: 59           moltype = AA  length = 37
FEATURE                 Location/Qualifiers
source                  1..37
                        mol_type = protein
                        organism = synthetic construct
SITE                    37
                        note = (2S)-3-aminopyrrolidine-2-carboxamide
SEQUENCE: 59
RCNTATCATQ RLAEFLRHSS NNLKPILPPT NVGSNTX                            37

SEQ ID NO: 60           moltype = AA  length = 37
FEATURE                 Location/Qualifiers
source                  1..37
                        mol_type = protein
                        organism = synthetic construct
SITE                    37
                        note = (2S)-3-aminopyrrolidine-2-carboxamide
SEQUENCE: 60
RCNTATCATQ RLADFLRHSS NNLKPILPPT NVGSNTX                            37

SEQ ID NO: 61           moltype = AA  length = 37
FEATURE                 Location/Qualifiers
source                  1..37
                        mol_type = protein
```

-continued

```
                       organism = synthetic construct
SITE                   37
                       note = (S)-2-methylpyrrolidine-2-carboxamide
SEQUENCE: 61
RCNTATCATQ RLAEFLRHSS NNLKPILPPT NVGSNTX                       37

SEQ ID NO: 62          moltype = AA  length = 37
FEATURE                Location/Qualifiers
source                 1..37
                       mol_type = protein
                       organism = synthetic construct
SITE                   37
                       note = (S)-2-methylpyrrolidine-2-carboxamide
SEQUENCE: 62
RCNTATCATQ RLADFLRHSS NNLKPILPPT NVGSNTX                       37

SEQ ID NO: 63          moltype = AA  length = 37
FEATURE                Location/Qualifiers
source                 1..37
                       mol_type = protein
                       organism = synthetic construct
SITE                   37
                       note = (2S,4R)-4-hydroxypyrrolidine-2-carboxamide
SEQUENCE: 63
KCNTATCATQ RLADFLRHSS NNFGPILPPT NVGSNTX                       37

SEQ ID NO: 64          moltype = AA  length = 37
FEATURE                Location/Qualifiers
source                 1..37
                       mol_type = protein
                       organism = synthetic construct
SITE                   1
                       note = (S)-2,3-diaminopropanoic acid
SITE                   37
                       note = (2S,4R)-4-hydroxypyrrolidine-2-carboxamide
SEQUENCE: 64
XCNTATCATQ RLADFLRHSS NNLKPILPPT NVGSNTX                       37

SEQ ID NO: 65          moltype = AA  length = 37
FEATURE                Location/Qualifiers
source                 1..37
                       mol_type = protein
                       organism = synthetic construct
SITE                   1
                       note = (S)-2,4-diaminobutanoic acid
SITE                   37
                       note = (2S,4R)-4-hydroxypyrrolidine-2-carboxamide
SEQUENCE: 65
XCNTATCATQ RLADFLRHSS NNLKPILPPT NVGSNTX                       37

SEQ ID NO: 66          moltype = AA  length = 37
FEATURE                Location/Qualifiers
source                 1..37
                       mol_type = protein
                       organism = synthetic construct
SITE                   1
                       note = (S)-2,5-diaminopentanoic acid
SITE                   37
                       note = (2S,4R)-4-hydroxypyrrolidine-2-carboxamide
SEQUENCE: 66
XCNTATCATQ RLADFLRHSS NNLKPILPPT NVGSNTX                       37

SEQ ID NO: 67          moltype = AA  length = 37
FEATURE                Location/Qualifiers
source                 1..37
                       mol_type = protein
                       organism = synthetic construct
SITE                   1
                       note = (2S)-2-amino-6-(diaminomethylideneamino)hexanoic acid
SITE                   37
                       note = (2S,4R)-4-hydroxypyrrolidine-2-carboxamide
SEQUENCE: 67
XCNTATCATQ RLADFLRHSS NNLKPILPPT NVGSNTX                       37

SEQ ID NO: 68          moltype = AA  length = 37
FEATURE                Location/Qualifiers
source                 1..37
                       mol_type = protein
                       organism = synthetic construct
```

```
SITE                    37
                        note = (2S,4R)-4-hydroxypyrrolidine-2-carboxamide
SEQUENCE: 68
HCNTATCATQ RLADFLRHSS NNLKPILPPT NVGSNTX                       37

SEQ ID NO: 69           moltype = AA  length = 37
FEATURE                 Location/Qualifiers
source                  1..37
                        mol_type = protein
                        organism = synthetic construct
SITE                    37
                        note = (2S,4R)-4-hydroxypyrrolidine-2-carboxamide
SEQUENCE: 69
DCNTATCATQ RLADFLRHSS NNLKPILPPT NVGSNTX                       37

SEQ ID NO: 70           moltype = AA  length = 37
FEATURE                 Location/Qualifiers
source                  1..37
                        mol_type = protein
                        organism = synthetic construct
SITE                    37
                        note = (2S,4R)-4-hydroxypyrrolidine-2-carboxamide
SEQUENCE: 70
ECNTATCATQ RLADFLRHSS NNLKPILPPT NVGSNTX                       37

SEQ ID NO: 71           moltype = AA  length = 37
FEATURE                 Location/Qualifiers
source                  1..37
                        mol_type = protein
                        organism = synthetic construct
SITE                    37
                        note = (2S,4R)-4-hydroxypyrrolidine-2-carboxamide
SEQUENCE: 71
RCNTATCATQ RLADFLRHSS NNKGPILPPT NVGSNTX                       37

SEQ ID NO: 72           moltype = AA  length = 37
FEATURE                 Location/Qualifiers
source                  1..37
                        mol_type = protein
                        organism = synthetic construct
SITE                    37
                        note = (2S,4R)-4-hydroxypyrrolidine-2-carboxamide
SEQUENCE: 72
RCNTATCATQ RLADFLRHSS NKLGPILPPT NVGSNTX                       37

SEQ ID NO: 73           moltype = AA  length = 37
FEATURE                 Location/Qualifiers
source                  1..37
                        mol_type = protein
                        organism = synthetic construct
SITE                    37
                        note = (2S,4R)-4-hydroxypyrrolidine-2-carboxamide
SEQUENCE: 73
RCNTATCATQ RLADFLRHSS KNLGPILPPT NVGSNTX                       37

SEQ ID NO: 74           moltype = AA  length = 37
FEATURE                 Location/Qualifiers
source                  1..37
                        mol_type = protein
                        organism = synthetic construct
SITE                    37
                        note = (2S,4R)-4-hydroxypyrrolidine-2-carboxamide
SEQUENCE: 74
RCNTATCATQ RLADFLRHKS NNLGPILPPT NVGSNTX                       37

SEQ ID NO: 75           moltype = AA  length = 37
FEATURE                 Location/Qualifiers
source                  1..37
                        mol_type = protein
                        organism = synthetic construct
SITE                    37
                        note = (2S,4R)-4-hydroxypyrrolidine-2-carboxamide
SEQUENCE: 75
RCNTATCATQ RLADFLRHSS NNLGKILPPT NVGSNTX                       37

SEQ ID NO: 76           moltype = AA  length = 37
FEATURE                 Location/Qualifiers
source                  1..37
                        mol_type = protein
```

-continued

```
                        organism = synthetic construct
SITE                    37
                        note = (2S,4R)-4-hydroxypyrrolidine-2-carboxamide
SEQUENCE: 76
RCNTATCATQ RLADFLRHSS NNLGPILPPT NVGSNTX                            37

SEQ ID NO: 77           moltype = AA  length = 37
FEATURE                 Location/Qualifiers
source                  1..37
                        mol_type = protein
                        organism = synthetic construct
SITE                    37
                        note = (2S,4R)-4-hydroxypyrrolidine-2-carboxamide
SEQUENCE: 77
HCNTATCATQ RLADFLRHSS NNLGPILPPT NVGSNTX                            37

SEQ ID NO: 78           moltype = AA  length = 37
FEATURE                 Location/Qualifiers
source                  1..37
                        mol_type = protein
                        organism = synthetic construct
SEQUENCE: 78
KCNTATCATQ RLANFLVHSS NNFGPILPPT NVGSNTY                            37

SEQ ID NO: 79           moltype = AA  length = 37
FEATURE                 Location/Qualifiers
source                  1..37
                        mol_type = protein
                        organism = synthetic construct
SITE                    37
                        note = (S)-azetidine-2-carboxamide
SEQUENCE: 79
KCNTATCATQ RLADFLRHSS NNLKPILPPT NVGSNTX                            37

SEQ ID NO: 80           moltype = AA  length = 37
FEATURE                 Location/Qualifiers
source                  1..37
                        mol_type = protein
                        organism = synthetic construct
SITE                    37
                        note = (S)-azetidine-2-carboxamide
SEQUENCE: 80
KCNTATCATQ RLADFLRHSS NNLKPILPPT NVGSNTX                            37

SEQ ID NO: 81           moltype = AA  length = 37
FEATURE                 Location/Qualifiers
source                  1..37
                        mol_type = protein
                        organism = synthetic construct
SEQUENCE: 81
KCNTATCATQ RLANFLVHSS NNFGPILPPT NVGSNTY                            37

SEQ ID NO: 82           moltype = AA  length = 37
FEATURE                 Location/Qualifiers
source                  1..37
                        mol_type = protein
                        organism = synthetic construct
SITE                    37
                        note = (S)-azetidine-2-carboxamide
SEQUENCE: 82
KCNTATCATQ RLADFLRHSS NNLKPILPPT NVGSNTX                            37

SEQ ID NO: 83           moltype = AA  length = 37
FEATURE                 Location/Qualifiers
source                  1..37
                        mol_type = protein
                        organism = synthetic construct
SITE                    37
                        note = (2S,4R)-4-hydroxypyrrolidine-2-carboxamide
SEQUENCE: 83
KCNTATCATQ RLADFLRHSS NNLRPILPPT NVGSNTX                            37

SEQ ID NO: 84           moltype = AA  length = 37
FEATURE                 Location/Qualifiers
source                  1..37
                        mol_type = protein
                        organism = synthetic construct
SITE                    37
                        note = (2S,4R)-4-hydroxypyrrolidine-2-carboxamide
```

```
SEQUENCE: 84
KCNTATCATQ RLADFLRHSS NNLHPILPPT NVGSNTX                         37

SEQ ID NO: 85           moltype = AA  length = 37
FEATURE                 Location/Qualifiers
source                  1..37
                        mol_type = protein
                        organism = synthetic construct
SEQUENCE: 85
KCNTATCATQ RLADFLRHSS NNLKPILPPT NVGSNTP                         37

SEQ ID NO: 86           moltype = AA  length = 37
FEATURE                 Location/Qualifiers
source                  1..37
                        mol_type = protein
                        organism = synthetic construct
SEQUENCE: 86
KCNTATCATQ RLADFLRHSS NNLRPILPPT NVGSNTP                         37

SEQ ID NO: 87           moltype = AA  length = 37
FEATURE                 Location/Qualifiers
source                  1..37
                        mol_type = protein
                        organism = synthetic construct
SEQUENCE: 87
KCNTATCATQ RLADFLRHSS NNLHPILPPT NVGSNTP                         37

SEQ ID NO: 88           moltype = AA  length = 37
FEATURE                 Location/Qualifiers
source                  1..37
                        mol_type = protein
                        organism = synthetic construct
SEQUENCE: 88
KCNTATCATQ RLADFLRHSS NNLPPILPPT NVGSNTP                         37

SEQ ID NO: 89           moltype = AA  length = 37
FEATURE                 Location/Qualifiers
source                  1..37
                        mol_type = protein
                        organism = synthetic construct
SEQUENCE: 89
KCNTATCATQ RLADFLRHSS NNLDPILPPT NVGSNTP                         37

SEQ ID NO: 90           moltype = AA  length = 37
FEATURE                 Location/Qualifiers
source                  1..37
                        mol_type = protein
                        organism = synthetic construct
SEQUENCE: 90
KCNTATCATQ RLADFLRHSS NNLNPILPPT NVGSNTP                         37

SEQ ID NO: 91           moltype = AA  length = 37
FEATURE                 Location/Qualifiers
source                  1..37
                        mol_type = protein
                        organism = synthetic construct
SEQUENCE: 91
KCNTATCATQ RLADFLRHSS NNLSPILPPT NVGSNTP                         37

SEQ ID NO: 92           moltype = AA  length = 37
FEATURE                 Location/Qualifiers
source                  1..37
                        mol_type = protein
                        organism = synthetic construct
SITE                    24
                        note = L-lysine
SEQUENCE: 92
KCNTATCATQ RLADFLRHSS NNLXPILPPT NVGSNTP                         37

SEQ ID NO: 93           moltype = AA  length = 37
FEATURE                 Location/Qualifiers
source                  1..37
                        mol_type = protein
                        organism = synthetic construct
SITE                    24
                        note = (S)-2,3-diaminopropanoic acid
SEQUENCE: 93
KCNTATCATQ RLADFLRHSS NNLXPILPPT NVGSNTP                         37
```

```
SEQ ID NO: 94          moltype = AA  length = 37
FEATURE                Location/Qualifiers
source                 1..37
                       mol_type = protein
                       organism = synthetic construct
SITE                   24
                       note = (S)-2,4-diaminobutanoic acid
SEQUENCE: 94
KCNTATCATQ RLADFLRHSS NNLXPILPPT NVGSNTP                    37

SEQ ID NO: 95          moltype = AA  length = 37
FEATURE                Location/Qualifiers
source                 1..37
                       mol_type = protein
                       organism = synthetic construct
SITE                   24
                       note = (S)-2,5-diaminopentanoic acid
SEQUENCE: 95
KCNTATCATQ RLADFLRHSS NNLXPILPPT NVGSNTP                    37

SEQ ID NO: 96          moltype = AA  length = 37
FEATURE                Location/Qualifiers
source                 1..37
                       mol_type = protein
                       organism = synthetic construct
SITE                   24
                       note = (S)-2-amino-5-ureidopentanoic acid
SEQUENCE: 96
KCNTATCATQ RLADFLRHSS NNLXPILPPT NVGSNTP                    37

SEQ ID NO: 97          moltype = AA  length = 37
FEATURE                Location/Qualifiers
source                 1..37
                       mol_type = protein
                       organism = synthetic construct
SITE                   24
                       note = Sarcosine
SEQUENCE: 97
KCNTATCATQ RLADFLRHSS NNLXPILPPT NVGSNTP                    37

SEQ ID NO: 98          moltype = AA  length = 37
FEATURE                Location/Qualifiers
source                 1..37
                       mol_type = protein
                       organism = synthetic construct
SITE                   24
                       note = 4-(aminomethyl)cyclohexane-1-carboxylic acid
SEQUENCE: 98
KCNTATCATQ RLADFLRHSS NNLXPILPPT NVGSNTP                    37

SEQ ID NO: 99          moltype = AA  length = 37
FEATURE                Location/Qualifiers
source                 1..37
                       mol_type = protein
                       organism = synthetic construct
SITE                   24
                       note = 8-Aminooctanoic acid
SEQUENCE: 99
KCNTATCATQ RLADFLRHSS NNLXPILPPT NVGSNTP                    37

SEQ ID NO: 100         moltype = AA  length = 37
FEATURE                Location/Qualifiers
source                 1..37
                       mol_type = protein
                       organism = synthetic construct
SITE                   37
                       note = (S)-azetidine-2-carboxamide
SEQUENCE: 100
KCNTATCATQ RLADFLRHSS NNLGPILPPT NVGSNTX                    37

SEQ ID NO: 101         moltype = AA  length = 37
FEATURE                Location/Qualifiers
source                 1..37
                       mol_type = protein
                       organism = synthetic construct
SITE                   37
                       note = (2S,4R)-4-hydroxypyrrolidine-2-carboxamide
SEQUENCE: 101
KCNTATCATQ RLADFLRHSS NNLKPILPPT NVGSNTX                    37
```

```
SEQ ID NO: 102          moltype = AA  length = 37
FEATURE                 Location/Qualifiers
source                  1..37
                        mol_type = protein
                        organism = synthetic construct
SEQUENCE: 102
KCNTATCATQ RLADFLRHSS NNLKPILPPT NVGSNTP                         37

SEQ ID NO: 103          moltype = AA  length = 37
FEATURE                 Location/Qualifiers
source                  1..37
                        mol_type = protein
                        organism = synthetic construct
SEQUENCE: 103
RCNTATCATQ RLADFLRHSS NNLRPILPPT NVGSNTP                         37

SEQ ID NO: 104          moltype = AA  length = 42
FEATURE                 Location/Qualifiers
source                  1..42
                        mol_type = protein
                        organism = synthetic construct
SEQUENCE: 104
KGGGGRCNTA TCATQRLADF LRHSSNNLRP ILPPTNVGSN TP                   42

SEQ ID NO: 105          moltype = AA  length = 37
FEATURE                 Location/Qualifiers
source                  1..37
                        mol_type = protein
                        organism = synthetic construct
VARIANT                 1
                        note = K, D, (S)-2,4-diaminobutanoic acid,
                         (S)-2,3-diaminopropanoic acid, E, H,
                         (2S)-2-amino-6-(diaminomethylideneamino)hexanoic acid,
                         (S)-2,5-diaminopentanoic acid, R, or absent
VARIANT                 14
                        note = N, (S)-2-aminohexanedioic acid,
                         (S)-2,4-diaminobutanoic acid, (S)-2,3-diaminopropanoic
                         acid, E, or D
VARIANT                 17
                        note = V, (S)-2,5-diaminopentanoic acid, or R
VARIANT                 19
                        note = S or K
VARIANT                 20
                        note = S or K
VARIANT                 21
                        note = N or K
VARIANT                 22
                        note = N or K
VARIANT                 23
                        note = F, L, or K
VARIANT                 24
                        note = G, R, H, P, D, N, S, K, alpha-L-Lysine,
                         (S)-2,3-diaminopropanoic acid, (S)-2,4-diaminobutanoic
                         acid, (S)-2,5-diaminopentanoic acid,
                         (S)-2-amino-5-ureidopentanoic acid, Sarcosine,
                         4-(aminomethyl)cyclohexane-1-carboxylic acid, or
                         8-Aminooctanoic acid
VARIANT                 25
                        note = A, K, or P
VARIANT                 28
                        note = S or P
VARIANT                 29
                        note = S or P
VARIANT                 35
                        note = N or G
VARIANT                 37
                        note = Y, (2S)-3-aminopyrrolidine, (S)-azetidine,
                         (2S,4S)-4-hydroxypyrrolidine, P, (S)-piperidine,
                         (S)-2-methylpyrrolidine, or (2S,4R)-4-hydroxypyrrolidine
SEQUENCE: 105
XCNTATCATQ RLAXFLXHXX XXXXXILXXT NVGSXTX                         37

SEQ ID NO: 106          moltype = AA  length = 37
FEATURE                 Location/Qualifiers
source                  1..37
                        mol_type = protein
                        organism = synthetic construct
VARIANT                 1
```

```
                        note = K, D, (S)-2,4-diaminobutanoic acid,
                         (S)-2,3-diaminopropanoic acid, E, H,
                         (2S)-2-amino-6-(diaminomethylideneamino)hexanoic acid,
                         (S)-2,5-diaminopentanoic acid, R, or absent
VARIANT                 14
                        note = N, (S)-2-aminohexanedioic acid,
                         (S)-2,4-diaminobutanoic acid, (S)-2,3-diaminopropanoic
                         acid, E, or D
VARIANT                 17
                        note = V, (S)-2,5-diaminopentanoic acid, or R
VARIANT                 23
                        note = F, L, or K
VARIANT                 24
                        note = G, R, H, P, D, N, S, K, alpha-L-Lysine,
                         (S)-2,3-diaminopropanoic acid, (S)-2,4-diaminobutanoic
                         acid, (S)-2,5-diaminopentanoic acid,
                         (S)-2-amino-5-ureidopentanoic acid, Sarcosine,
                         4-(aminomethyl)cyclohexane-1-carboxylic acid, or
                         8-Aminooctanoic acid
VARIANT                 25
                        note = A, K, or P
VARIANT                 28
                        note = S or P
VARIANT                 29
                        note = S or P
VARIANT                 37
                        note = Y, (2S)-3-aminopyrrolidine, (S)-azetidine,
                         (2S,4S)-4-hydroxypyrrolidine, P, (S)-piperidine,
                         (S)-2-methylpyrrolidine, or (2S,4R)-4-hydroxypyrrolidine
SEQUENCE: 106
XCNTATCATQ RLAXFLXHSS NNXXXILXXT NVGSNTX                            37

SEQ ID NO: 107          moltype = AA  length = 37
FEATURE                 Location/Qualifiers
source                  1..37
                        mol_type = protein
                        organism = synthetic construct
VARIANT                 1
                        note = K or R
VARIANT                 14
                        note = N, (S)-2-aminohexanedioic acid,
                         (S)-2,4-diaminobutanoic acid, (S)-2,3-diaminopropanoic
                         acid, E, or D
VARIANT                 17
                        note = V, (S)-2,5-diaminopentanoic acid, or R
VARIANT                 19
                        note = S or K
VARIANT                 20
                        note = S or K
VARIANT                 21
                        note = N or K
VARIANT                 22
                        note = N or K
VARIANT                 23
                        note = F, L, or K
VARIANT                 24
                        note = G, R, H, P, D, N, S, K, alpha-L-Lysine,
                         (S)-2,3-diaminopropanoic acid, (S)-2,4-diaminobutanoic
                         acid, (S)-2,5-diaminopentanoic acid,
                         (S)-2-amino-5-ureidopentanoic acid, Sarcosine,
                         4-(aminomethyl)cyclohexane-1-carboxylic acid, or
                         8-Aminooctanoic acid
VARIANT                 25
                        note = A, K, or P
VARIANT                 28
                        note = S or P
VARIANT                 29
                        note = S or P
VARIANT                 35
                        note = N or G
VARIANT                 37
                        note = Y, (2S)-3-aminopyrrolidine, (S)-azetidine,
                         (2S,4S)-4-hydroxypyrrolidine, P, (S)-piperidine,
                         (S)-2-methylpyrrolidine, or (2S,4R)-4-hydroxypyrrolidine
SEQUENCE: 107
XCNTATCATQ RLAXFLXHXX XXXXXILXXT NVGSXTX                            37

SEQ ID NO: 108          moltype = AA  length = 37
FEATURE                 Location/Qualifiers
```

-continued

```
source                  1..37
                        mol_type = protein
                        organism = synthetic construct
VARIANT                 1
                        note = K, D, (S)-2,4-diaminobutanoic acid,
                         (S)-2,3-diaminopropanoic acid, E, H,
                         (2S)-2-amino-6-(diaminomethylideneamino)hexanoic acid,
                         (S)-2,5-diaminopentanoic acid, R, or absent
VARIANT                 14
                        note = N, (S)-2-aminohexanedioic acid,
                         (S)-2,4-diaminobutanoic acid, (S)-2,3-diaminopropanoic
                         acid, E, or D
VARIANT                 17
                        note = V, (S)-2,5-diaminopentanoic acid, or R
VARIANT                 19
                        note = S or K
VARIANT                 20
                        note = S or K
VARIANT                 21
                        note = N or K
VARIANT                 22
                        note = N or K
VARIANT                 23
                        note = F, L, or K
VARIANT                 24
                        note = G, R, or K
VARIANT                 25
                        note = A, K, or P
VARIANT                 28
                        note = S or P
VARIANT                 29
                        note = S or P
VARIANT                 35
                        note = N or G
VARIANT                 37
                        note = Y, (2S)-3-aminopyrrolidine, (S)-azetidine,
                         (2S,4S)-4-hydroxypyrrolidine, P, (S)-piperidine,
                         (S)-2-methylpyrrolidine, or (2S,4R)-4-hydroxypyrrolidine
SEQUENCE: 108
XCNTATCATQ RLAXFLXHXX XXXXXILXXT NVGSXTX                           37

SEQ ID NO: 109          moltype = AA  length = 37
FEATURE                 Location/Qualifiers
source                  1..37
                        mol_type = protein
                        organism = synthetic construct
VARIANT                 1
                        note = K or R
VARIANT                 14
                        note = N, (S)-2-aminohexanedioic acid,
                         (S)-2,4-diaminobutanoic acid, (S)-2,3-diaminopropanoic
                         acid, E, or D
VARIANT                 17
                        note = V, (S)-2,5-diaminopentanoic acid, or R
VARIANT                 19
                        note = S or K
VARIANT                 20
                        note = S or K
VARIANT                 21
                        note = N or K
VARIANT                 22
                        note = N or K
VARIANT                 23
                        note = F, L, or K
VARIANT                 24
                        note = G, R, or K
VARIANT                 25
                        note = A, K, or P
VARIANT                 28
                        note = S or P
VARIANT                 29
                        note = S or P
VARIANT                 35
                        note = N or G
VARIANT                 37
                        note = Y, (2S)-3-aminopyrrolidine, (S)-azetidine,
                         (2S,4S)-4-hydroxypyrrolidine, P, (S)-piperidine,
                         (S)-2-methylpyrrolidine, or (2S,4R)-4-hydroxypyrrolidine
SEQUENCE: 109
```

```
XCNTATCATQ RLAXFLXHXX XXXXXILXXT NVGSXTX                    37

SEQ ID NO: 110          moltype = AA  length = 37
FEATURE                 Location/Qualifiers
source                  1..37
                        mol_type = protein
                        organism = synthetic construct
VARIANT                 14
                        note = N or D
VARIANT                 17
                        note = V or R
VARIANT                 19
                        note = S or K
VARIANT                 20
                        note = S or K
VARIANT                 21
                        note = N or K
VARIANT                 22
                        note = N or K
VARIANT                 23
                        note = F or L
VARIANT                 24
                        note = G or K
VARIANT                 25
                        note = A or P
VARIANT                 28
                        note = S or P
VARIANT                 29
                        note = S or P
VARIANT                 35
                        note = N or G
VARIANT                 37
                        note = Y or (2S,4R)-4-hydroxypyrrolidine
SEQUENCE: 110
KCNTATCATQ RLAXFLXHXX XXXXXILXXT NVGSXTX                    37

SEQ ID NO: 111          moltype = AA  length = 37
FEATURE                 Location/Qualifiers
source                  1..37
                        mol_type = protein
                        organism = synthetic construct
VARIANT                 14
                        note = N or D
VARIANT                 17
                        note = V or R
VARIANT                 19
                        note = S or K
VARIANT                 20
                        note = S or K
VARIANT                 21
                        note = N or K
VARIANT                 22
                        note = N or K
VARIANT                 23
                        note = F or L
VARIANT                 24
                        note = G or K
VARIANT                 25
                        note = A or P
VARIANT                 28
                        note = S or P
VARIANT                 29
                        note = S or P
VARIANT                 35
                        note = N or G
VARIANT                 37
                        note = Y or (2S,4R)-4-hydroxypyrrolidine
SEQUENCE: 111
RCNTATCATQ RLAXFLXHXX XXXXXILXXT NVGSXTX                    37

SEQ ID NO: 112          moltype = AA  length = 37
FEATURE                 Location/Qualifiers
source                  1..37
                        mol_type = protein
                        organism = synthetic construct
VARIANT                 1
                        note = K or R
VARIANT                 19
                        note = S or K
```

```
VARIANT                 20
                        note = S or K
VARIANT                 21
                        note = N or K
VARIANT                 22
                        note = N or K
VARIANT                 24
                        note = G or K
VARIANT                 35
                        note = N or G
SITE                    37
                        note = (2S,4R)-4-hydroxypyrrolidine
SEQUENCE: 112
XCNTATCATQ RLADFLRHXX XXLXPILPPT NVGSXTX                            37

SEQ ID NO: 113          moltype = AA  length = 37
FEATURE                 Location/Qualifiers
source                  1..37
                        mol_type = protein
                        organism = synthetic construct
VARIANT                 19
                        note = S or K
VARIANT                 20
                        note = S or K
VARIANT                 21
                        note = N or K
VARIANT                 22
                        note = N or K
VARIANT                 24
                        note = G or K
VARIANT                 35
                        note = N or G
SITE                    37
                        note = (2S,4R)-4-hydroxypyrrolidine
SEQUENCE: 113
KCNTATCATQ RLADFLRHXX XXLXPILPPT NVGSXTX                            37

SEQ ID NO: 114          moltype = AA  length = 37
FEATURE                 Location/Qualifiers
source                  1..37
                        mol_type = protein
                        organism = synthetic construct
VARIANT                 19
                        note = S or K
VARIANT                 20
                        note = S or K
VARIANT                 21
                        note = N or K
VARIANT                 22
                        note = N or K
VARIANT                 35
                        note = N or G
SITE                    37
                        note = (2S,4R)-4-hydroxypyrrolidine
SEQUENCE: 114
KCNTATCATQ RLADFLRHXX XXLKPILPPT NVGSXTX                            37

SEQ ID NO: 115          moltype = AA  length = 37
FEATURE                 Location/Qualifiers
source                  1..37
                        mol_type = protein
                        organism = synthetic construct
VARIANT                 1
                        note = K, D, (S)-2,4-diaminobutanoic acid,
                         (S)-2,3-diaminopropanoic acid, E, H,
                         (2S)-2-amino-6-(diaminomethylideneamino)hexanoic acid,
                         (S)-2,5-diaminopentanoic acid, R, or absent
VARIANT                 14
                        note = N, (S)-2-aminohexanedioic acid,
                         (S)-2,4-diaminobutanoic acid, (S)-2,3-diaminopropanoic
                         acid, E, or D
VARIANT                 17
                        note = V, (S)-2,5-diaminopentanoic acid, or R
VARIANT                 19
                        note = S or K
VARIANT                 20
                        note = S or K
VARIANT                 21
                        note = N or K
```

-continued

```
VARIANT                 22
                        note = N or K
VARIANT                 23
                        note = F, L, or K
VARIANT                 24
                        note = G, R, H, P, D, N, S, K, alpha-L-Lysine,
                         (S)-2,3-diaminopropanoic acid, (S)-2,4-diaminobutanoic
                         acid, (S)-2,5-diaminopentanoic acid,
                         (S)-2-amino-5-ureidopentanoic acid, Sarcosine,
                         4-(aminomethyl)cyclohexane-1-carboxylic acid, or
                         8-Aminooctanoic acid
VARIANT                 25
                        note = A, K, or P
VARIANT                 28
                        note = S or P
VARIANT                 29
                        note = S or P
VARIANT                 35
                        note = N or G
VARIANT                 37
                        note = P or (2S,4R)-4-hydroxypyrrolidine
SEQUENCE: 115
XCNTATCATQ RLAXFLXHXX XXXXXILXXT NVGSXTX                            37

SEQ ID NO: 116          moltype = AA  length = 37
FEATURE                 Location/Qualifiers
source                  1..37
                        mol_type = protein
                        organism = synthetic construct
VARIANT                 1
                        note = K or R
VARIANT                 14
                        note = N, (S)-2-aminohexanedioic acid,
                         (S)-2,4-diaminobutanoic acid, (S)-2,3-diaminopropanoic
                         acid, E, or D
VARIANT                 17
                        note = V, (S)-2,5-diaminopentanoic acid, or R
VARIANT                 19
                        note = S or K
VARIANT                 20
                        note = S or K
VARIANT                 21
                        note = N or K
VARIANT                 22
                        note = N or K
VARIANT                 23
                        note = F, L, or K
VARIANT                 24
                        note = G, R, or K
VARIANT                 25
                        note = A, K, or P
VARIANT                 28
                        note = S or P
VARIANT                 29
                        note = S or P
VARIANT                 35
                        note = N or G
VARIANT                 37
                        note = P or (2S,4R)-4-hydroxypyrrolidine
SEQUENCE: 116
XCNTATCATQ RLAXFLXHXX XXXXXILXXT NVGSXTX                            37

SEQ ID NO: 117          moltype = AA  length = 37
FEATURE                 Location/Qualifiers
source                  1..37
                        mol_type = protein
                        organism = synthetic construct
SITE                    21
                        note = Lysine modified with
                         (2-(2-(2-aminoethoxy)ethoxy)acetic acid)2-Gamma-glutamic
                         acid-C20 diacid via the side chain
SITE                    37
                        note = Amidated residue
SEQUENCE: 117
RCNTATCATQ RLAEFLRHSS KNLGPILPPT NVGSNTP                            37

SEQ ID NO: 118          moltype = AA  length = 37
FEATURE                 Location/Qualifiers
source                  1..37
```

```
                        mol_type = protein
                        organism = synthetic construct
SITE                    22
                        note = Lysine modified with
                         (2-(2-(2-aminoethoxy)ethoxy)acetic acid)2-Gamma-glutamic
                         acid-C20 diacid via the side chain
SITE                    37
                        note = Amidated residue
SEQUENCE: 118
RCNTATCATQ RLAEFLRHSS NKLGPILPPT NVGSNTP                             37

SEQ ID NO: 119          moltype = AA  length = 37
FEATURE                 Location/Qualifiers
source                  1..37
                        mol_type = protein
                        organism = synthetic construct
SITE                    23
                        note = Lysine modified with
                         (2-(2-(2-aminoethoxy)ethoxy)acetic acid)2-Gamma-glutamic
                         acid-C20 diacid via the side chain
SITE                    37
                        note = Amidated residue
SEQUENCE: 119
RCNTATCATQ RLAEFLRHSS NNKGPILPPT NVGSNTP                             37

SEQ ID NO: 120          moltype = AA  length = 37
FEATURE                 Location/Qualifiers
source                  1..37
                        mol_type = protein
                        organism = synthetic construct
SITE                    24
                        note = Lysine modified with
                         (2-(2-(2-aminoethoxy)ethoxy)acetic acid)2-Gamma-glutamic
                         acid-C20 diacid via the side chain
SITE                    37
                        note = Amidated residue
SEQUENCE: 120
RCNTATCATQ RLAEFLRHSS NNLKPILPPT NVGSNTP                             37

SEQ ID NO: 121          moltype = AA  length = 37
FEATURE                 Location/Qualifiers
source                  1..37
                        mol_type = protein
                        organism = synthetic construct
SITE                    25
                        note = Lysine modified with
                         (2-(2-(2-aminoethoxy)ethoxy)acetic acid)2-Gamma-glutamic
                         acid-C20 diacid via the side chain
SITE                    37
                        note = Amidated residue
SEQUENCE: 121
RCNTATCATQ RLAEFLRHSS NNLGKILPPT NVGSNTP                             37

SEQ ID NO: 122          moltype = AA  length = 37
FEATURE                 Location/Qualifiers
source                  1..37
                        mol_type = protein
                        organism = synthetic construct
SITE                    21
                        note = Lysine modified with Gamma-glutamic acid-C20 diacid
                         via the side chain
SITE                    37
                        note = Amidated residue
SEQUENCE: 122
RCNTATCATQ RLAEFLRHSS KNLGPILPPT NVGSNTP                             37

SEQ ID NO: 123          moltype = AA  length = 37
FEATURE                 Location/Qualifiers
source                  1..37
                        mol_type = protein
                        organism = synthetic construct
SITE                    22
                        note = Lysine modified with Gamma-glutamic acid-C20 diacid
                         via the side chain
SITE                    37
                        note = Amidated residue
SEQUENCE: 123
RCNTATCATQ RLAEFLRHSS NKLGPILPPT NVGSNTP                             37
```

```
SEQ ID NO: 124          moltype = AA  length = 37
FEATURE                 Location/Qualifiers
source                  1..37
                        mol_type = protein
                        organism = synthetic construct
SITE                    23
                        note = Lysine modified with Gamma-glutamic acid-C20 diacid
                         via the side chain
SITE                    37
                        note = Amidated residue
SEQUENCE: 124
RCNTATCATQ RLAEFLRHSS NNKGPILPPT NVGSNTP                            37

SEQ ID NO: 125          moltype = AA  length = 37
FEATURE                 Location/Qualifiers
source                  1..37
                        mol_type = protein
                        organism = synthetic construct
SITE                    24
                        note = Lysine modified with Gamma-glutamic acid-C20 diacid
                         via the side chain
SITE                    37
                        note = Amidated residue
SEQUENCE: 125
RCNTATCATQ RLAEFLRHSS NNLKPILPPT NVGSNTP                            37

SEQ ID NO: 126          moltype = AA  length = 37
FEATURE                 Location/Qualifiers
source                  1..37
                        mol_type = protein
                        organism = synthetic construct
SITE                    25
                        note = Lysine modified with Gamma-glutamic acid-C20 diacid
                         via the side chain
SITE                    37
                        note = Amidated residue
SEQUENCE: 126
RCNTATCATQ RLAEFLRHSS NNLGKILPPT NVGSNTP                            37

SEQ ID NO: 127          moltype = AA  length = 37
FEATURE                 Location/Qualifiers
source                  1..37
                        mol_type = protein
                        organism = synthetic construct
SITE                    24
                        note = Lysine modified with Gamma-glutamic acid-C20 diacid
                         via the side chain
SITE                    37
                        note = Amidated residue
SEQUENCE: 127
RCNTATCATQ RLAEFLRHSS NNLKPILSST NVGSNTP                            37

SEQ ID NO: 128          moltype = AA  length = 37
FEATURE                 Location/Qualifiers
source                  1..37
                        mol_type = protein
                        organism = synthetic construct
SITE                    24
                        note = Lysine modified with Gamma-glutamic acid-C20 diacid
                         via the side chain
SITE                    37
                        note = Amidated residue
SEQUENCE: 128
RCNTATCATQ RLAEFLRHSS NNLKAILPST NVGSNTP                            37

SEQ ID NO: 129          moltype = AA  length = 37
FEATURE                 Location/Qualifiers
source                  1..37
                        mol_type = protein
                        organism = synthetic construct
SITE                    24
                        note = Lysine modified with Gamma-glutamic acid-C20 diacid
                         via the side chain
SITE                    37
                        note = Amidated residue
SEQUENCE: 129
RCNTATCATQ RLAEFLRHSS NNLKAILSPT NVGSNTP                            37

SEQ ID NO: 130          moltype = AA  length = 37
```

-continued

```
FEATURE                Location/Qualifiers
source                 1..37
                       mol_type = protein
                       organism = synthetic construct
SITE                   24
                       note = Lysine modified with Gamma-glutamic acid-C20 diacid
                        via the side chain
SITE                   37
                       note = Amidated residue
SEQUENCE: 130
RCNTATCATQ RLAEFLRHSS NNLKPILPST NVGSNTP                            37

SEQ ID NO: 131         moltype = AA  length = 37
FEATURE                Location/Qualifiers
source                 1..37
                       mol_type = protein
                       organism = synthetic construct
SITE                   24
                       note = Lysine modified with Gamma-glutamic acid-C20 diacid
                        via the side chain
SITE                   37
                       note = Amidated residue
SEQUENCE: 131
RCNTATCATQ RLAEFLRHSS NNLKPILSPT NVGSNTP                            37

SEQ ID NO: 132         moltype = AA  length = 37
FEATURE                Location/Qualifiers
source                 1..37
                       mol_type = protein
                       organism = synthetic construct
SITE                   24
                       note = Lysine modified with Gamma-glutamic acid-C20 diacid
                        via the side chain
SITE                   37
                       note = Amidated residue
SEQUENCE: 132
RCNTATCATQ RLAEFLRHSS NNLKAILPPT NVGSNTP                            37

SEQ ID NO: 133         moltype = AA  length = 37
FEATURE                Location/Qualifiers
source                 1..37
                       mol_type = protein
                       organism = synthetic construct
SITE                   24
                       note = Lysine modified with Gamma-glutamic acid-C20 diacid
                        via the side chain
SITE                   37
                       note = Amidated residue
SEQUENCE: 133
RCNTATCATQ RLAEFLRHSS NNLKPILPPT NVGSNTY                            37

SEQ ID NO: 134         moltype = AA  length = 37
FEATURE                Location/Qualifiers
source                 1..37
                       mol_type = protein
                       organism = synthetic construct
SITE                   24
                       note = Lysine modified with Gamma-glutamic acid-C20 diacid
                        via the side chain
SITE                   37
                       note = Amidated residue
SEQUENCE: 134
RCNTATCATQ RLAEFLRHSS NNLKAILSST NVGSNTY                            37

SEQ ID NO: 135         moltype = AA  length = 37
FEATURE                Location/Qualifiers
source                 1..37
                       mol_type = protein
                       organism = synthetic construct
SITE                   24
                       note = Lysine modified with Gamma-glutamic acid-C20 diacid
                        via the side chain
SITE                   37
                       note = Amidated residue
SEQUENCE: 135
RCNTATCATQ RLAEFLRHSS NNLKPILSST NVGSNTY                            37

SEQ ID NO: 136         moltype = AA  length = 37
FEATURE                Location/Qualifiers
```

-continued

```
source                1..37
                      mol_type = protein
                      organism = synthetic construct
SITE                  24
                      note = Lysine modified with Gamma-glutamic acid-C20 diacid
                       via the side chain
SITE                  37
                      note = Amidated residue
SEQUENCE: 136
RCNTATCATQ RLAEFLRHSS NNLKAILPST NVGSNTY                      37

SEQ ID NO: 137        moltype = AA  length = 37
FEATURE               Location/Qualifiers
source                1..37
                      mol_type = protein
                      organism = synthetic construct
SITE                  24
                      note = Lysine modified with Gamma-glutamic acid-C20 diacid
                       via the side chain
SITE                  37
                      note = Amidated residue
SEQUENCE: 137
RCNTATCATQ RLAEFLRHSS NNLKAILSPT NVGSNTY                      37

SEQ ID NO: 138        moltype = AA  length = 37
FEATURE               Location/Qualifiers
source                1..37
                      mol_type = protein
                      organism = synthetic construct
SITE                  24
                      note = Lysine modified with Gamma-glutamic acid-C20 diacid
                       via the side chain
SITE                  37
                      note = Amidated residue
SEQUENCE: 138
RCNTATCATQ RLAEFLRHSS NNLKPILPST NVGSNTY                      37

SEQ ID NO: 139        moltype = AA  length = 37
FEATURE               Location/Qualifiers
source                1..37
                      mol_type = protein
                      organism = synthetic construct
SITE                  24
                      note = Lysine modified with Gamma-glutamic acid-C20 diacid
                       via the side chain
SITE                  37
                      note = Amidated residue
SEQUENCE: 139
RCNTATCATQ RLAEFLRHSS NNLKPILSPT NVGSNTY                      37

SEQ ID NO: 140        moltype = AA  length = 37
FEATURE               Location/Qualifiers
source                1..37
                      mol_type = protein
                      organism = synthetic construct
SITE                  24
                      note = Lysine modified with Gamma-glutamic acid-C20 diacid
                       via the side chain
SITE                  37
                      note = Amidated residue
SEQUENCE: 140
RCNTATCATQ RLAEFLRHSS NNLKAILPPT NVGSNTY                      37

SEQ ID NO: 141        moltype = AA  length = 37
FEATURE               Location/Qualifiers
source                1..37
                      mol_type = protein
                      organism = synthetic construct
SITE                  24
                      note = Lysine modified with Gamma-glutamic acid-C20 diacid
                       via the side chain
SITE                  37
                      note = Amidated residue
SEQUENCE: 141
RCNTATCATQ RLAEFLRHSS NNLKPILPPT NVGSGTP                      37

SEQ ID NO: 142        moltype = AA  length = 37
FEATURE               Location/Qualifiers
source                1..37
```

```
                        mol_type = protein
                        organism = synthetic construct
SITE                    24
                        note = Lysine modified with Gamma-glutamic acid-C20 diacid
                         via the side chain
SITE                    37
                        note = Amidated residue
SEQUENCE: 142
RCNTATCATQ RLAEFLRHSS NNLKAILSST NVGSGTP                            37

SEQ ID NO: 143          moltype = AA  length = 37
FEATURE                 Location/Qualifiers
source                  1..37
                        mol_type = protein
                        organism = synthetic construct
SITE                    24
                        note = Lysine modified with Gamma-glutamic acid-C20 diacid
                         via the side chain
SITE                    37
                        note = Amidated residue
SEQUENCE: 143
RCNTATCATQ RLAEFLRHSS NNLKPILSST NVGSGTP                            37

SEQ ID NO: 144          moltype = AA  length = 37
FEATURE                 Location/Qualifiers
source                  1..37
                        mol_type = protein
                        organism = synthetic construct
SITE                    24
                        note = Lysine modified with Gamma-glutamic acid-C20 diacid
                         via the side chain
SITE                    37
                        note = Amidated residue
SEQUENCE: 144
RCNTATCATQ RLAEFLRHSS NNLKAILPST NVGSGTP                            37

SEQ ID NO: 145          moltype = AA  length = 37
FEATURE                 Location/Qualifiers
source                  1..37
                        mol_type = protein
                        organism = synthetic construct
SITE                    24
                        note = Lysine modified with Gamma-glutamic acid-C20 diacid
                         via the side chain
SITE                    37
                        note = Amidated residue
SEQUENCE: 145
RCNTATCATQ RLAEFLRHSS NNLKAILSPT NVGSGTP                            37

SEQ ID NO: 146          moltype = AA  length = 37
FEATURE                 Location/Qualifiers
source                  1..37
                        mol_type = protein
                        organism = synthetic construct
SITE                    24
                        note = Lysine modified with Gamma-glutamic acid-C20 diacid
                         via the side chain
SITE                    37
                        note = Amidated residue
SEQUENCE: 146
RCNTATCATQ RLAEFLRHSS NNLKPILPST NVGSGTP                            37

SEQ ID NO: 147          moltype = AA  length = 37
FEATURE                 Location/Qualifiers
source                  1..37
                        mol_type = protein
                        organism = synthetic construct
SITE                    24
                        note = Lysine modified with Gamma-glutamic acid-C20 diacid
                         via the side chain
SITE                    37
                        note = Amidated residue
SEQUENCE: 147
RCNTATCATQ RLAEFLRHSS NNLKPILSPT NVGSGTP                            37

SEQ ID NO: 148          moltype = AA  length = 37
FEATURE                 Location/Qualifiers
source                  1..37
                        mol_type = protein
```

```
                        organism = synthetic construct
SITE                    24
                        note = Lysine modified with Gamma-glutamic acid-C20 diacid
                         via the side chain
SITE                    37
                        note = Amidated residue
SEQUENCE: 148
RCNTATCATQ RLAEFLRHSS NNLKAILPPT NVGSGTP                           37

SEQ ID NO: 149          moltype = AA  length = 37
FEATURE                 Location/Qualifiers
source                  1..37
                        mol_type = protein
                        organism = synthetic construct
SITE                    24
                        note = Lysine modified with Gamma-glutamic acid-C20 diacid
                         via the side chain
SITE                    37
                        note = Amidated residue
SEQUENCE: 149
KCNTATCATQ RLAEFLRHSS NNLKPILPPT NVGSNTP                           37

SEQ ID NO: 150          moltype = AA  length = 37
FEATURE                 Location/Qualifiers
source                  1..37
                        mol_type = protein
                        organism = synthetic construct
SITE                    24
                        note = Lysine modified with Gamma-glutamic acid-C20 diacid
                         via the side chain
SITE                    37
                        note = Amidated residue
SEQUENCE: 150
KCNTATCATQ RLAEFLRHSS NNLKPILSST NVGSNTP                           37

SEQ ID NO: 151          moltype = AA  length = 37
FEATURE                 Location/Qualifiers
source                  1..37
                        mol_type = protein
                        organism = synthetic construct
SITE                    24
                        note = Lysine modified with Gamma-glutamic acid-C20 diacid
                         via the side chain
SITE                    37
                        note = Amidated residue
SEQUENCE: 151
KCNTATCATQ RLAEFLRHSS NNLKAILPST NVGSNTP                           37

SEQ ID NO: 152          moltype = AA  length = 37
FEATURE                 Location/Qualifiers
source                  1..37
                        mol_type = protein
                        organism = synthetic construct
SITE                    24
                        note = Lysine modified with Gamma-glutamic acid-C20 diacid
                         via the side chain
SITE                    37
                        note = Amidated residue
SEQUENCE: 152
KCNTATCATQ RLAEFLRHSS NNLKAILSPT NVGSNTP                           37

SEQ ID NO: 153          moltype = AA  length = 37
FEATURE                 Location/Qualifiers
source                  1..37
                        mol_type = protein
                        organism = synthetic construct
SITE                    24
                        note = Lysine modified with Gamma-glutamic acid-C20 diacid
                         via the side chain
SITE                    37
                        note = Amidated residue
SEQUENCE: 153
KCNTATCATQ RLAEFLRHSS NNLKPILPST NVGSNTP                           37

SEQ ID NO: 154          moltype = AA  length = 37
FEATURE                 Location/Qualifiers
source                  1..37
                        mol_type = protein
                        organism = synthetic construct
```

```
SITE                    24
                        note = Lysine modified with Gamma-glutamic acid-C20 diacid
                         via the side chain
SITE                    37
                        note = Amidated residue
SEQUENCE: 154
KCNTATCATQ RLAEFLRHSS NNLKPILSPT NVGSNTP                            37

SEQ ID NO: 155          moltype = AA  length = 37
FEATURE                 Location/Qualifiers
source                  1..37
                        mol_type = protein
                        organism = synthetic construct
SITE                    24
                        note = Lysine modified with Gamma-glutamic acid-C20 diacid
                         via the side chain
SITE                    37
                        note = Amidated residue
SEQUENCE: 155
KCNTATCATQ RLAEFLRHSS NNLKAILPPT NVGSNTP                            37

SEQ ID NO: 156          moltype = AA  length = 37
FEATURE                 Location/Qualifiers
source                  1..37
                        mol_type = protein
                        organism = synthetic construct
SITE                    24
                        note = Lysine modified with Gamma-glutamic acid-C20 diacid
                         via the side chain
SITE                    37
                        note = (2S,4R)-4-hydroxypyrrolidine-2-carboxamide
SEQUENCE: 156
RCNTATCATQ RLAEFLRHSS NNLKPILPPT NVGSNTX                            37

SEQ ID NO: 157          moltype = AA  length = 37
FEATURE                 Location/Qualifiers
source                  1..37
                        mol_type = protein
                        organism = synthetic construct
SITE                    24
                        note = Lysine modified with Gamma-glutamic acid-C20 diacid
                         via the side chain
SITE                    37
                        note = (2S,4R)-4-hydroxypyrrolidine-2-carboxamide
SEQUENCE: 157
RCNTATCATQ RLAEFLRHSS NNLKPILPPT NVGSGTX                            37

SEQ ID NO: 158          moltype = AA  length = 37
FEATURE                 Location/Qualifiers
source                  1..37
                        mol_type = protein
                        organism = synthetic construct
SITE                    24
                        note = Lysine modified with Gamma-glutamic acid-C20 diacid
                         via the side chain
SITE                    37
                        note = Amidated residue
SEQUENCE: 158
RCNTATCATQ RLADFLRHSS NNLKPILPPT NVGSNTP                            37

SEQ ID NO: 159          moltype = AA  length = 37
FEATURE                 Location/Qualifiers
source                  1..37
                        mol_type = protein
                        organism = synthetic construct
SITE                    14
                        note = (S)-2-aminohexanedioic acid
SITE                    24
                        note = Lysine modified with Gamma-glutamic acid-C20 diacid
                         via the side chain
SITE                    37
                        note = Amidated residue
SEQUENCE: 159
RCNTATCATQ RLAXFLRHSS NNLKPILPPT NVGSNTP                            37

SEQ ID NO: 160          moltype = AA  length = 37
FEATURE                 Location/Qualifiers
source                  1..37
                        mol_type = protein
```

-continued

```
                         organism = synthetic construct
SITE                     14
                         note = (S)-2,4-diaminobutanoic acid
SITE                     24
                         note = Lysine modified with Gamma-glutamic acid-C20 diacid
                          via the side chain
SITE                     37
                         note = Amidated residue
SEQUENCE: 160
RCNTATCATQ RLAXFLRHSS NNLKPILPPT NVGSNTP                            37

SEQ ID NO: 161           moltype = AA  length = 37
FEATURE                  Location/Qualifiers
source                   1..37
                         mol_type = protein
                         organism = synthetic construct
SITE                     14
                         note = (S)-2,3-diaminopropanoic acid
SITE                     24
                         note = Lysine modified with Gamma-glutamic acid-C20 diacid
                          via the side chain
SITE                     37
                         note = Amidated residue
SEQUENCE: 161
RCNTATCATQ RLAXFLRHSS NNLKPILPPT NVGSNTP                            37

SEQ ID NO: 162           moltype = AA  length = 37
FEATURE                  Location/Qualifiers
source                   1..37
                         mol_type = protein
                         organism = synthetic construct
SITE                     17
                         note = (S)-2,5-diaminopentanoic acid
SITE                     24
                         note = Lysine modified with Gamma-glutamic acid-C20 diacid
                          via the side chain
SITE                     37
                         note = Amidated residue
SEQUENCE: 162
RCNTATCATQ RLAEFLXHSS NNLKPILPPT NVGSNTP                            37

SEQ ID NO: 163           moltype = AA  length = 36
FEATURE                  Location/Qualifiers
source                   1..36
                         mol_type = protein
                         organism = synthetic construct
SITE                     23
                         note = Lysine modified with Gamma-glutamic acid-C20 diacid
                          via the side chain
SITE                     36
                         note = Amidated residue
SEQUENCE: 163
CNTATCATQR LAEFLRHSSN NLKPILPPTN VGSNTP                             36

SEQ ID NO: 164           moltype = AA  length = 36
FEATURE                  Location/Qualifiers
source                   1..36
                         mol_type = protein
                         organism = synthetic construct
SITE                     23
                         note = Lysine modified with Gamma-glutamic acid-C20 diacid
                          via the side chain
SITE                     36
                         note = Amidated residue
SEQUENCE: 164
CNTATCATQR LADFLRHSSN NLKPILPPTN VGSNTP                             36

SEQ ID NO: 165           moltype = AA  length = 37
FEATURE                  Location/Qualifiers
source                   1..37
                         mol_type = protein
                         organism = synthetic construct
SITE                     24
                         note = Lysine modified with Gamma-glutamic acid-C20 diacid
                          via the side chain
SITE                     37
                         note = (2S,4R)-4-hydroxypyrrolidine-2-carboxamide
SEQUENCE: 165
RCNTATCATQ RLADFLRHSS NNLKPILPPT NVGSNTX                            37
```

```
SEQ ID NO: 166          moltype = AA  length = 36
FEATURE                 Location/Qualifiers
source                  1..36
                        mol_type = protein
                        organism = synthetic construct
SITE                    23
                        note = Lysine modified with Gamma-glutamic acid-C20 diacid
                         via the side chain
SITE                    36
                        note = (2S,4R)-4-hydroxypyrrolidine-2-carboxamide
SEQUENCE: 166
CNTATCATQR LAEFLRHSSN NLKPILPPTN VGSNTX                             36

SEQ ID NO: 167          moltype = AA  length = 36
FEATURE                 Location/Qualifiers
source                  1..36
                        mol_type = protein
                        organism = synthetic construct
SITE                    23
                        note = Lysine modified with Gamma-glutamic acid-C20 diacid
                         via the side chain
SITE                    36
                        note = (2S,4R)-4-hydroxypyrrolidine-2-carboxamide
SEQUENCE: 167
CNTATCATQR LADFLRHSSN NLKPILPPTN VGSNTX                             36

SEQ ID NO: 168          moltype = AA  length = 37
FEATURE                 Location/Qualifiers
source                  1..37
                        mol_type = protein
                        organism = synthetic construct
SITE                    24
                        note = Lysine modified with Gamma-glutamic acid-C20 diacid
                         via the side chain
SITE                    37
                        note = (2S,4S)-4-hydroxypyrrolidine-2-carboxamide
SEQUENCE: 168
RCNTATCATQ RLAEFLRHSS NNLKPILPPT NVGSNTX                            37

SEQ ID NO: 169          moltype = AA  length = 37
FEATURE                 Location/Qualifiers
source                  1..37
                        mol_type = protein
                        organism = synthetic construct
SITE                    24
                        note = Lysine modified with Gamma-glutamic acid-C20 diacid
                         via the side chain
SITE                    37
                        note = (2S,4S)-4-hydroxypyrrolidine-2-carboxamide
SEQUENCE: 169
RCNTATCATQ RLADFLRHSS NNLKPILPPT NVGSNTX                            37

SEQ ID NO: 170          moltype = AA  length = 37
FEATURE                 Location/Qualifiers
source                  1..37
                        mol_type = protein
                        organism = synthetic construct
SITE                    24
                        note = Lysine modified with Gamma-glutamic acid-C20 diacid
                         via the side chain
SITE                    37
                        note = (S)-piperidine-2-carboxamide
SEQUENCE: 170
RCNTATCATQ RLAEFLRHSS NNLKPILPPT NVGSNTX                            37

SEQ ID NO: 171          moltype = AA  length = 37
FEATURE                 Location/Qualifiers
source                  1..37
                        mol_type = protein
                        organism = synthetic construct
SITE                    24
                        note = Lysine modified with Gamma-glutamic acid-C20 diacid
                         via the side chain
SITE                    37
                        note = (S)-piperidine-2-carboxamide
SEQUENCE: 171
RCNTATCATQ RLADFLRHSS NNLKPILPPT NVGSNTX                            37
```

```
SEQ ID NO: 172          moltype = AA  length = 37
FEATURE                 Location/Qualifiers
source                  1..37
                        mol_type = protein
                        organism = synthetic construct
SITE                    24
                        note = Lysine modified with Gamma-glutamic acid-C20 diacid
                         via the side chain
SITE                    37
                        note = (S)-azetidine-2-carboxamide
SEQUENCE: 172
RCNTATCATQ RLAEFLRHSS NNLKPILPPT NVGSNTX                             37

SEQ ID NO: 173          moltype = AA  length = 37
FEATURE                 Location/Qualifiers
source                  1..37
                        mol_type = protein
                        organism = synthetic construct
SITE                    24
                        note = Lysine modified with Gamma-glutamic acid-C20 diacid
                         via the side chain
SITE                    37
                        note = (S)-azetidine-2-carboxamide
SEQUENCE: 173
RCNTATCATQ RLADFLRHSS NNLKPILPPT NVGSNTX                             37

SEQ ID NO: 174          moltype = AA  length = 37
FEATURE                 Location/Qualifiers
source                  1..37
                        mol_type = protein
                        organism = synthetic construct
SITE                    24
                        note = Lysine modified with Gamma-glutamic acid-C20 diacid
                         via the side chain
SITE                    37
                        note = (2S)-3-aminopyrrolidine-2-carboxamide
SEQUENCE: 174
RCNTATCATQ RLAEFLRHSS NNLKPILPPT NVGSNTX                             37

SEQ ID NO: 175          moltype = AA  length = 37
FEATURE                 Location/Qualifiers
source                  1..37
                        mol_type = protein
                        organism = synthetic construct
SITE                    24
                        note = Lysine modified with Gamma-glutamic acid-C20 diacid
                         via the side chain
SITE                    37
                        note = (2S)-3-aminopyrrolidine-2-carboxamide
SEQUENCE: 175
RCNTATCATQ RLADFLRHSS NNLKPILPPT NVGSNTX                             37

SEQ ID NO: 176          moltype = AA  length = 37
FEATURE                 Location/Qualifiers
source                  1..37
                        mol_type = protein
                        organism = synthetic construct
SITE                    24
                        note = Lysine modified with Gamma-glutamic acid-C20 diacid
                         via the side chain
SITE                    37
                        note = (S)-2-methylpyrrolidine-2-carboxamide
SEQUENCE: 176
RCNTATCATQ RLAEFLRHSS NNLKPILPPT NVGSNTX                             37

SEQ ID NO: 177          moltype = AA  length = 37
FEATURE                 Location/Qualifiers
source                  1..37
                        mol_type = protein
                        organism = synthetic construct
SITE                    24
                        note = Lysine modified with Gamma-glutamic acid-C20 diacid
                         via the side chain
SITE                    37
                        note = (S)-2-methylpyrrolidine-2-carboxamide
SEQUENCE: 177
RCNTATCATQ RLADFLRHSS NNLKPILPPT NVGSNTX                             37

SEQ ID NO: 178          moltype = AA  length = 37
```

-continued

```
FEATURE                Location/Qualifiers
source                 1..37
                       mol_type = protein
                       organism = synthetic construct
SITE                   37
                       note = Amidated residue
SEQUENCE: 178
KCNTATCATQ RLAEFLRHSS NNFGPILPPT NVGSNTP                            37

SEQ ID NO: 179         moltype = AA  length = 37
FEATURE                Location/Qualifiers
source                 1..37
                       mol_type = protein
                       organism = synthetic construct
SITE                   1
                       note = Lysine modified with Gamma-glutamic acid-C20 diacid
                        via the side chain
SITE                   37
                       note = Amidated residue
SEQUENCE: 179
KCNTATCATQ RLAEFLRHSS NNFGPILPPT NVGSNTP                            37

SEQ ID NO: 180         moltype = AA  length = 37
FEATURE                Location/Qualifiers
source                 1..37
                       mol_type = protein
                       organism = synthetic construct
SITE                   37
                       note = (2S,4R)-4-hydroxypyrrolidine-2-carboxamide
SEQUENCE: 180
KCNTATCATQ RLADFLRHSS NNFGPILPPT NVGSNTX                            37

SEQ ID NO: 181         moltype = AA  length = 37
FEATURE                Location/Qualifiers
source                 1..37
                       mol_type = protein
                       organism = synthetic construct
SITE                   1
                       note = Lysine modified with Gamma-glutamic acid-C20 diacid
                        via the side chain
SITE                   37
                       note = (2S,4R)-4-hydroxypyrrolidine-2-carboxamide
SEQUENCE: 181
KCNTATCATQ RLADFLRHSS NNFGPILPPT NVGSNTX                            37

SEQ ID NO: 182         moltype = AA  length = 37
FEATURE                Location/Qualifiers
source                 1..37
                       mol_type = protein
                       organism = synthetic construct
SITE                   37
                       note = (2S,4R)-4-hydroxypyrrolidine-2-carboxamide
SEQUENCE: 182
KCNTATCATQ RLADFLRHSS NNLGPILPPT NVGSNTX                            37

SEQ ID NO: 183         moltype = AA  length = 37
FEATURE                Location/Qualifiers
source                 1..37
                       mol_type = protein
                       organism = synthetic construct
SITE                   1
                       note = Lysine modified with Gamma-glutamic acid-C20 diacid
                        via the side chain
SITE                   37
                       note = (2S,4R)-4-hydroxypyrrolidine-2-carboxamide
SEQUENCE: 183
KCNTATCATQ RLADFLRHSS NNLGPILPPT NVGSNTX                            37

SEQ ID NO: 184         moltype = AA  length = 37
FEATURE                Location/Qualifiers
source                 1..37
                       mol_type = protein
                       organism = synthetic construct
SITE                   37
                       note = (2S,4R)-4-hydroxypyrrolidine-2-carboxamide
SEQUENCE: 184
KCNTATCATQ RLADFLRHSS NNLKPILPPT NVGSNTX                            37

SEQ ID NO: 185         moltype = AA  length = 37
```

-continued

```
FEATURE                 Location/Qualifiers
source                  1..37
                        mol_type = protein
                        organism = synthetic construct
SITE                    1
                        note = Lysine modified with Gamma-glutamic acid-C20 diacid
                         via the side chain
SITE                    37
                        note = (2S,4R)-4-hydroxypyrrolidine-2-carboxamide
SEQUENCE: 185
KCNTATCATQ RLADFLRHSS NNLKPILPPT NVGSNTX                           37

SEQ ID NO: 186          moltype = AA  length = 37
FEATURE                 Location/Qualifiers
source                  1..37
                        mol_type = protein
                        organism = synthetic construct
SITE                    1
                        note = (S)-2,3-diaminopropanoic acid
SITE                    24
                        note = Lysine modified with Gamma-glutamic acid-C20 diacid
                         via the side chain
SITE                    37
                        note = (2S,4R)-4-hydroxypyrrolidine-2-carboxamide
SEQUENCE: 186
XCNTATCATQ RLADFLRHSS NNLKPILPPT NVGSNTX                           37

SEQ ID NO: 187          moltype = AA  length = 37
FEATURE                 Location/Qualifiers
source                  1..37
                        mol_type = protein
                        organism = synthetic construct
SITE                    1
                        note = (S)-2,4-diaminobutanoic acid
SITE                    24
                        note = Lysine modified with Gamma-glutamic acid-C20 diacid
                         via the side chain
SITE                    37
                        note = (2S,4R)-4-hydroxypyrrolidine-2-carboxamide
SEQUENCE: 187
XCNTATCATQ RLADFLRHSS NNLKPILPPT NVGSNTX                           37

SEQ ID NO: 188          moltype = AA  length = 37
FEATURE                 Location/Qualifiers
source                  1..37
                        mol_type = protein
                        organism = synthetic construct
SITE                    1
                        note = (S)-2,5-diaminopentanoic acid
SITE                    24
                        note = Lysine modified with Gamma-glutamic acid-C20 diacid
                         via the side chain
SITE                    37
                        note = (2S,4R)-4-hydroxypyrrolidine-2-carboxamide
SEQUENCE: 188
XCNTATCATQ RLADFLRHSS NNLKPILPPT NVGSNTX                           37

SEQ ID NO: 189          moltype = AA  length = 37
FEATURE                 Location/Qualifiers
source                  1..37
                        mol_type = protein
                        organism = synthetic construct
SITE                    24
                        note = Lysine modified with Gamma-glutamic acid-C20 diacid
                         via the side chain
SITE                    37
                        note = (2S,4R)-4-hydroxypyrrolidine-2-carboxamide
SEQUENCE: 189
KCNTATCATQ RLADFLRHSS NNLKPILPPT NVGSNTX                           37

SEQ ID NO: 190          moltype = AA  length = 37
FEATURE                 Location/Qualifiers
source                  1..37
                        mol_type = protein
                        organism = synthetic construct
SITE                    1
                        note = (2S)-2-amino-6-(diaminomethylideneamino)hexanoic acid
SITE                    24
                        note = Lysine modified with Gamma-glutamic acid-C20 diacid
```

```
                         via the side chain
SITE                     37
                         note = (2S,4R)-4-hydroxypyrrolidine-2-carboxamide
SEQUENCE: 190
XCNTATCATQ RLADFLRHSS NNLKPILPPT NVGSNTX                       37

SEQ ID NO: 191           moltype = AA  length = 37
FEATURE                  Location/Qualifiers
source                   1..37
                         mol_type = protein
                         organism = synthetic construct
SITE                     24
                         note = Lysine modified with Gamma-glutamic acid-C20 diacid
                          via the side chain
SITE                     37
                         note = (2S,4R)-4-hydroxypyrrolidine-2-carboxamide
SEQUENCE: 191
HCNTATCATQ RLADFLRHSS NNLKPILPPT NVGSNTX                       37

SEQ ID NO: 192           moltype = AA  length = 37
FEATURE                  Location/Qualifiers
source                   1..37
                         mol_type = protein
                         organism = synthetic construct
SITE                     24
                         note = Lysine modified with Gamma-glutamic acid-C20 diacid
                          via the side chain
SITE                     37
                         note = (2S,4R)-4-hydroxypyrrolidine-2-carboxamide
SEQUENCE: 192
DCNTATCATQ RLADFLRHSS NNLKPILPPT NVGSNTX                       37

SEQ ID NO: 193           moltype = AA  length = 37
FEATURE                  Location/Qualifiers
source                   1..37
                         mol_type = protein
                         organism = synthetic construct
SITE                     24
                         note = Lysine modified with Gamma-glutamic acid-C20 diacid
                          via the side chain
SITE                     37
                         note = (2S,4R)-4-hydroxypyrrolidine-2-carboxamide
SEQUENCE: 193
ECNTATCATQ RLADFLRHSS NNLKPILPPT NVGSNTX                       37

SEQ ID NO: 194           moltype = AA  length = 37
FEATURE                  Location/Qualifiers
source                   1..37
                         mol_type = protein
                         organism = synthetic construct
SITE                     24
                         note = Lysine modified with
                          (2-(2-(2-aminoethoxy)ethoxy)acetic acid)2-Gamma-glutamic
                          acid-C20 diacid via the side chain
SITE                     37
                         note = (2S,4R)-4-hydroxypyrrolidine-2-carboxamide
SEQUENCE: 194
RCNTATCATQ RLADFLRHSS NNLKPILPPT NVGSNTX                       37

SEQ ID NO: 195           moltype = AA  length = 37
FEATURE                  Location/Qualifiers
source                   1..37
                         mol_type = protein
                         organism = synthetic construct
SITE                     23
                         note = Lysine modified with Gamma-glutamic acid-C20 diacid
                          via the side chain
SITE                     37
                         note = (2S,4R)-4-hydroxypyrrolidine-2-carboxamide
SEQUENCE: 195
RCNTATCATQ RLADFLRHSS NNKGPILPPT NVGSNTX                       37

SEQ ID NO: 196           moltype = AA  length = 37
FEATURE                  Location/Qualifiers
source                   1..37
                         mol_type = protein
                         organism = synthetic construct
SITE                     23
                         note = Lysine modified with
```

```
                        (2-(2-(2-aminoethoxy)ethoxy)acetic acid)2-Gamma-glutamic
                        acid-C20 diacid via the side chain
SITE                    37
                        note = (2S,4R)-4-hydroxypyrrolidine-2-carboxamide
SEQUENCE: 196
RCNTATCATQ RLADFLRHSS NNKGPILPPT NVGSNTX                           37

SEQ ID NO: 197          moltype = AA  length = 37
FEATURE                 Location/Qualifiers
source                  1..37
                        mol_type = protein
                        organism = synthetic construct
SITE                    23
                        note = Lysine modified with Gamma-glutamic acid-C18 diacid
                        via the side chain
SITE                    37
                        note = (2S,4R)-4-hydroxypyrrolidine-2-carboxamide
SEQUENCE: 197
RCNTATCATQ RLADFLRHSS NNKGPILPPT NVGSNTX                           37

SEQ ID NO: 198          moltype = AA  length = 37
FEATURE                 Location/Qualifiers
source                  1..37
                        mol_type = protein
                        organism = synthetic construct
SITE                    23
                        note = Lysine modified with
                        (2-(2-(2-aminoethoxy)ethoxy)acetic acid)2-Gamma-glutamic
                        acid-C18 diacid via the side chain
SITE                    37
                        note = (2S,4R)-4-hydroxypyrrolidine-2-carboxamide
SEQUENCE: 198
RCNTATCATQ RLADFLRHSS NNKGPILPPT NVGSNTX                           37

SEQ ID NO: 199          moltype = AA  length = 37
FEATURE                 Location/Qualifiers
source                  1..37
                        mol_type = protein
                        organism = synthetic construct
SITE                    22
                        note = Lysine modified with Gamma-glutamic acid-C20 diacid
                        via the side chain
SITE                    37
                        note = (2S,4R)-4-hydroxypyrrolidine-2-carboxamide
SEQUENCE: 199
RCNTATCATQ RLADFLRHSS NKLGPILPPT NVGSNTX                           37

SEQ ID NO: 200          moltype = AA  length = 37
FEATURE                 Location/Qualifiers
source                  1..37
                        mol_type = protein
                        organism = synthetic construct
SITE                    22
                        note = Lysine modified with
                        (2-(2-(2-aminoethoxy)ethoxy)acetic acid)2-Gamma-glutamic
                        acid-C20 diacid via the side chain
SITE                    37
                        note = (2S,4R)-4-hydroxypyrrolidine-2-carboxamide
SEQUENCE: 200
RCNTATCATQ RLADFLRHSS NKLGPILPPT NVGSNTX                           37

SEQ ID NO: 201          moltype = AA  length = 37
FEATURE                 Location/Qualifiers
source                  1..37
                        mol_type = protein
                        organism = synthetic construct
SITE                    22
                        note = Lysine modified with Gamma-glutamic acid-C18 diacid
                        via the side chain
SITE                    37
                        note = (2S,4R)-4-hydroxypyrrolidine-2-carboxamide
SEQUENCE: 201
RCNTATCATQ RLADFLRHSS NKLGPILPPT NVGSNTX                           37

SEQ ID NO: 202          moltype = AA  length = 37
FEATURE                 Location/Qualifiers
source                  1..37
                        mol_type = protein
                        organism = synthetic construct
```

-continued

```
SITE                    22
                        note = Lysine modified with
                         (2-(2-(2-aminoethoxy)ethoxy)acetic acid)2-Gamma-glutamic
                         acid-C18 diacid via the side chain
SITE                    37
                        note = (2S,4R)-4-hydroxypyrrolidine-2-carboxamide
SEQUENCE: 202
RCNTATCATQ RLADFLRHSS NKLGPILPPT NVGSNTX                           37

SEQ ID NO: 203          moltype = AA  length = 37
FEATURE                 Location/Qualifiers
source                  1..37
                        mol_type = protein
                        organism = synthetic construct
SITE                    21
                        note = Lysine modified with Gamma-glutamic acid-C20 diacid
                         via the side chain
SITE                    37
                        note = (2S,4R)-4-hydroxypyrrolidine-2-carboxamide
SEQUENCE: 203
RCNTATCATQ RLADFLRHSS KNLGPILPPT NVGSNTX                           37

SEQ ID NO: 204          moltype = AA  length = 37
FEATURE                 Location/Qualifiers
source                  1..37
                        mol_type = protein
                        organism = synthetic construct
SITE                    21
                        note = Lysine modified with
                         (2-(2-(2-aminoethoxy)ethoxy)acetic acid)2-Gamma-glutamic
                         acid-C20 diacid via the side chain
SITE                    37
                        note = (2S,4R)-4-hydroxypyrrolidine-2-carboxamide
SEQUENCE: 204
RCNTATCATQ RLADFLRHSS KNLGPILPPT NVGSNTX                           37

SEQ ID NO: 205          moltype = AA  length = 37
FEATURE                 Location/Qualifiers
source                  1..37
                        mol_type = protein
                        organism = synthetic construct
SITE                    21
                        note = Lysine modified with Gamma-glutamic acid-C18 diacid
                         via the side chain
SITE                    37
                        note = (2S,4R)-4-hydroxypyrrolidine-2-carboxamide
SEQUENCE: 205
RCNTATCATQ RLADFLRHSS KNLGPILPPT NVGSNTX                           37

SEQ ID NO: 206          moltype = AA  length = 37
FEATURE                 Location/Qualifiers
source                  1..37
                        mol_type = protein
                        organism = synthetic construct
SITE                    21
                        note = Lysine modified with
                         (2-(2-(2-aminoethoxy)ethoxy)acetic acid)2-Gamma-glutamic
                         acid-C18 diacid via the side chain
SITE                    37
                        note = (2S,4R)-4-hydroxypyrrolidine-2-carboxamide
SEQUENCE: 206
RCNTATCATQ RLADFLRHSS KNLGPILPPT NVGSNTX                           37

SEQ ID NO: 207          moltype = AA  length = 37
FEATURE                 Location/Qualifiers
source                  1..37
                        mol_type = protein
                        organism = synthetic construct
SITE                    20
                        note = Lysine modified with Gamma-glutamic acid-C20 diacid
                         via the side chain
SITE                    37
                        note = (2S,4R)-4-hydroxypyrrolidine-2-carboxamide
SEQUENCE: 207
RCNTATCATQ RLADFLRHSK NNLGPILPPT NVGSNTX                           37

SEQ ID NO: 208          moltype = AA  length = 37
FEATURE                 Location/Qualifiers
source                  1..37
```

```
                        mol_type = protein
                        organism = synthetic construct
SITE                    20
                        note = Lysine modified with
                         (2-(2-(2-aminoethoxy)ethoxy)acetic acid)2-Gamma-glutamic
                         acid-C20 diacid via the side chain
SITE                    37
                        note = (2S,4R)-4-hydroxypyrrolidine-2-carboxamide
SEQUENCE: 208
RCNTATCATQ RLADFLRHSK NNLGPILPPT NVGSNTX                            37

SEQ ID NO: 209          moltype = AA  length = 37
FEATURE                 Location/Qualifiers
source                  1..37
                        mol_type = protein
                        organism = synthetic construct
SITE                    20
                        note = Lysine modified with Gamma-glutamic acid-C18 diacid
                         via the side chain
SITE                    37
                        note = (2S,4R)-4-hydroxypyrrolidine-2-carboxamide
SEQUENCE: 209
RCNTATCATQ RLADFLRHSK NNLGPILPPT NVGSNTX                            37

SEQ ID NO: 210          moltype = AA  length = 37
FEATURE                 Location/Qualifiers
source                  1..37
                        mol_type = protein
                        organism = synthetic construct
SITE                    20
                        note = Lysine modified with
                         (2-(2-(2-aminoethoxy)ethoxy)acetic acid)2-Gamma-glutamic
                         acid-C18 diacid via the side chain
SITE                    37
                        note = (2S,4R)-4-hydroxypyrrolidine-2-carboxamide
SEQUENCE: 210
RCNTATCATQ RLADFLRHSK NNLGPILPPT NVGSNTX                            37

SEQ ID NO: 211          moltype = AA  length = 37
FEATURE                 Location/Qualifiers
source                  1..37
                        mol_type = protein
                        organism = synthetic construct
SITE                    19
                        note = Lysine modified with Gamma-glutamic acid-C20 diacid
                         via the side chain
SITE                    37
                        note = (2S,4R)-4-hydroxypyrrolidine-2-carboxamide
SEQUENCE: 211
RCNTATCATQ RLADFLRHKS NNLGPILPPT NVGSNTX                            37

SEQ ID NO: 212          moltype = AA  length = 37
FEATURE                 Location/Qualifiers
source                  1..37
                        mol_type = protein
                        organism = synthetic construct
SITE                    19
                        note = Lysine modified with
                         (2-(2-(2-aminoethoxy)ethoxy)acetic acid)2-Gamma-glutamic
                         acid-C20 diacid via the side chain
SITE                    37
                        note = (2S,4R)-4-hydroxypyrrolidine-2-carboxamide
SEQUENCE: 212
RCNTATCATQ RLADFLRHKS NNLGPILPPT NVGSNTX                            37

SEQ ID NO: 213          moltype = AA  length = 37
FEATURE                 Location/Qualifiers
source                  1..37
                        mol_type = protein
                        organism = synthetic construct
SITE                    19
                        note = Lysine modified with Gamma-glutamic acid-C18 diacid
                         via the side chain
SITE                    37
                        note = (2S,4R)-4-hydroxypyrrolidine-2-carboxamide
SEQUENCE: 213
RCNTATCATQ RLADFLRHKS NNLGPILPPT NVGSNTX                            37

SEQ ID NO: 214          moltype = AA  length = 37
```

-continued

```
FEATURE                Location/Qualifiers
source                 1..37
                       mol_type = protein
                       organism = synthetic construct
SITE                   19
                       note = Lysine modified with
                        (2-(2-(2-aminoethoxy)ethoxy)acetic acid)2-Gamma-glutamic
                        acid-C18 diacid via the side chain
SITE                   37
                       note = (2S,4R)-4-hydroxypyrrolidine-2-carboxamide
SEQUENCE: 214
RCNTATCATQ RLADFLRHKS NNLGPILPPT NVGSNTX                           37

SEQ ID NO: 215         moltype = AA  length = 37
FEATURE                Location/Qualifiers
source                 1..37
                       mol_type = protein
                       organism = synthetic construct
SITE                   25
                       note = Lysine modified with Gamma-glutamic acid-C20 diacid
                        via the side chain
SITE                   37
                       note = (2S,4R)-4-hydroxypyrrolidine-2-carboxamide
SEQUENCE: 215
RCNTATCATQ RLADFLRHSS NNLGKILPPT NVGSNTX                           37

SEQ ID NO: 216         moltype = AA  length = 37
FEATURE                Location/Qualifiers
source                 1..37
                       mol_type = protein
                       organism = synthetic construct
SITE                   25
                       note = Lysine modified with
                        (2-(2-(2-aminoethoxy)ethoxy)acetic acid)2-Gamma-glutamic
                        acid-C20 diacid via the side chain
SITE                   37
                       note = (2S,4R)-4-hydroxypyrrolidine-2-carboxamide
SEQUENCE: 216
RCNTATCATQ RLADFLRHSS NNLGKILPPT NVGSNTX                           37

SEQ ID NO: 217         moltype = AA  length = 37
FEATURE                Location/Qualifiers
source                 1..37
                       mol_type = protein
                       organism = synthetic construct
SITE                   25
                       note = Lysine modified with Gamma-glutamic acid-C18 diacid
                        via the side chain
SITE                   37
                       note = (2S,4R)-4-hydroxypyrrolidine-2-carboxamide
SEQUENCE: 217
RCNTATCATQ RLADFLRHSS NNLGKILPPT NVGSNTX                           37

SEQ ID NO: 218         moltype = AA  length = 37
FEATURE                Location/Qualifiers
source                 1..37
                       mol_type = protein
                       organism = synthetic construct
SITE                   25
                       note = Lysine modified with
                        (2-(2-(2-aminoethoxy)ethoxy)acetic acid)2-Gamma-glutamic
                        acid-C18 diacid via the side chain
SITE                   37
                       note = (2S,4R)-4-hydroxypyrrolidine-2-carboxamide
SEQUENCE: 218
RCNTATCATQ RLADFLRHSS NNLGKILPPT NVGSNTX                           37

SEQ ID NO: 219         moltype = AA  length = 37
FEATURE                Location/Qualifiers
source                 1..37
                       mol_type = protein
                       organism = synthetic construct
SITE                   24
                       note = Lysine modified with
                        2-(2-(2-aminoethoxy)ethoxy)acetic acid-Gamma-glutamic
                        acid-C20 diacid via the side chain
SITE                   37
                       note = (2S,4R)-4-hydroxypyrrolidine-2-carboxamide
SEQUENCE: 219
```

-continued

```
RCNTATCATQ RLADFLRHSS NNLKPILPPT NVGSNTX                              37

SEQ ID NO: 220         moltype = AA  length = 37
FEATURE                Location/Qualifiers
source                 1..37
                       mol_type = protein
                       organism = synthetic construct
SITE                   24
                       note = Lysine modified with Gamma-glutamic acid-C18 diacid
                        via the side chain
SITE                   37
                       note = (2S,4R)-4-hydroxypyrrolidine-2-carboxamide
SEQUENCE: 220
RCNTATCATQ RLADFLRHSS NNLKPILPPT NVGSNTX                              37

SEQ ID NO: 221         moltype = AA  length = 37
FEATURE                Location/Qualifiers
source                 1..37
                       mol_type = protein
                       organism = synthetic construct
SITE                   24
                       note = Lysine modified with
                        2-(2-(2-aminoethoxy)ethoxy)acetic acid-Gamma-glutamic
                        acid-C18 diacid via the side chain
SITE                   37
                       note = (2S,4R)-4-hydroxypyrrolidine-2-carboxamide
SEQUENCE: 221
RCNTATCATQ RLADFLRHSS NNLKPILPPT NVGSNTX                              37

SEQ ID NO: 222         moltype = AA  length = 37
FEATURE                Location/Qualifiers
source                 1..37
                       mol_type = protein
                       organism = synthetic construct
SITE                   24
                       note = Lysine modified with
                        (2-(2-(2-aminoethoxy)ethoxy)acetic acid)2-Gamma-glutamic
                        acid-C18 diacid via the side chain
SITE                   37
                       note = (2S,4R)-4-hydroxypyrrolidine-2-carboxamide
SEQUENCE: 222
RCNTATCATQ RLADFLRHSS NNLKPILPPT NVGSNTX                              37

SEQ ID NO: 223         moltype = AA  length = 37
FEATURE                Location/Qualifiers
source                 1..37
                       mol_type = protein
                       organism = synthetic construct
SITE                   23
                       note = Lysine modified with
                        2-(2-(2-aminoethoxy)ethoxy)acetic acid-Gamma-glutamic
                        acid-C20 diacid via the side chain
SITE                   37
                       note = (2S,4R)-4-hydroxypyrrolidine-2-carboxamide
SEQUENCE: 223
RCNTATCATQ RLADFLRHSS NNKGPILPPT NVGSNTX                              37

SEQ ID NO: 224         moltype = AA  length = 37
FEATURE                Location/Qualifiers
source                 1..37
                       mol_type = protein
                       organism = synthetic construct
SITE                   23
                       note = Lysine modified with
                        2-(2-(2-aminoethoxy)ethoxy)acetic acid-Gamma-glutamic
                        acid-C18 diacid via the side chain
SITE                   37
                       note = (2S,4R)-4-hydroxypyrrolidine-2-carboxamide
SEQUENCE: 224
RCNTATCATQ RLADFLRHSS NNKGPILPPT NVGSNTX                              37

SEQ ID NO: 225         moltype = AA  length = 37
FEATURE                Location/Qualifiers
source                 1..37
                       mol_type = protein
                       organism = synthetic construct
SITE                   22
                       note = Lysine modified with
                        2-(2-(2-aminoethoxy)ethoxy)acetic acid-Gamma-glutamic
```

```
                         acid-C20 diacid via the side chain
SITE                    37
                        note = (2S,4R)-4-hydroxypyrrolidine-2-carboxamide
SEQUENCE: 225
RCNTATCATQ RLADFLRHSS NKLGPILPPT NVGSNTX                             37

SEQ ID NO: 226          moltype = AA  length = 37
FEATURE                 Location/Qualifiers
source                  1..37
                        mol_type = protein
                        organism = synthetic construct
SITE                    22
                        note = Lysine modified with
                         2-(2-(2-aminoethoxy)ethoxy)acetic acid-Gamma-glutamic
                         acid-C18 diacid via the side chain
SITE                    37
                        note = (2S,4R)-4-hydroxypyrrolidine-2-carboxamide
SEQUENCE: 226
RCNTATCATQ RLADFLRHSS NKLGPILPPT NVGSNTX                             37

SEQ ID NO: 227          moltype = AA  length = 37
FEATURE                 Location/Qualifiers
source                  1..37
                        mol_type = protein
                        organism = synthetic construct
SITE                    21
                        note = Lysine modified with
                         2-(2-(2-aminoethoxy)ethoxy)acetic acid-Gamma-glutamic
                         acid-C20 diacid via the side chain
SITE                    37
                        note = (2S,4R)-4-hydroxypyrrolidine-2-carboxamide
SEQUENCE: 227
RCNTATCATQ RLADFLRHSS KNLGPILPPT NVGSNTX                             37

SEQ ID NO: 228          moltype = AA  length = 37
FEATURE                 Location/Qualifiers
source                  1..37
                        mol_type = protein
                        organism = synthetic construct
SITE                    21
                        note = Lysine modified with
                         2-(2-(2-aminoethoxy)ethoxy)acetic acid-Gamma-glutamic
                         acid-C18 diacid via the side chain
SITE                    37
                        note = (2S,4R)-4-hydroxypyrrolidine-2-carboxamide
SEQUENCE: 228
RCNTATCATQ RLADFLRHSS KNLGPILPPT NVGSNTX                             37

SEQ ID NO: 229          moltype = AA  length = 37
FEATURE                 Location/Qualifiers
source                  1..37
                        mol_type = protein
                        organism = synthetic construct
SITE                    20
                        note = Lysine modified with
                         2-(2-(2-aminoethoxy)ethoxy)acetic acid-Gamma-glutamic
                         acid-C20 diacid via the side chain
SITE                    37
                        note = (2S,4R)-4-hydroxypyrrolidine-2-carboxamide
SEQUENCE: 229
RCNTATCATQ RLADFLRHSK NNLGPILPPT NVGSNTX                             37

SEQ ID NO: 230          moltype = AA  length = 37
FEATURE                 Location/Qualifiers
source                  1..37
                        mol_type = protein
                        organism = synthetic construct
SITE                    20
                        note = Lysine modified with
                         2-(2-(2-aminoethoxy)ethoxy)acetic acid-Gamma-glutamic
                         acid-C18 diacid via the side chain
SITE                    37
                        note = (2S,4R)-4-hydroxypyrrolidine-2-carboxamide
SEQUENCE: 230
RCNTATCATQ RLADFLRHSK NNLGPILPPT NVGSNTX                             37

SEQ ID NO: 231          moltype = AA  length = 37
FEATURE                 Location/Qualifiers
source                  1..37
```

-continued

```
                         mol_type = protein
                         organism = synthetic construct
SITE                     19
                         note = Lysine modified with
                          2-(2-(2-aminoethoxy)ethoxy)acetic acid-Gamma-glutamic
                          acid-C20 diacid via the side chain
SITE                     37
                         note = (2S,4R)-4-hydroxypyrrolidine-2-carboxamide
SEQUENCE: 231
RCNTATCATQ RLADFLRHKS NNLGPILPPT NVGSNTX                             37

SEQ ID NO: 232           moltype = AA  length = 37
FEATURE                  Location/Qualifiers
source                   1..37
                         mol_type = protein
                         organism = synthetic construct
SITE                     19
                         note = Lysine modified with
                          2-(2-(2-aminoethoxy)ethoxy)acetic acid-Gamma-glutamic
                          acid-C18 diacid via the side chain
SITE                     37
                         note = (2S,4R)-4-hydroxypyrrolidine-2-carboxamide
SEQUENCE: 232
RCNTATCATQ RLADFLRHKS NNLGPILPPT NVGSNTX                             37

SEQ ID NO: 233           moltype = AA  length = 37
FEATURE                  Location/Qualifiers
source                   1..37
                         mol_type = protein
                         organism = synthetic construct
SITE                     25
                         note = Lysine modified with
                          2-(2-(2-aminoethoxy)ethoxy)acetic acid-Gamma-glutamic
                          acid-C20 diacid via the side chain
SITE                     37
                         note = (2S,4R)-4-hydroxypyrrolidine-2-carboxamide
SEQUENCE: 233
RCNTATCATQ RLADFLRHSS NNLGKILPPT NVGSNTX                             37

SEQ ID NO: 234           moltype = AA  length = 37
FEATURE                  Location/Qualifiers
source                   1..37
                         mol_type = protein
                         organism = synthetic construct
SITE                     25
                         note = Lysine modified with
                          2-(2-(2-aminoethoxy)ethoxy)acetic acid-Gamma-glutamic
                          acid-C18 diacid via the side chain
SITE                     37
                         note = (2S,4R)-4-hydroxypyrrolidine-2-carboxamide
SEQUENCE: 234
RCNTATCATQ RLADFLRHSS NNLGKILPPT NVGSNTX                             37

SEQ ID NO: 235           moltype = AA  length = 37
FEATURE                  Location/Qualifiers
source                   1..37
                         mol_type = protein
                         organism = synthetic construct
SITE                     37
                         note = (2S,4R)-4-hydroxypyrrolidine-2-carboxamide
SEQUENCE: 235
KCNTATCATQ RLADFLRHSS NNLGPILPPT NVGSNTX                             37

SEQ ID NO: 236           moltype = AA  length = 37
FEATURE                  Location/Qualifiers
source                   1..37
                         mol_type = protein
                         organism = synthetic construct
SITE                     37
                         note = (2S,4R)-4-hydroxypyrrolidine-2-carboxamide
SEQUENCE: 236
KCNTATCATQ RLADFLRHSS NNLGPILPPT NVGSNTX                             37

SEQ ID NO: 237           moltype = AA  length = 37
FEATURE                  Location/Qualifiers
source                   1..37
                         mol_type = protein
                         organism = synthetic construct
SITE                     37
```

```
                        note = (2S,4R)-4-hydroxypyrrolidine-2-carboxamide
SEQUENCE: 237
KCNTATCATQ RLADFLRHSS NNLGPILPPT NVGSNTX                           37

SEQ ID NO: 238          moltype = AA  length = 37
FEATURE                 Location/Qualifiers
source                  1..37
                        mol_type = protein
                        organism = synthetic construct
SITE                    37
                        note = (2S,4R)-4-hydroxypyrrolidine-2-carboxamide
SEQUENCE: 238
KCNTATCATQ RLADFLRHSS NNLGPILPPT NVGSNTX                           37

SEQ ID NO: 239          moltype = AA  length = 37
FEATURE                 Location/Qualifiers
source                  1..37
                        mol_type = protein
                        organism = synthetic construct
SITE                    37
                        note = (2S,4R)-4-hydroxypyrrolidine-2-carboxamide
SEQUENCE: 239
KCNTATCATQ RLADFLRHSS NNLGPILPPT NVGSNTX                           37

SEQ ID NO: 240          moltype = AA  length = 37
FEATURE                 Location/Qualifiers
source                  1..37
                        mol_type = protein
                        organism = synthetic construct
SITE                    37
                        note = (2S,4R)-4-hydroxypyrrolidine-2-carboxamide
SEQUENCE: 240
RCNTATCATQ RLADFLRHSS NNLGPILPPT NVGSNTX                           37

SEQ ID NO: 241          moltype = AA  length = 37
FEATURE                 Location/Qualifiers
source                  1..37
                        mol_type = protein
                        organism = synthetic construct
SITE                    37
                        note = (2S,4R)-4-hydroxypyrrolidine-2-carboxamide
SEQUENCE: 241
HCNTATCATQ RLADFLRHSS NNLGPILPPT NVGSNTX                           37

SEQ ID NO: 242          moltype = AA  length = 37
FEATURE                 Location/Qualifiers
source                  1..37
                        mol_type = protein
                        organism = synthetic construct
SITE                    37
                        note = (2S,4R)-4-hydroxypyrrolidine-2-carboxamide
SEQUENCE: 242
KCNTATCATQ RLADFLRHSS NNLGPILPPT NVGSNTX                           37

SEQ ID NO: 243          moltype = AA  length = 37
FEATURE                 Location/Qualifiers
source                  1..37
                        mol_type = protein
                        organism = synthetic construct
SITE                    37
                        note = (2S,4R)-4-hydroxypyrrolidine-2-carboxamide
SEQUENCE: 243
KCNTATCATQ RLADFLRHSS NNLGPILPPT NVGSNTX                           37

SEQ ID NO: 244          moltype = AA  length = 37
FEATURE                 Location/Qualifiers
source                  1..37
                        mol_type = protein
                        organism = synthetic construct
SITE                    37
                        note = (2S,4R)-4-hydroxypyrrolidine-2-carboxamide
SEQUENCE: 244
KCNTATCATQ RLADFLRHSS NNLGPILPPT NVGSNTX                           37

SEQ ID NO: 245          moltype = AA  length = 37
FEATURE                 Location/Qualifiers
source                  1..37
                        mol_type = protein
                        organism = synthetic construct
```

-continued

```
SITE                    37
                        note = (2S,4R)-4-hydroxypyrrolidine-2-carboxamide
SEQUENCE: 245
KCNTATCATQ RLADFLRHSS NNLGPILPPT NVGSNTX                        37

SEQ ID NO: 246          moltype = AA  length = 37
FEATURE                 Location/Qualifiers
source                  1..37
                        mol_type = protein
                        organism = synthetic construct
SITE                    37
                        note = (2S,4R)-4-hydroxypyrrolidine-2-carboxamide
SEQUENCE: 246
KCNTATCATQ RLADFLRHSS NNLGPILPPT NVGSNTX                        37

SEQ ID NO: 247          moltype = AA  length = 37
FEATURE                 Location/Qualifiers
source                  1..37
                        mol_type = protein
                        organism = synthetic construct
SITE                    37
                        note = (2S,4R)-4-hydroxypyrrolidine-2-carboxamide
SEQUENCE: 247
KCNTATCATQ RLADFLRHSS NNLGPILPPT NVGSNTX                        37

SEQ ID NO: 248          moltype = AA  length = 37
FEATURE                 Location/Qualifiers
source                  1..37
                        mol_type = protein
                        organism = synthetic construct
SITE                    1
                        note = Lysine modified with Gamma-glutamic acid-C10 diacid
                         via the side chain
SITE                    37
                        note = (2S,4R)-4-hydroxypyrrolidine-2-carboxamide
SEQUENCE: 248
KCNTATCATQ RLADFLRHSS NNLGPILPPT NVGSNTX                        37

SEQ ID NO: 249          moltype = AA  length = 37
FEATURE                 Location/Qualifiers
source                  1..37
                        mol_type = protein
                        organism = synthetic construct
SITE                    1
                        note = Lysine modified with Gamma-glutamic acid-C12 diacid
                         via the side chain
SITE                    37
                        note = (2S,4R)-4-hydroxypyrrolidine-2-carboxamide
SEQUENCE: 249
KCNTATCATQ RLADFLRHSS NNLGPILPPT NVGSNTX                        37

SEQ ID NO: 250          moltype = AA  length = 37
FEATURE                 Location/Qualifiers
source                  1..37
                        mol_type = protein
                        organism = synthetic construct
SITE                    1
                        note = Lysine modified with Gamma-glutamic acid-C14 diacid
                         via the side chain
SITE                    37
                        note = (2S,4R)-4-hydroxypyrrolidine-2-carboxamide
SEQUENCE: 250
KCNTATCATQ RLADFLRHSS NNLGPILPPT NVGSNTX                        37

SEQ ID NO: 251          moltype = AA  length = 37
FEATURE                 Location/Qualifiers
source                  1..37
                        mol_type = protein
                        organism = synthetic construct
SITE                    1
                        note = Lysine modified with Gamma-glutamic acid-C16 diacid
                         via the side chain
SITE                    37
                        note = (2S,4R)-4-hydroxypyrrolidine-2-carboxamide
SEQUENCE: 251
KCNTATCATQ RLADFLRHSS NNLGPILPPT NVGSNTX                        37

SEQ ID NO: 252          moltype = AA  length = 37
FEATURE                 Location/Qualifiers
```

-continued

```
source                1..37
                      mol_type = protein
                      organism = synthetic construct
SITE                  1
                      note = Lysine modified with Gamma-glutamic acid-C18 diacid
                       via the side chain
SITE                  37
                      note = (2S,4R)-4-hydroxypyrrolidine-2-carboxamide
SEQUENCE: 252
KCNTATCATQ RLADFLRHSS NNLGPILPPT NVGSNTX                      37

SEQ ID NO: 253        moltype = AA  length = 37
FEATURE               Location/Qualifiers
source                1..37
                      mol_type = protein
                      organism = synthetic construct
SITE                  37
                      note = (2S,4R)-4-hydroxypyrrolidine-2-carboxamide
SEQUENCE: 253
RCNTATCATQ RLADFLRHSS NNLKPILPPT NVGSNTX                      37

SEQ ID NO: 254        moltype = AA  length = 37
FEATURE               Location/Qualifiers
source                1..37
                      mol_type = protein
                      organism = synthetic construct
SITE                  37
                      note = (2S,4R)-4-hydroxypyrrolidine-2-carboxamide
SEQUENCE: 254
HCNTATCATQ RLADFLRHSS NNLKPILPPT NVGSNTX                      37

SEQ ID NO: 255        moltype = AA  length = 37
FEATURE               Location/Qualifiers
source                1..37
                      mol_type = protein
                      organism = synthetic construct
SITE                  37
                      note = (2S,4R)-4-hydroxypyrrolidine-2-carboxamide
SEQUENCE: 255
KCNTATCATQ RLADFLRHSS NNLKPILPPT NVGSNTX                      37

SEQ ID NO: 256        moltype = AA  length = 37
FEATURE               Location/Qualifiers
source                1..37
                      mol_type = protein
                      organism = synthetic construct
SITE                  37
                      note = (2S,4R)-4-hydroxypyrrolidine-2-carboxamide
SEQUENCE: 256
KCNTATCATQ RLADFLRHSS NNLKPILPPT NVGSNTX                      37

SEQ ID NO: 257        moltype = AA  length = 37
FEATURE               Location/Qualifiers
source                1..37
                      mol_type = protein
                      organism = synthetic construct
SITE                  37
                      note = (2S,4R)-4-hydroxypyrrolidine-2-carboxamide
SEQUENCE: 257
KCNTATCATQ RLADFLRHSS NNLKPILPPT NVGSNTX                      37

SEQ ID NO: 258        moltype = AA  length = 37
FEATURE               Location/Qualifiers
source                1..37
                      mol_type = protein
                      organism = synthetic construct
SITE                  37
                      note = (2S,4R)-4-hydroxypyrrolidine-2-carboxamide
SEQUENCE: 258
KCNTATCATQ RLADFLRHSS NNLKPILPPT NVGSNTX                      37

SEQ ID NO: 259        moltype = AA  length = 37
FEATURE               Location/Qualifiers
source                1..37
                      mol_type = protein
                      organism = synthetic construct
SITE                  37
                      note = (2S,4R)-4-hydroxypyrrolidine-2-carboxamide
SEQUENCE: 259
```

```
KCNTATCATQ RLADFLRHSS NNLKPILPPT NVGSNTX                          37

SEQ ID NO: 260          moltype = AA  length = 37
FEATURE                 Location/Qualifiers
source                  1..37
                        mol_type = protein
                        organism = synthetic construct
SITE                    37
                        note = (2S,4R)-4-hydroxypyrrolidine-2-carboxamide
SEQUENCE: 260
KCNTATCATQ RLADFLRHSS NNLKPILPPT NVGSNTX                          37

SEQ ID NO: 261          moltype = AA  length = 37
FEATURE                 Location/Qualifiers
source                  1..37
                        mol_type = protein
                        organism = synthetic construct
SITE                    1
                        note = Lysine modified with Gamma-glutamic acid-C10 diacid
                         via the side chain
SITE                    37
                        note = (2S,4R)-4-hydroxypyrrolidine-2-carboxamide
SEQUENCE: 261
KCNTATCATQ RLADFLRHSS NNLKPILPPT NVGSNTX                          37

SEQ ID NO: 262          moltype = AA  length = 37
FEATURE                 Location/Qualifiers
source                  1..37
                        mol_type = protein
                        organism = synthetic construct
SITE                    1
                        note = Lysine modified with Gamma-glutamic acid-C12 diacid
                         via the side chain
SITE                    37
                        note = (2S,4R)-4-hydroxypyrrolidine-2-carboxamide
SEQUENCE: 262
KCNTATCATQ RLADFLRHSS NNLKPILPPT NVGSNTX                          37

SEQ ID NO: 263          moltype = AA  length = 37
FEATURE                 Location/Qualifiers
source                  1..37
                        mol_type = protein
                        organism = synthetic construct
SITE                    1
                        note = Lysine modified with Gamma-glutamic acid-C14 diacid
                         via the side chain
SITE                    37
                        note = (2S,4R)-4-hydroxypyrrolidine-2-carboxamide
SEQUENCE: 263
KCNTATCATQ RLADFLRHSS NNLKPILPPT NVGSNTX                          37

SEQ ID NO: 264          moltype = AA  length = 37
FEATURE                 Location/Qualifiers
source                  1..37
                        mol_type = protein
                        organism = synthetic construct
SITE                    1
                        note = Lysine modified with Gamma-glutamic acid-C16 diacid
                         via the side chain
SITE                    37
                        note = (2S,4R)-4-hydroxypyrrolidine-2-carboxamide
SEQUENCE: 264
KCNTATCATQ RLADFLRHSS NNLKPILPPT NVGSNTX                          37

SEQ ID NO: 265          moltype = AA  length = 37
FEATURE                 Location/Qualifiers
source                  1..37
                        mol_type = protein
                        organism = synthetic construct
SITE                    1
                        note = Lysine modified with Gamma-glutamic acid-C18 diacid
                         via the side chain
SITE                    37
                        note = (2S,4R)-4-hydroxypyrrolidine-2-carboxamide
SEQUENCE: 265
KCNTATCATQ RLADFLRHSS NNLKPILPPT NVGSNTX                          37

SEQ ID NO: 266          moltype = AA  length = 37
FEATURE                 Location/Qualifiers
```

```
source                  1..37
                        mol_type = protein
                        organism = synthetic construct
SITE                    37
                        note = Amidated residue
SEQUENCE: 266
KCNTATCATQ RLANFLVHSS NNFGPILPPT NVGSNTY                    37

SEQ ID NO: 267          moltype = AA  length = 37
FEATURE                 Location/Qualifiers
source                  1..37
                        mol_type = protein
                        organism = synthetic construct
SITE                    37
                        note = (S)-azetidine-2-carboxamide
SEQUENCE: 267
KCNTATCATQ RLADFLRHSS NNLKPILPPT NVGSNTX                    37

SEQ ID NO: 268          moltype = AA  length = 37
FEATURE                 Location/Qualifiers
source                  1..37
                        mol_type = protein
                        organism = synthetic construct
SITE                    37
                        note = (S)-azetidine-2-carboxamide
SEQUENCE: 268
KCNTATCATQ RLADFLRHSS NNLGPILPPT NVGSNTX                    37

SEQ ID NO: 269          moltype = AA  length = 37
FEATURE                 Location/Qualifiers
source                  1..37
                        mol_type = protein
                        organism = synthetic construct
SITE                    37
                        note = (2S,4R)-4-hydroxypyrrolidine-2-carboxamide
SEQUENCE: 269
KCNTATCATQ RLADFLRHSS NNLRPILPPT NVGSNTX                    37

SEQ ID NO: 270          moltype = AA  length = 37
FEATURE                 Location/Qualifiers
source                  1..37
                        mol_type = protein
                        organism = synthetic construct
SITE                    37
                        note = (2S,4R)-4-hydroxypyrrolidine-2-carboxamide
SEQUENCE: 270
KCNTATCATQ RLADFLRHSS NNLHPILPPT NVGSNTX                    37

SEQ ID NO: 271          moltype = AA  length = 37
FEATURE                 Location/Qualifiers
source                  1..37
                        mol_type = protein
                        organism = synthetic construct
SITE                    37
                        note = Amidated residue
SEQUENCE: 271
KCNTATCATQ RLADFLRHSS NNLKPILPPT NVGSNTP                    37

SEQ ID NO: 272          moltype = AA  length = 37
FEATURE                 Location/Qualifiers
source                  1..37
                        mol_type = protein
                        organism = synthetic construct
SITE                    37
                        note = Amidated residue
SEQUENCE: 272
KCNTATCATQ RLADFLRHSS NNLRPILPPT NVGSNTP                    37

SEQ ID NO: 273          moltype = AA  length = 37
FEATURE                 Location/Qualifiers
source                  1..37
                        mol_type = protein
                        organism = synthetic construct
SITE                    37
                        note = Amidated residue
SEQUENCE: 273
KCNTATCATQ RLADFLRHSS NNLHPILPPT NVGSNTP                    37

SEQ ID NO: 274          moltype = AA  length = 37
```

```
FEATURE                Location/Qualifiers
source                 1..37
                       mol_type = protein
                       organism = synthetic construct
SITE                   37
                       note = Amidated residue
SEQUENCE: 274
KCNTATCATQ RLADFLRHSS NNLPPILPPT NVGSNTP                             37

SEQ ID NO: 275         moltype = AA  length = 37
FEATURE                Location/Qualifiers
source                 1..37
                       mol_type = protein
                       organism = synthetic construct
SITE                   37
                       note = Amidated residue
SEQUENCE: 275
KCNTATCATQ RLADFLRHSS NNLDPILPPT NVGSNTP                             37

SEQ ID NO: 276         moltype = AA  length = 37
FEATURE                Location/Qualifiers
source                 1..37
                       mol_type = protein
                       organism = synthetic construct
SITE                   37
                       note = Amidated residue
SEQUENCE: 276
KCNTATCATQ RLADFLRHSS NNLNPILPPT NVGSNTP                             37

SEQ ID NO: 277         moltype = AA  length = 37
FEATURE                Location/Qualifiers
source                 1..37
                       mol_type = protein
                       organism = synthetic construct
SITE                   37
                       note = Amidated residue
SEQUENCE: 277
KCNTATCATQ RLADFLRHSS NNLSPILPPT NVGSNTP                             37

SEQ ID NO: 278         moltype = AA  length = 37
FEATURE                Location/Qualifiers
source                 1..37
                       mol_type = protein
                       organism = synthetic construct
SITE                   24
                       note = Alpha-L-Lysine
SITE                   37
                       note = Amidated residue
SEQUENCE: 278
KCNTATCATQ RLADFLRHSS NNLXPILPPT NVGSNTP                             37

SEQ ID NO: 279         moltype = AA  length = 37
FEATURE                Location/Qualifiers
source                 1..37
                       mol_type = protein
                       organism = synthetic construct
SITE                   24
                       note = (S)-2,3-diaminopropanoic acid
SITE                   37
                       note = Amidated residue
SEQUENCE: 279
KCNTATCATQ RLADFLRHSS NNLXPILPPT NVGSNTP                             37

SEQ ID NO: 280         moltype = AA  length = 37
FEATURE                Location/Qualifiers
source                 1..37
                       mol_type = protein
                       organism = synthetic construct
SITE                   24
                       note = (S)-2,4-diaminobutanoic acid
SITE                   37
                       note = Amidated residue
SEQUENCE: 280
KCNTATCATQ RLADFLRHSS NNLXPILPPT NVGSNTP                             37

SEQ ID NO: 281         moltype = AA  length = 37
FEATURE                Location/Qualifiers
source                 1..37
                       mol_type = protein
```

```
                         organism = synthetic construct
SITE                     24
                         note = (S)-2,5-diaminopentanoic acid
SITE                     37
                         note = Amidated residue
SEQUENCE: 281
KCNTATCATQ RLADFLRHSS NNLXPILPPT NVGSNTP                           37

SEQ ID NO: 282           moltype = AA  length = 37
FEATURE                  Location/Qualifiers
source                   1..37
                         mol_type = protein
                         organism = synthetic construct
SITE                     24
                         note = (S)-2-amino-5-ureidopentanoic acid
SITE                     37
                         note = Amidated residue
SEQUENCE: 282
KCNTATCATQ RLADFLRHSS NNLXPILPPT NVGSNTP                           37

SEQ ID NO: 283           moltype = AA  length = 37
FEATURE                  Location/Qualifiers
source                   1..37
                         mol_type = protein
                         organism = synthetic construct
SITE                     24
                         note = Sarcosine
SITE                     37
                         note = Amidated residue
SEQUENCE: 283
KCNTATCATQ RLADFLRHSS NNLXPILPPT NVGSNTP                           37

SEQ ID NO: 284           moltype = AA  length = 37
FEATURE                  Location/Qualifiers
source                   1..37
                         mol_type = protein
                         organism = synthetic construct
SITE                     24
                         note = 4-(aminomethyl)cyclohexane-1-carboxylic acid
SITE                     37
                         note = Amidated residue
SEQUENCE: 284
KCNTATCATQ RLADFLRHSS NNLXPILPPT NVGSNTP                           37

SEQ ID NO: 285           moltype = AA  length = 37
FEATURE                  Location/Qualifiers
source                   1..37
                         mol_type = protein
                         organism = synthetic construct
SITE                     24
                         note = 8-Aminooctanoic acid
SITE                     37
                         note = Amidated residue
SEQUENCE: 285
KCNTATCATQ RLADFLRHSS NNLXPILPPT NVGSNTP                           37

SEQ ID NO: 286           moltype = AA  length = 37
FEATURE                  Location/Qualifiers
source                   1..37
                         mol_type = protein
                         organism = synthetic construct
SITE                     37
                         note = (2S,4R)-4-hydroxypyrrolidine-2-carboxamide
SEQUENCE: 286
KCNTATCATQ RLADFLRHSS NNLKPILPPT NVGSNTX                           37

SEQ ID NO: 287           moltype = AA  length = 37
FEATURE                  Location/Qualifiers
source                   1..37
                         mol_type = protein
                         organism = synthetic construct
SITE                     37
                         note = (2S,4R)-4-hydroxypyrrolidine-2-carboxamide
SEQUENCE: 287
KCNTATCATQ RLADFLRHSS NNLKPILPPT NVGSNTX                           37

SEQ ID NO: 288           moltype = AA  length = 37
FEATURE                  Location/Qualifiers
source                   1..37
```

```
                        mol_type = protein
                        organism = synthetic construct
SITE                    37
                        note = (2S,4R)-4-hydroxypyrrolidine-2-carboxamide
SEQUENCE: 288
KCNTATCATQ RLADFLRHSS NNLKPILPPT NVGSNTX                            37

SEQ ID NO: 289          moltype = AA  length = 37
FEATURE                 Location/Qualifiers
source                  1..37
                        mol_type = protein
                        organism = synthetic construct
SITE                    37
                        note = (2S,4R)-4-hydroxypyrrolidine-2-carboxamide
SEQUENCE: 289
KCNTATCATQ RLADFLRHSS NNLKPILPPT NVGSNTX                            37

SEQ ID NO: 290          moltype = AA  length = 37
FEATURE                 Location/Qualifiers
source                  1..37
                        mol_type = protein
                        organism = synthetic construct
SITE                    37
                        note = (2S,4R)-4-hydroxypyrrolidine-2-carboxamide
SEQUENCE: 290
KCNTATCATQ RLADFLRHSS NNLKPILPPT NVGSNTX                            37

SEQ ID NO: 291          moltype = AA  length = 37
FEATURE                 Location/Qualifiers
source                  1..37
                        mol_type = protein
                        organism = synthetic construct
SITE                    37
                        note = (2S,4R)-4-hydroxypyrrolidine-2-carboxamide
SEQUENCE: 291
KCNTATCATQ RLADFLRHSS NNLKPILPPT NVGSNTX                            37

SEQ ID NO: 292          moltype = AA  length = 37
FEATURE                 Location/Qualifiers
source                  1..37
                        mol_type = protein
                        organism = synthetic construct
SITE                    37
                        note = (2S,4R)-4-hydroxypyrrolidine-2-carboxamide
SEQUENCE: 292
KCNTATCATQ RLADFLRHSS NNLKPILPPT NVGSNTX                            37

SEQ ID NO: 293          moltype = AA  length = 37
FEATURE                 Location/Qualifiers
source                  1..37
                        mol_type = protein
                        organism = synthetic construct
SITE                    37
                        note = (2S,4R)-4-hydroxypyrrolidine-2-carboxamide
SEQUENCE: 293
KCNTATCATQ RLADFLRHSS NNLKPILPPT NVGSNTX                            37

SEQ ID NO: 294          moltype = AA  length = 37
FEATURE                 Location/Qualifiers
source                  1..37
                        mol_type = protein
                        organism = synthetic construct
SITE                    37
                        note = (2S,4R)-4-hydroxypyrrolidine-2-carboxamide
SEQUENCE: 294
KCNTATCATQ RLADFLRHSS NNLKPILPPT NVGSNTX                            37

SEQ ID NO: 295          moltype = AA  length = 37
FEATURE                 Location/Qualifiers
source                  1..37
                        mol_type = protein
                        organism = synthetic construct
SITE                    37
                        note = (2S,4R)-4-hydroxypyrrolidine-2-carboxamide
SEQUENCE: 295
KCNTATCATQ RLADFLRHSS NNLKPILPPT NVGSNTX                            37

SEQ ID NO: 296          moltype = AA  length = 37
FEATURE                 Location/Qualifiers
```

-continued

```
source                1..37
                      mol_type = protein
                      organism = synthetic construct
SITE                  37
                      note = (2S,4R)-4-hydroxypyrrolidine-2-carboxamide
SEQUENCE: 296
KCNTATCATQ RLADFLRHSS NNLKPILPPT NVGSNTX                    37

SEQ ID NO: 297        moltype = AA  length = 37
FEATURE               Location/Qualifiers
source                1..37
                      mol_type = protein
                      organism = synthetic construct
SITE                  37
                      note = (2S,4R)-4-hydroxypyrrolidine-2-carboxamide
SEQUENCE: 297
KCNTATCATQ RLADFLRHSS NNLKPILPPT NVGSNTX                    37

SEQ ID NO: 298        moltype = AA  length = 37
FEATURE               Location/Qualifiers
source                1..37
                      mol_type = protein
                      organism = synthetic construct
SITE                  37
                      note = Amidated residue
SEQUENCE: 298
KCNTATCATQ RLADFLRHSS NNLKPILPPT NVGSNTP                    37

SEQ ID NO: 299        moltype = AA  length = 37
FEATURE               Location/Qualifiers
source                1..37
                      mol_type = protein
                      organism = synthetic construct
SITE                  37
                      note = Amidated residue
SEQUENCE: 299
KCNTATCATQ RLADFLRHSS NNLKPILPPT NVGSNTP                    37

SEQ ID NO: 300        moltype = AA  length = 37
FEATURE               Location/Qualifiers
source                1..37
                      mol_type = protein
                      organism = synthetic construct
SITE                  37
                      note = Amidated residue
SEQUENCE: 300
KCNTATCATQ RLADFLRHSS NNLKPILPPT NVGSNTP                    37

SEQ ID NO: 301        moltype = AA  length = 37
FEATURE               Location/Qualifiers
source                1..37
                      mol_type = protein
                      organism = synthetic construct
SITE                  37
                      note = Amidated residue
SEQUENCE: 301
KCNTATCATQ RLADFLRHSS NNLKPILPPT NVGSNTP                    37

SEQ ID NO: 302        moltype = AA  length = 37
FEATURE               Location/Qualifiers
source                1..37
                      mol_type = protein
                      organism = synthetic construct
SITE                  37
                      note = Amidated residue
SEQUENCE: 302
KCNTATCATQ RLADFLRHSS NNLKPILPPT NVGSNTP                    37

SEQ ID NO: 303        moltype = AA  length = 37
FEATURE               Location/Qualifiers
source                1..37
                      mol_type = protein
                      organism = synthetic construct
SITE                  37
                      note = Amidated residue
SEQUENCE: 303
KCNTATCATQ RLADFLRHSS NNLKPILPPT NVGSNTP                    37

SEQ ID NO: 304        moltype = AA  length = 37
```

-continued

```
FEATURE                Location/Qualifiers
source                 1..37
                       mol_type = protein
                       organism = synthetic construct
SITE                   37
                       note = Amidated residue
SEQUENCE: 304
KCNTATCATQ RLADFLRHSS NNLKPILPPT NVGSNTP                       37

SEQ ID NO: 305         moltype = AA  length = 37
FEATURE                Location/Qualifiers
source                 1..37
                       mol_type = protein
                       organism = synthetic construct
SITE                   37
                       note = Amidated residue
SEQUENCE: 305
KCNTATCATQ RLADFLRHSS NNLKPILPPT NVGSNTP                       37

SEQ ID NO: 306         moltype = AA  length = 37
FEATURE                Location/Qualifiers
source                 1..37
                       mol_type = protein
                       organism = synthetic construct
SITE                   37
                       note = Amidated residue
SEQUENCE: 306
KCNTATCATQ RLADFLRHSS NNLKPILPPT NVGSNTP                       37

SEQ ID NO: 307         moltype = AA  length = 37
FEATURE                Location/Qualifiers
source                 1..37
                       mol_type = protein
                       organism = synthetic construct
SITE                   37
                       note = Amidated residue
SEQUENCE: 307
RCNTATCATQ RLADFLRHSS NNLRPILPPT NVGSNTP                       37

SEQ ID NO: 308         moltype = AA  length = 42
FEATURE                Location/Qualifiers
source                 1..42
                       mol_type = protein
                       organism = synthetic construct
SITE                   42
                       note = Amidated residue
SEQUENCE: 308
KGGGGRCNTA TCATQRLADF LRHSSNNLRP ILPPTNVGSN TP                 42

SEQ ID NO: 309         moltype = AA  length = 37
FEATURE                Location/Qualifiers
source                 1..37
                       mol_type = protein
                       organism = synthetic construct
SITE                   21
                       note = Lysine modified with
                        (2-(2-(2-aminoethoxy)ethoxy)acetic acid)2-Gamma-glutamic
                        acid-C20 diacid via the side chain
SITE                   37
                       note = Amidated residue
SEQUENCE: 309
RCNTATCATQ RLAEFLRHSS KNLGPILPPT NVGSNTP                       37

SEQ ID NO: 310         moltype = AA  length = 37
FEATURE                Location/Qualifiers
source                 1..37
                       mol_type = protein
                       organism = synthetic construct
SEQUENCE: 310
KCNTATCATQ RLANFLVHSS NNFGAILSST NVGSNTY                       37
```

HUMAN AMYLIN ANALOG, AND DERIVATIVE THEREOF AND USE THEREOF

CROSS-REFERENCE TO RELATED APPLICATIONS

This is a continuation application of U.S. patent application Ser. No. 18/869,726, filed on Nov. 26, 2024, which is a U.S. National Stage Application of International Application No. PCT/CN2023/096811, filed on May 29, 2023, and claims priority to China Application No. 202210588910.0, filed on May 27, 2022; all of which are incorporated by reference herein in their entirety.

TECHNICAL FIELD

The present disclosure relates to the technical field of biomedicine or biopharmaceuticals, and more particularly to a human amylin analog and a derivative thereof, and use thereof for treating and/or preventing a disease related to amylin or metabolism.

INCORPORATION BY REFERENCE OF SEQUENCE LISTING

The Sequence Listing in an XML file, named 70304-703_301_SL.xml of 489,760 bytes, created on Apr. 28, 2026, and submitted to the United States Patent and Trademark Office via Patent Center, is incorporated herein by reference.

BACKGROUND

Amylin, also known as islet amyloid polypeptide (IAPP), is a member of calcitonin gene-related peptide (CGRP) family, which exerts physiological functions by activating corresponding receptors, and has many functions such as blood glucose regulation, food intake control and metabolism regulation. However, the amylin has a tendency towards fibrosis under neutral or alkaline conditions and is prone to form an amyloid precipitation. Meanwhile, the amylin has a short retention time in blood and a half-life of only about 13 minutes, which limits its use in the treatment of diseases. Therefore, it is of great significance to develop an amylin analog with better stability, longer half-life and more obvious therapeutic effect for the treatment of metabolic diseases such as diabetes and obesity.

Pramlintide (also known as Symlin) is an amylin analog, and by substituting amino acid residues 25, 28 and 29 with Pro, the stability in solution is improved. At present, the Pramlintide has been approved in the market for the treatment of diabetes. However, the half-life of the Pramlintide is only about 48 minutes, so that the efficacy needs to be maintained by frequent injections, and the Pramlintide is prone to aggregate and precipitate under a neutral pH condition, which limits the combined use of the Pramlintide with other therapeutic drugs. WO2012162542A1 discloses a derivative of an amylin polypeptide analog, which is substituted by lysine and linking to polyethylene glycol to prolong the action time of amylin or an analog thereof in vivo, but the affinity of the pegylated derivative to an amylin receptor is obviously decreased. Li-Mei Yan et al. (Proc Natl Acad Sci, 2006,103 (7): 2046-2051) disclosed an amylin derivative IAPP-GI, which improved the solubility of amylin by methylation modification of 24-Gly and 26-Ile, but the activity was decreased compared with that of wild-type amylin. Cagrilintide is a long-acting amylin derivative developed by Novo Nordisk Company, which is currently in a phase II clinical stage.

Compared with the amylin, the amylin analogs/derivatives in the prior art have been improved in solubility, stability, half-life, activity, etc., but there are still some technical problems such as insufficient in-vivo efficacy and insufficient drug stability. Therefore, the amylin derivatives still need further improvement.

SUMMARY

The present disclosure provides a new amylin analog and a derivative thereof, a preparation method thereof, a pharmaceutical composition and product comprising the polypeptide or the derivative thereof, and use thereof in preventing and/or treating a disease.

In one aspect, the present disclosure provides a new amylin analog or a pharmaceutically acceptable salt thereof, wherein the analog comprises an amino acid sequence as shown in $X_1$CNTA TCATQ RLA$X_{14}$FL$X_{17}$H$X_{19}X_{20}$ $X_{21}X_{22}X_{23}X_{24}X_{25}$ IL$X_{28}X_{29}$T NVGS$X_{35}$ T$X_{37}$ [formula (I)] (SEQ ID NO: 105), the amino acid sequence contains one or more amino acid mutations shown in a $1^{st}$ position, a $14^{th}$ position, a $17^{th}$ position, a $19^{th}$ position, a $20^{th}$ position, a $21^{st}$ position, a $22^{nd}$ position, a $23^{rd}$ position, a $24^{th}$ position, a $25^{th}$ position, a $28^{th}$ position, a $29^{th}$ position, a $35^{th}$ position and a $37^{th}$ position, and preferably, $X_1$ is selected from K, D, Dab, Dap, E, H, Har, Orn or R, or deleted, $X_{14}$ is selected from N, Aad, Dab, Dap, E or D, $X_{17}$ is selected from V, Orn or R, $X_{19}$ is selected from S or K, $X_{20}$ is selected from S or K, $X_{21}$ is selected from N or K, $X_{22}$ is selected from Nor K, $X_{23}$ is selected from F, L or K, $X_{24}$ is selected from G, R, H, P, D, N, S, K, αK, Dap, Dab, Orn, Cit, Sar, Trx or AOC, $X_{25}$ is selected from A, K or P, $X_{28}$ is selected from S or P, $X_{29}$ is selected from S or P, $X_{35}$ is selected from N or G, and $X_{37}$ is selected from Y, 3-Am-Pro, Aze, cis-Hyp, P, Pip, αMePro or trans-Hyp.

In some preferred embodiments, the amylin analog comprises an amino acid sequence as shown in $X_1$CNTA TCATQ RLA$X_{14}$F L$X_{17}$HSS NN$X_{23}X_{24}X_{25}$ IL$X_{28}X_{29}$T NVGSN T$X_{37}$ [formula (II)] (SEQ ID NO: 106), the amino acid sequence contains one or more amino acid mutations shown in a $1^{st}$ position, a $14^{th}$ position, a $17^{th}$ position, a $23^{rd}$ position, a $24^{th}$ position, a $25^{th}$ position, a $28^{th}$ position, a $29^{th}$ position and a $37^{th}$ position, and

- preferably, $X_1$ is selected from K, D, Dab, Dap, E, H, Har, Orn or R, or deleted, $X_{14}$ is selected from N, Aad, Dab, Dap, E or D, $X_{17}$ is selected from V, Orn or R, $X_{23}$ is selected from F, L or K, $X_{24}$ is selected from G, R, H, P, D, N, S, K, αK, Dap, Dab, Orn, Cit, Sar, Trx or AOC, $X_{25}$ is selected from A, K or P, $X_{28}$ is selected from S or P, $X_{29}$ is selected from S or P, and $X_{37}$ is selected from Y, 3-Am-Pro, Aze, cis-Hyp, P, Pip, αMePro or trans-Hyp;
- preferably, $X_1$ is selected from K or R, $X_{14}$ is selected from N, Aad, Dab, Dap, E or D, $X_{17}$ is selected from V, Orn or R, $X_{23}$ is selected from F, L or K, $X_{24}$ is selected from G, R, H, P, D, N, S, K, αK, Dap, Dab, Orn, Cit, Sar, Trx or AOC, $X_{25}$ is selected from A, K or P, $X_{28}$ is selected from S or P, $X_{29}$ is selected from S or P, and $X_{37}$ is selected from Y, 3-Am-Pro, Aze, cis-Hyp, P, Pip, αMePro or trans-Hyp;
- preferably, $X_1$ is selected from K, D, Dab, Dap, E, H, Har, Orn or R, or deleted, $X_{14}$ is selected from N, Aad, Dab, Dap, E or D, $X_{17}$ is selected from V, Orn or R, $X_{23}$ is selected from F, L or K, $X_{24}$ is selected from G, R or K, $X_{25}$ is selected from A, K or P, $X_{28}$ is selected from S or P, $X_{29}$ is selected from S or P, and $X_{37}$ is selected from Y, 3-Am-Pro, Aze, cis-Hyp, P, Pip, αMePro or trans-Hyp;

preferably, $X_1$ is selected from K or R, $X_{14}$ is selected from N, Aad, Dab, Dap, E or D, $X_{17}$ is selected from V, Orn or R, $X_{23}$ is selected from F, L or K, $X_{24}$ is selected from G, R or K, $X_{25}$ is selected from A, K or P, $X_{28}$ is selected from S or P, $X_{29}$ is selected from S or P, and $X_{37}$ is selected from Y, 3-Am-Pro, Aze, cis-Hyp, P, Pip, αMePro or trans-Hyp;

preferably, $X_1$ is selected from K, D, Dab, Dap, E, H, Har, Orn or R, or deleted, $X_{14}$ is selected from N, Aad, Dab, Dap, E or D, $X_{17}$ is selected from V, Orn or R, $X_{23}$ is selected from F, L or K, $X_{24}$ is selected from G, R, H, P, D, N, S, K, αK, Dap, Dab, Orn, Cit, Sar, Trx or AOC, $X_{25}$ is selected from A, K or P, $X_{28}$ is selected from S or P, $X_{29}$ is selected from S or P, and $X_{37}$ is selected from P or trans-Hyp;

preferably, $X_1$ is selected from K or R, $X_{14}$ is selected from N, Aad, Dab, Dap, E or D, $X_{17}$ is selected from V, Orn or R, $X_{23}$ is selected from F, L or K, $X_{24}$ is selected from G, R or K, $X_{25}$ is selected from A, K or P, $X_{28}$ is selected from S or P, $X_{29}$ is selected from S or P, and $X_{37}$ is selected from P or trans-Hyp;

especially preferably, $X_1$ is selected from K or R, $X_{14}$ is selected from N or D, $X_{17}$ is selected from V or R, $X_{23}$ is selected from F or L, $X_{24}$ is selected from G, R or K, $X_{25}$ is selected from A or P, $X_{28}$ is selected from S or P, $X_{29}$ is selected from S or P, and $X_{37}$ is selected from Y, P or trans-Hyp;

further preferably, $X_1$ is K, $X_{14}$ is selected from N or D, $X_{17}$ is selected from V or R, $X_{23}$ is selected from F or L, $X_{24}$ is selected from G, R or K, $X_{25}$ is selected from A or P, $X_{28}$ is selected from S or P, $X_{29}$ is selected from S or P, and $X_{37}$ is selected from Y, P or trans-Hyp;

further preferably, $X_1$ is R, $X_{14}$ is selected from N or D, $X_{17}$ is selected from V or R, $X_{23}$ is selected from F or L, $X_{24}$ is selected from G, R or K, $X_{25}$ is selected from A or P, $X_{28}$ is selected from S or P, $X_{29}$ is selected from S or P, and $X_{37}$ is selected from Y, P or trans-Hyp;

further preferably, $X_1$ is selected from K or R, $X_{14}$ is D, $X_{17}$ is R, $X_{23}$ is L, $X_{25}$ is P, $X_{24}$ is selected from G, R or K, $X_{28}$ is P, $X_{29}$ is P, and $X_{37}$ is P or trans-Hyp;

more preferably, $X_1$ is K, $X_{14}$ is D, $X_{17}$ is R, $X_{23}$ is L, $X_{24}$ is selected from G or K, $X_{25}$ is P, $X_{28}$ is P, $X_{29}$ is P, and $X_{37}$ is P or trans-Hyp; and most preferably, $X_1$ is K, $X_{14}$ is D, $X_{17}$ is R, $X_{23}$ is L, $X_{24}$ is K, $X_{25}$ is P, $X_{28}$ is P, $X_{29}$ is P, and $X_{37}$ is P or trans-Hyp.

In one aspect, the present disclosure provides a new amylin analog derivative or a pharmaceutically acceptable salt thereof, wherein the amylin analog derivative has one or more amino acid modifications, and the analog derivative comprises a polypeptide sequence of the amylin analog mentioned above.

In some embodiments, the polypeptide analog or the derivative thereof in the present disclosure comprises an amino acid sequence as shown in SEQ ID NO. 2 to 104 in Table 1.

TABLE 1

| SEQ ID NO. | Amino acids |
|---|---|
| 1 | KCNTATCATQRLAEFLRHSSNNFGPILPPTNVGSNTP-$NH_2$ |
| 2 | KCNTATCATQRLADFLRHSSNNLGPILPPTNVGSNT-trans-Hyp-$NH_2$ |
| 3 | KCNTATCATQRLADFLRHSSNNLKPILPPTNVGSNT-trans-Hyp-$NH_2$ |
| 4 | RCNTATCATQRLADFLRHSKNNLGPILPPTNVGSNT-trans-Hyp-$NH_2$ |
| 5 | RCNTATCATQRLAEFLRHSSKNLGPILPPTNVGSNTP-$NH_2$ |
| 6 | RCNTATCATQRLAEFLRHSSNKLGPILPPTNVGSNTP-$NH_2$ |
| 7 | RCNTATCATQRLAEFLRHSSNNKGPILPPTNVGSNTP-$NH_2$ |
| 8 | RCNTATCATQRLAEFLRHSSNNLKPILPPTNVGSNTP-$NH_2$ |
| 9 | RCNTATCATQRLAEFLRHSSNNLGKILPPTNVGSNTP-$NH_2$ |
| 10 | RCNTATCATQRLAEFLRHSSNNLKPILSSTNVGSNTP-$NH_2$ |
| 11 | RCNTATCATQRLAEFLRHSSNNLKAILPSTNVGSNTP-$NH_2$ |
| 12 | RCNTATCATQRLAEFLRHSSNNLKAILSPTNVGSNTP-$NH_2$ |
| 13 | RCNTATCATQRLAEFLRHSSNNLKPILPSTNVGSNTP-$NH_2$ |
| 14 | RCNTATCATQRLAEFLRHSSNNLKPILSPTNVGSNTP-$NH_2$ |
| 15 | RCNTATCATQRLAEFLRHSSNNLKAILPPTNVGSNTP-$NH_2$ |
| 16 | RCNTATCATQRLAEFLRHSSNNLKPILPPTNVGSNTY-$NH_2$ |
| 17 | RCNTATCATQRLAEFLRHSSNNLKAILSSTNVGSNTY-$NH_2$ |
| 18 | RCNTATCATQRLAEFLRHSSNNLKPILSSTNVGSNTY-$NH_2$ |
| 19 | RCNTATCATQRLAEFLRHSSNNLKAILPSTNVGSNTY-$NH_2$ |
| 20 | RCNTATCATQRLAEFLRHSSNNLKAILSPTNVGSNTY-$NH_2$ |

TABLE 1-continued

| SEQ ID NO. | Amino acids |
|---|---|
| 21 | RCNTATCATQRLAEFLRHSSNNLKPILPSTNVGSNTY-$NH_2$ |
| 22 | RCNTATCATQRLAEFLRHSSNNLKPILSPTNVGSNTY-$NH_2$ |
| 23 | RCNTATCATQRLAEFLRHSSNNLKAILPPTNVGSNTY-$NH_2$ |
| 24 | RCNTATCATQRLAEFLRHSSNNLKPILPPTNVGSGTP-$NH_2$ |
| 25 | RCNTATCATQRLAEFLRHSSNNLKAILSSTNVGSGTP-$NH_2$ |
| 26 | RCNTATCATQRLAEFLRHSSNNLKPILSSTNVGSGTP-$NH_2$ |
| 27 | RCNTATCATQRLAEFLRHSSNNLKAILPSTNVGSGTP-$NH_2$ |
| 28 | RCNTATCATQRLAEFLRHSSNNLKAILSPTNVGSGTP-$NH_2$ |
| 29 | RCNTATCATQRLAEFLRHSSNNLKPILPSTNVGSGTP-$NH_2$ |
| 30 | RCNTATCATQRLAEFLRHSSNNLKPILSPTNVGSGTP-$NH_2$ |
| 31 | RCNTATCATQRLAEFLRHSSNNLKAILPPTNVGSGTP-$NH_2$ |
| 32 | KCNTATCATQRLAEFLRHSSNNLKPILPPTNVGSNTP-$NH_2$ |
| 33 | KCNTATCATQRLAEFLRHSSNNLKPILSSTNVGSNTP-$NH_2$ |
| 34 | KCNTATCATQRLAEFLRHSSNNLKAILPSTNVGSNTP-$NH_2$ |
| 35 | KCNTATCATQRLAEFLRHSSNNLKAILSPTNVGSNTP-$NH_2$ |
| 36 | KCNTATCATQRLAEFLRHSSNNLKPILPSTNVGSNTP-$NH_2$ |
| 37 | KCNTATCATQRLAEFLRHSSNNLKPILSPTNVGSNTP-$NH_2$ |
| 38 | KCNTATCATQRLAEFLRHSSNNLKAILPPTNVGSNTP-$NH_2$ |
| 39 | RCNTATCATQRLAEFLRHSSNNLKPILPPTNVGSNT-trans-Hyp-$NH_2$ |
| 40 | RCNTATCATQRLAEFLRHSSNNLKPILPPTNVGSGT-trans-Hyp-$NH_2$ |
| 41 | RCNTATCATQRLADFLRHSSNNLKPILPPTNVGSNTP-$NH_2$ |
| 42 | RCNTATCATQRLA-Aad-FLRHSSNNLKPILPPTNVGSNTP-$NH_2$ |
| 43 | RCNTATCATQRLA-Dab-FLRHSSNNLKPILPPTNVGSNTP-$NH_2$ |
| 44 | RCNTATCATQRLA-Dap-FLRHSSNNLKPILPPTNVGSNTP-$NH_2$ |
| 45 | RCNTATCATQRLAEFL-Orn-HSSNNLKPILPPTNVGSNTP-$NH_2$ |
| 46 | RCNTATCATQRLAEFLRHSSNNLKPILPPTNVGSNTP-$NH_2$ |
| 47 | RCNTATCATQRLADFLRHSSNNLKPILPPTNVGSNTP-$NH_2$ |
| 48 | CNTATCATQRLAEFLRHSSNNLKPILPPTNVGSNTP-$NH_2$ |
| 49 | CNTATCATQRLADFLRHSSNNLKPILPPTNVGSNTP-$NH_2$ |
| 50 | RCNTATCATQRLADFLRHSSNNLKPILPPTNVGSNT-trans-Hyp-$NH_2$ |
| 51 | CNTATCATQRLAEFLRHSSNNLKPILPPTNVGSNT-trans-Hyp-$NH_2$ |
| 52 | CNTATCATQRLADFLRHSSNNLKPILPPTNVGSNT-trans-Hyp-$NH_2$ |
| 53 | RCNTATCATQRLAEFLRHSSNNLKPILPPTNVGSNT-cis-Hyp-$NH_2$ |
| 54 | RCNTATCATQRLADFLRHSSNNLKPILPPTNVGSNT-cis-Hyp-$NH_2$ |
| 55 | RCNTATCATQRLAEFLRHSSNNLKPILPPTNVGSNT-Pip-$NH_2$ |
| 56 | RCNTATCATQRLADFLRHSSNNLKPILPPTNVGSNT-Pip-$NH_2$ |
| 57 | RCNTATCATQRLAEFLRHSSNNLKPILPPTNVGSNT-Aze-$NH_2$ |
| 58 | RCNTATCATQRLADFLRHSSNNLKPILPPTNVGSNT-Aze-$NH_2$ |
| 59 | RCNTATCATQRLAEFLRHSSNNLKPILPPTNVGSNT-3-Am-Pro-$NH_2$ |

TABLE 1-continued

| SEQ ID NO. | Amino acids |
|---|---|
| 60 | RCNTATCATQRLADFLRHSSNNLKPILPPTNVGSNT-3-Am-Pro-$NH_2$ |
| 61 | RCNTATCATQRLAEFLRHSSNNLKPILPPTNVGSNT-αMePro-$NH_2$ |
| 62 | RCNTATCATQRLADFLRHSSNNLKPILPPTNVGSNT-αMePro-$NH_2$ |
| 63 | KCNTATCATQRLADFLRHSSNNFGPILPPTNVGSNT-trans-Hyp-$NH_2$ |
| 64 | Dap-CNTATCATQRLADFLRHSSNNLKPILPPTNVGSNT-trans-Hyp-$NH_2$ |
| 65 | Dab-CNTATCATQRLADFLRHSSNNLKPILPPTNVGSNT-trans-Hyp-$NH_2$ |
| 66 | Orn-CNTATCATQRLADFLRHSSNNLKPILPPTNVGSNT-trans-Hyp-$NH_2$ |
| 67 | Har-CNTATCATQRLADFLRHSSNNLKPILPPTNVGSNT-trans-Hyp-$NH_2$ |
| 68 | HCNTATCATQRLADFLRHSSNNLKPILPPTNVGSNT-trans-Hyp-$NH_2$ |
| 69 | DCNTATCATQRLADFLRHSSNNLKPILPPTNVGSNT-trans-Hyp-$NH_2$ |
| 70 | ECNTATCATQRLADFLRHSSNNLKPILPPTNVGSNT-trans-Hyp-$NH_2$ |
| 71 | RCNTATCATQRLADFLRHSSNNKGPILPPTNVGSNT-trans-Hyp-$NH_2$ |
| 72 | RCNTATCATQRLADFLRHSSNKLGPILPPTNVGSNT-trans-Hyp-$NH_2$ |
| 73 | RCNTATCATQRLADFLRHSSKNLGPILPPTNVGSNT-trans-Hyp-$NH_2$ |
| 74 | RCNTATCATQRLADFLRHKSNNLGPILPPTNVGSNT-trans-Hyp-$NH_2$ |
| 75 | RCNTATCATQRLADFLRHSSNNLGKILPPTNVGSNT-trans-Hyp-$NH_2$ |
| 76 | RCNTATCATQRLADFLRHSSNNLGPILPPTNVGSNT-trans-Hyp-$NH_2$ |
| 77 | HCNTATCATQRLADFLRHSSNNLGPILPPTNVGSNT-trans-Hyp-$NH_2$ |
| 78 | KCNTATCATQRLANFLVHSSNNFGPILPPTNVGSNTY |
| 79 | KCNTATCATQ RLADFLRHSS NNLKPILPPT NVGSNT-Aze-$NH_2$ |
| 80 | KCNTATCATQ RLADFLRHSS NNLKPILPPT NVGSNT-Aze-$NH_2$ |
| 81 | KCNTATCATQ RLANFLVHSS NNFGPILPPT NVGSNTY-$NH_2$ |
| 82 | KCNTATCATQ RLADFLRHSS NNLKPILPPT NVGSNT-Aze-$NH_2$ |
| 83 | KCNTATCATQ RLADFLRHSS NNLRPILPPT NVGSNT-trans-Hyp-$NH_2$ |
| 84 | KCNTATCATQ RLADFLRHSS NNLHPILPPT NVGSNT-trans-Hyp-$NH_2$ |
| 85 | KCNTATCATQ RLADFLRHSS NNLKPILPPT NVGSNTP-$NH_2$ |
| 86 | KCNTATCATQ RLADFLRHSS NNLRPILPPT NVGSNTP-$NH_2$ |
| 87 | KCNTATCATQ RLADFLRHSS NNLHPILPPT NVGSNTP-$NH_2$ |
| 88 | KCNTATCATQ RLADFLRHSS NNLPPILPPT NVGSNTP-$NH_2$ |
| 89 | KCNTATCATQ RLADFLRHSS NNLDPILPPT NVGSNTP-$NH_2$ |
| 90 | KCNTATCATQ RLADFLRHSS NNLNPILPPT NVGSNTP-$NH_2$ |
| 91 | KCNTATCATQ RLADFLRHSS NNLSPILPPT NVGSNTP-$NH_2$ |
| 92 | KCNTATCATQ RLADFLRHSS NNL-αK-PILPPT NVGSNTP-$NH_2$ |
| 93 | KCNTATCATQ RLADFLRHSS NNL-Dap-PILPPT NVGSNTP-$NH_2$ |
| 94 | KCNTATCATQ RLADFLRHSS NNL-Dab-PILPPT NVGSNTP-$NH_2$ |
| 95 | KCNTATCATQ RLADFLRHSS NNL-Orn-PILPPT NVGSNTP-$NH_2$ |
| 96 | KCNTATCATQ RLADFLRHSS NNL-Cit-PILPPT NVGSNTP-$NH_2$ |
| 97 | KCNTATCATQ RLADFLRHSS NNL-Sar-PILPPT NVGSNTP-$NH_2$ |
| 98 | KCNTATCATQ RLADFLRHSS NNL-Trx-PILPPT NVGSNTP-$NH_2$ |

TABLE 1-continued

| SEQ ID NO. | Amino acids |
|---|---|
| 99 | KCNTATCATQ RLADFLRHSS NNL-AOC-PILPPT NVGSNTP-$NH_2$ |
| 100 | KCNTATCATQ RLADFLRHSS NNLGPILPPT NVGSNT-Aze-$NH_2$ |
| 101 | KCNTATCATQ RLADFLRHSS NNLKPILPPT NVGSNT-trans-Hyp-$NH_2$ |
| 102 | KCNTATCATQ RLADFLRHSS NNLKPILPPT NVGSNTP-$NH_2$ |
| 103 | RCNTA TCATQ RLADF LRHSS NNLRP ILPPT NVGSN TP-$NH_2$ |
| 104 | KGGGG RCNTA TCATQ RLADF LRHSS NNLRP ILPPT NVGSN TP-$NH_2$ |

In some embodiments, compared with a sequence of a wild-type polypeptide, the sequence of the polypeptide analog derivative in the present disclosure comprises 1 to 10 amino acid modifications, preferably 1 to 8 amino acid modifications, further preferably 1 to 4 amino acid modifications, more preferably 2 amino acid modifications, and most preferably 1 amino acid modification.

In some embodiments, compared with the sequence of the wild-type polypeptide, the sequence of the polypeptide analog derivative is subjected to amino acid modification(s) in which a functional group capable of being used for coupling is introduced into a side chain of natural amino acid or unnatural amino acid, which comprises, but is not limited to, glutamic acid, aspartic acid, lysine, glutamine or asparagine, preferably, the amino acid modification is carried out on the side chain of lysine, preferably, the lysine is located in a first position of the polypeptide derivative, and the modified side chain is selected from an Alpha-amino or Epsilon-amino side chain of lysine, preferably the Epsilon-amino side chain.

In some embodiments, the functional group capable of being used for coupling comprises an extension part and a linker linking the extension part to a modified amino acid, wherein the linker may be composed of one or more linkers, and a linking order of the linkers is arbitrary, as long as the linkage of the extension part to the modified amino acid can be understood as being in a form within the scope of the present disclosure.

In some preferred embodiments, the single linker may be in the following structure:

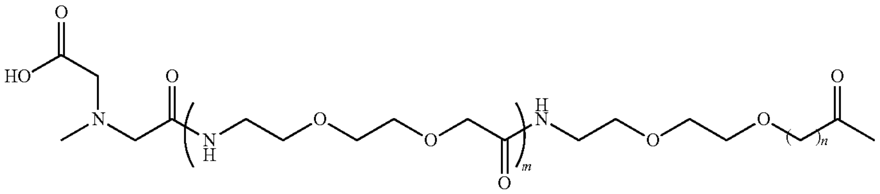
,
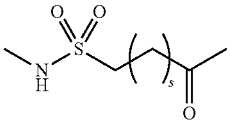
,

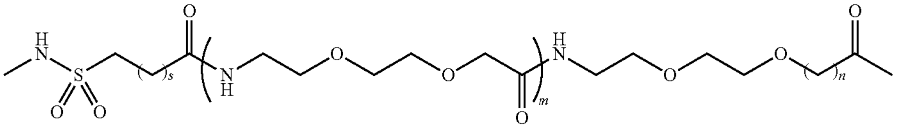
,

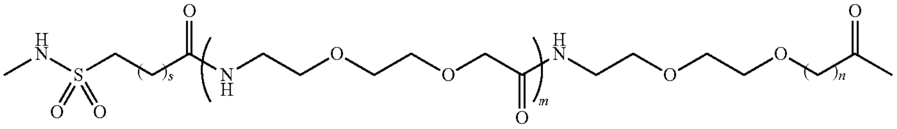
,

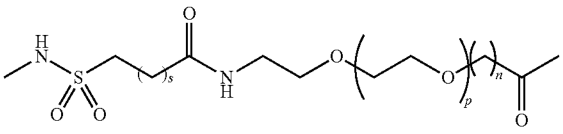
,

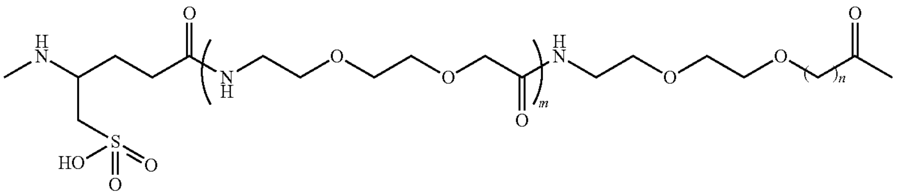
,

-continued
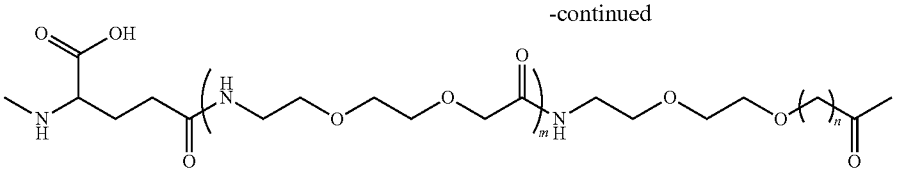
, or
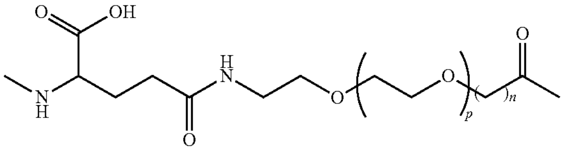
,
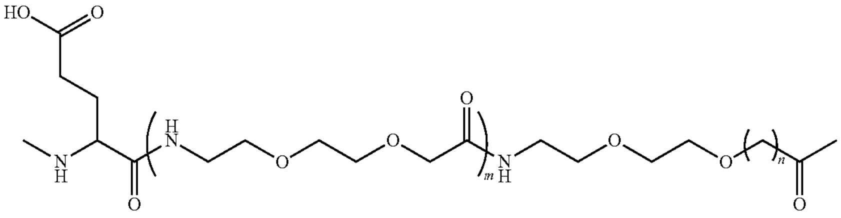
,
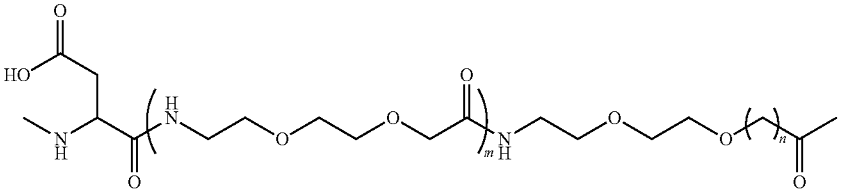
,
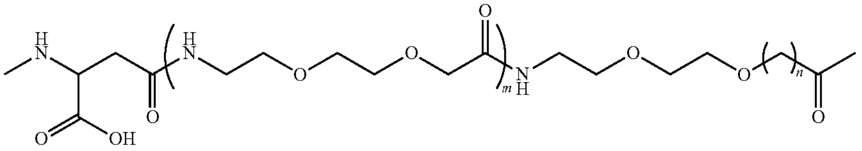
,
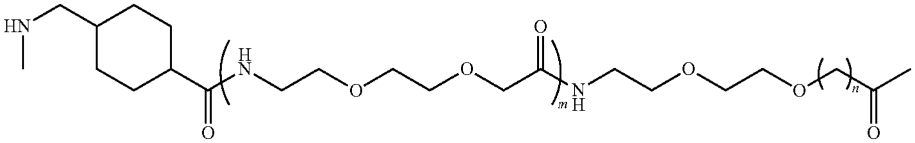
,
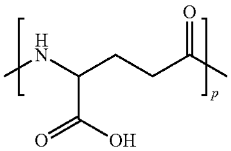
,
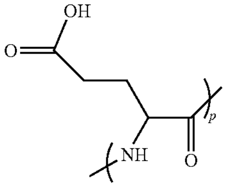
,
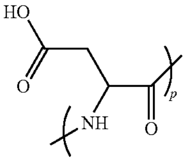
,
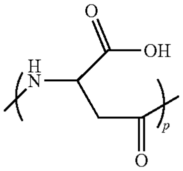
,
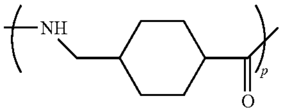
, or
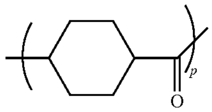
,
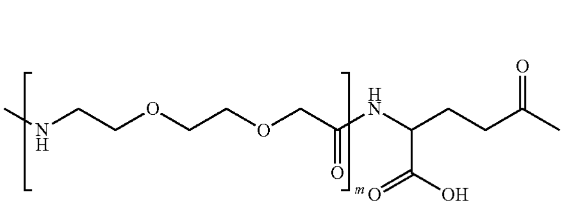
,
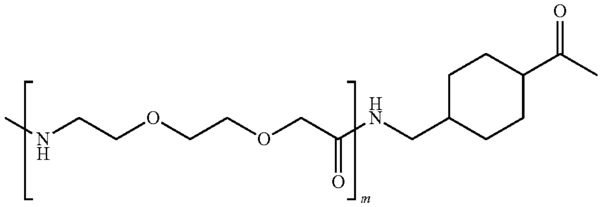
,
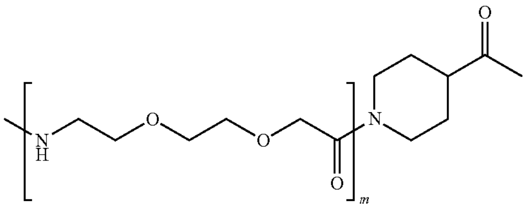
,
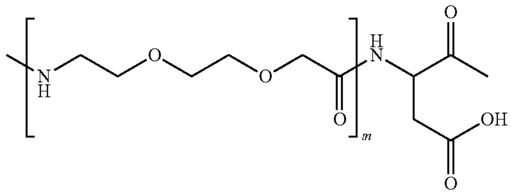
, -continued
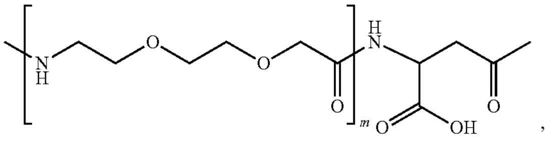 , 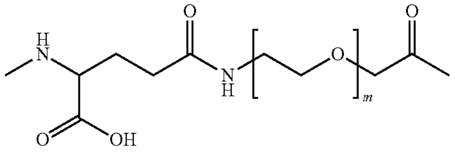 ,
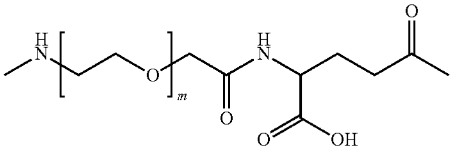 ,
wherein, m is 0, 1, 2 or 3; n is 1, 2 or 3; s is any integer from 0 to 6; and p is any integer from 1 to 8.
Preferably, the linker is:
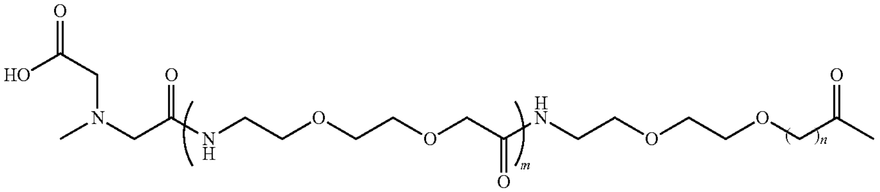 ,
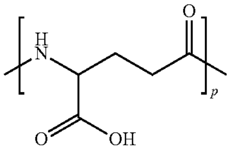 ,
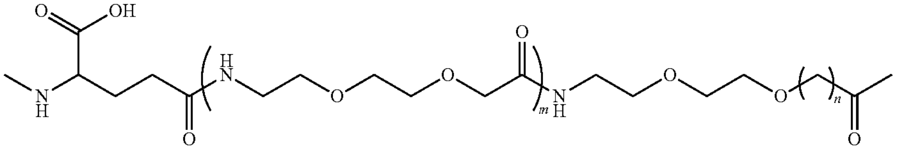 ,
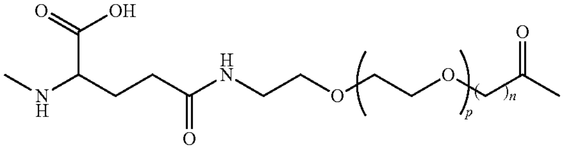 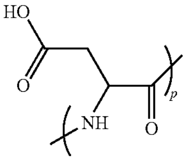 ,
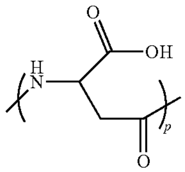 , 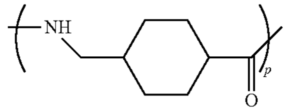 , or 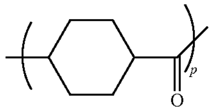 ,
wherein, m is 1 or 2; n is 1 or 2; and p is any integer from 1 to 5.
Further preferably, the linker is:
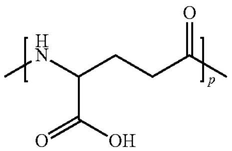
wherein, p is any integer from 1 to 5,
preferably, p is 1, and the linker is γGlu.
In preferred embodiments, the extension part is:
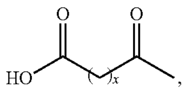 , 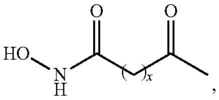 , or
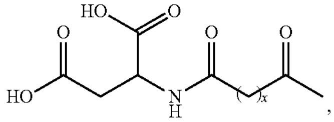 ,
wherein, x is any integer from 4 to 38; and preferably, the extension part is

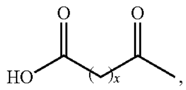

wherein x is any integer from 4 to 38.

Preferably, the amino acid sequence of the polypeptide analog comprises an amino acid sequence as shown in formula (I):

(SEQ ID NO: 107)
$X_1CNTATCATQRLAX_{14}FLX_{17}HX_{19}X_{20}X_{21}X_{22}X_{23}X_{24}X_{25}ILX_{28}$
$X_{29}TNVGSX_{35}TX_{37}$ formula (I), wherein, $X_1$ is selected from K or R, $X_{14}$ is selected from N, Aad, Dab, Dap, E or D, $X_{17}$ is selected from V, Orn or R, $X_{23}$ is selected from F, L or K, $X_{24}$ is selected from G, R, H, P, D, N, S, K, αK, Dap, Dab, Orn, Cit, Sar, Trx or AOC, $X_{25}$ is selected from A, K or P, $X_{28}$ is selected from S or P, $X_{29}$ is selected from S or P, and $X_{37}$ is selected from Y, 3-Am-Pro, Aze, cis-Hyp, P, Pip, αMePro or trans-Hyp; and the linker is:

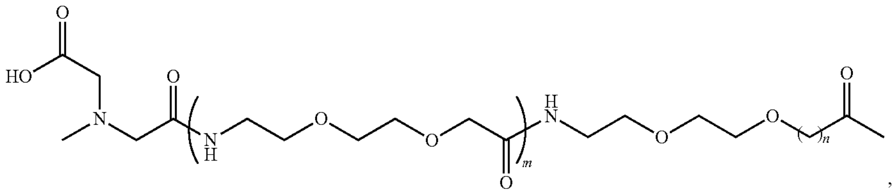

,

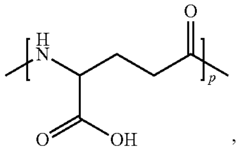

,

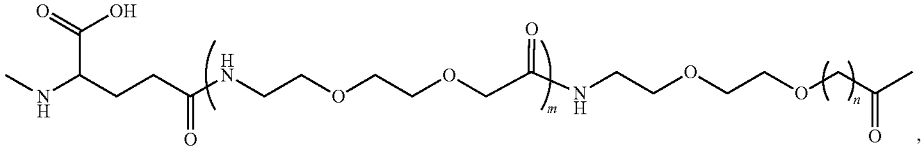

, or

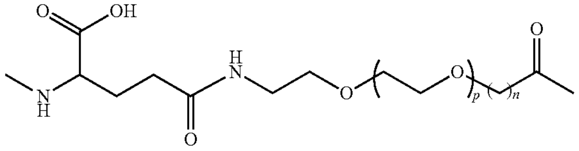

wherein m is 1 or 2; n is 1 or 2; p is any integer from 1 to 5; and the extension part is

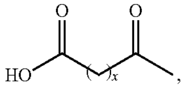

wherein x is any integer from 4 to 38.

Preferably, the amino acid sequence of the polypeptide analog comprises the amino acid sequence as shown in formula (I):

(SEQ ID NO: 108)
$X_1CNTATCATQRLAX_{14}FLX_{17}HX_{19}X_{20}X_{21}X_{22}X_{23}X_{24}X_{25}ILX_{28}$
$X_{29}TNVGSX_{35}TX_{37}$ formula (I), wherein, $X_1$ is selected from K, D, Dab, Dap, E, H, Har, Orn or R, or deleted, $X_{14}$ is selected from N, Aad, Dab, Dap, E or D, $X_{17}$ is selected from V, Orn or R, $X_{23}$ is selected from F, L or K, $X_{24}$ is selected from G, R or K, $X_{25}$ is selected from A, K or P, $X_{28}$ is selected from S or P, $X_{29}$ is selected from S or P, and $X_{37}$ is selected from Y, 3-Am-Pro, Aze, cis-Hyp, P, Pip, αMePro or trans-Hyp; and the linker is:

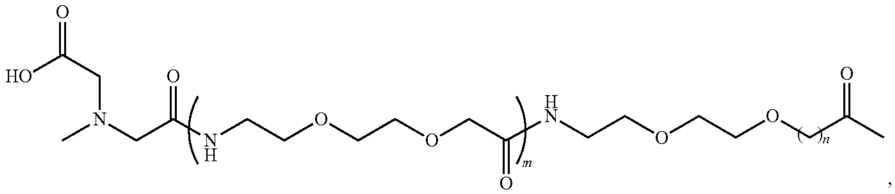

,

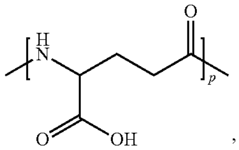

,

-continued

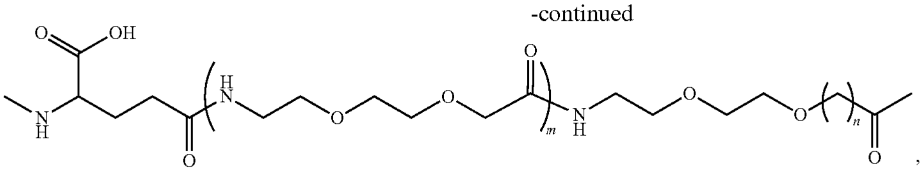

, or

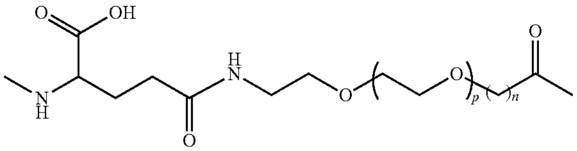

wherein m is 1 or 2; n is 1 or 2; p is any integer from 1 to 5; and the extension part is

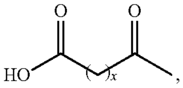

, wherein x is any integer from 4 to 38.

Preferably, the amino acid sequence of the polypeptide analog comprises an amino acid sequence as shown in formula (I):

(SEQ ID NO: 109)
$X_1$CNTATCATQRLAX$_{14}$FLX$_{17}$HX$_{19}$X$_{20}$X$_{21}$X$_{22}$X$_{23}$X$_{24}$X$_{25}$ILX$_{28}$X$_{29}$TNVGSX$_{35}$TX$_{37}$ formula (I), wherein, $X_1$ is selected from K or R, $X_{14}$ is selected from N, Aad, Dab, Dap, E or D, $X_{17}$ is selected from V, Orn or R, $X_{23}$ is selected from F, L or K, $X_{24}$ is selected from G, R or K, $X_{25}$ is selected from A, K or P, $X_{28}$ is selected from S or P, $X_{29}$ is selected from S or P, and $X_{37}$ is selected from Y, 3-Am-Pro, Aze, cis-Hyp, P, Pip, αMePro or trans-Hyp; and particularly preferably, $X_1$ is selected from K or R, $X_{14}$ is selected from N or D, $X_{17}$ is selected from V or R, $X_{23}$ is selected from F or L, $X_{24}$ is selected from G or K, $X_{25}$ is selected from A or P, $X_{28}$ is selected from S or P, $X_{29}$ is selected from S or P, and $X_{37}$ is selected from Y or trans-Hyp; and the linker is:

wherein m is 1 or 2; n is 1 or 2; p is any integer from 1 to 5; and the extension part is

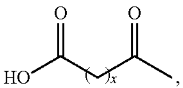

, wherein x is any integer from 4 to 38.

Preferably, the amino acid sequence of the polypeptide analog comprises an amino acid sequence as shown in formula (I):

(SEQ ID NO: 110)
$X_1$CNTATCATQRLAX$_{14}$FLX$_{17}$HX$_{19}$X$_{20}$X$_{21}$X$_{22}$X$_{23}$X$_{24}$X$_{25}$ILX$_{28}$X$_{29}$TNVGSX$_{35}$TX$_{37}$ formula (I), wherein, $X_1$ is K, $X_{14}$ is selected from N or D, $X_{17}$ is selected from V or R, $X_{23}$ is selected from F or L, $X_{24}$ is selected from G or K, $X_{25}$ is selected from A or P, $X_{28}$ is selected from S or P, $X_{29}$ is selected from S or P, and $X_{37}$ is selected from Y or trans-Hyp; and the linker is:

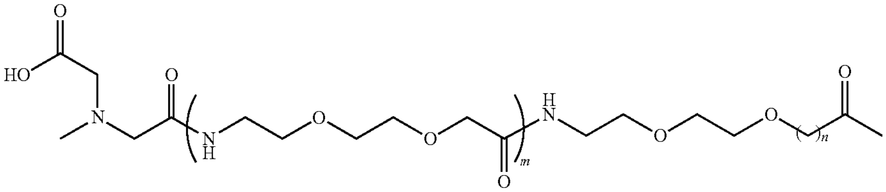

,

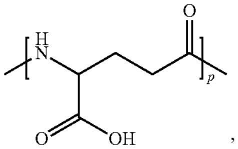

,

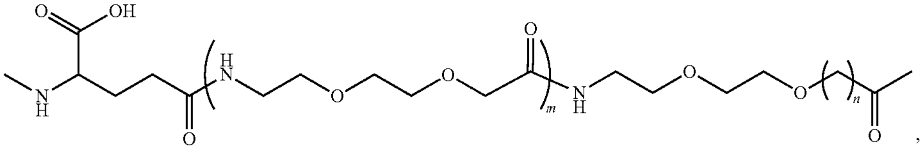

, or

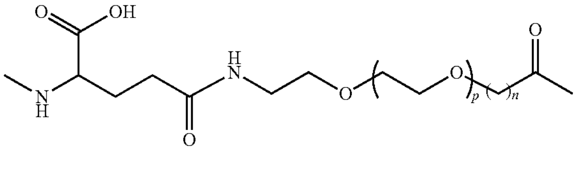

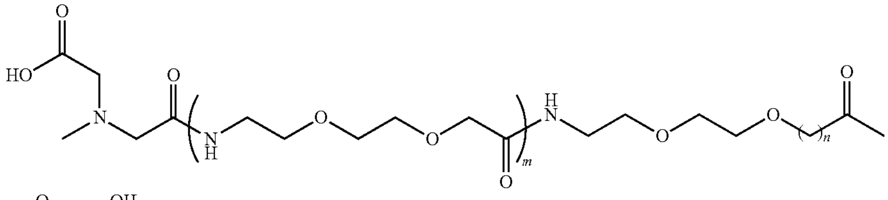
,
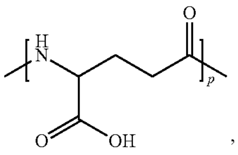
,
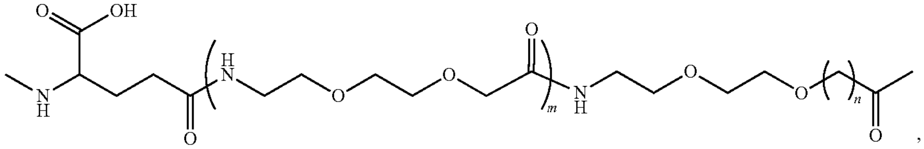
, or
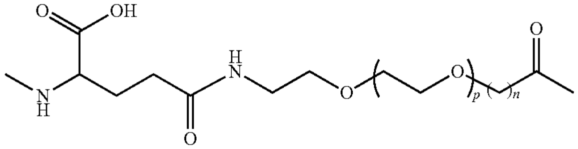

wherein m is 1 or 2; n is 1 or 2; p is any integer from 1 to 5; and the extension part is

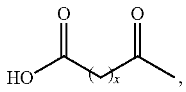
, wherein x is any integer from 4 to 38.

Preferably, the amino acid sequence of the polypeptide analog comprises an amino acid sequence as shown in formula (I):

```
                                        (SEQ ID NO: 111)
X1CNTATCATQRLAX14FLX17HX19X20X21X22X23X24X25ILX28
X29TNVGSX35TX37 formula (I),
```

wherein, $X_1$ is R, $X_{14}$ is selected from N or D, $X_{17}$ is selected from V or R, $X_{23}$ is selected from F or L, $X_{24}$ is selected from G or K, $X_{25}$ is selected from A or P, $X_{28}$ is selected from S or P, $X_{29}$ is selected from S or P, and $X_{37}$ is selected from Y or trans-Hyp; and the linker is:

wherein m is 1 or 2; n is 1 or 2; p is any integer from 1 to 5; and the extension part is

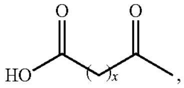
, wherein x is any integer from 4 to 38.

Preferably, the amino acid sequence of the polypeptide analog comprises an amino acid sequence as shown in formula (I):

```
                                        (SEQ ID NO: 112)
X1CNTATCATQRLAX14FLX17HX19X20X21X22X23X24X25ILX28
X29TNVGSX35TX37 formula (I),
```

wherein, $X_1$ is selected from K or R, $X_{14}$ is D, $X_{17}$ is R, $X_{23}$ is L, $X_{25}$ is P, $X_{24}$ is selected from G or K, $X_{28}$ is P, $X_{29}$ is P, and $X_{37}$ is trans-Hyp; and the linker is:

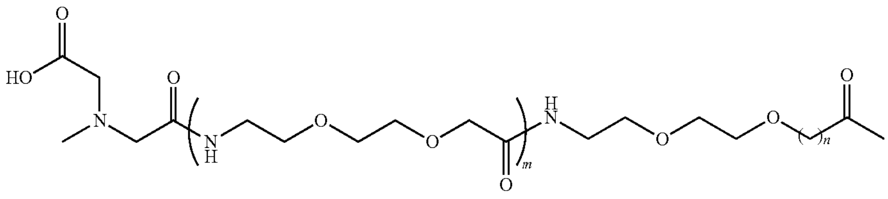
,
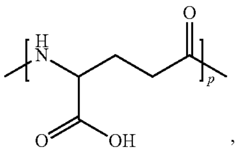
,
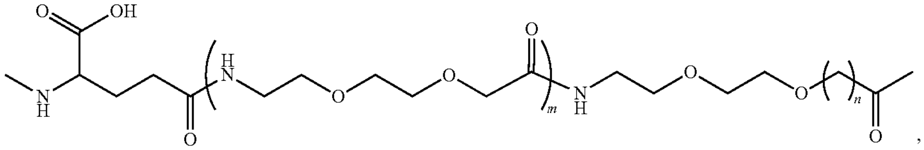
, or
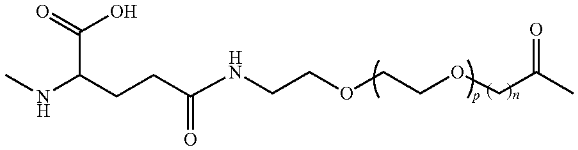

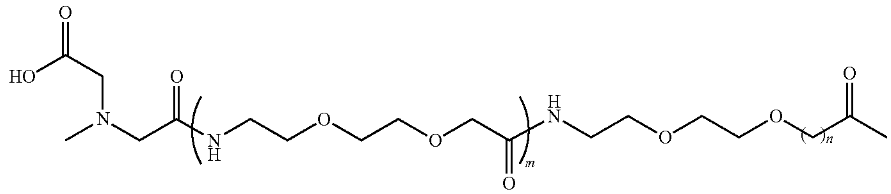
,
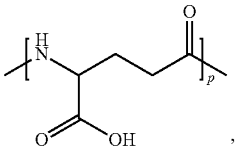
,
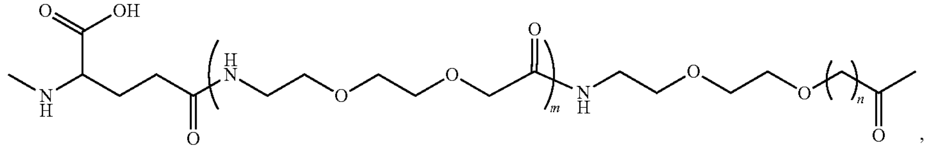
, or
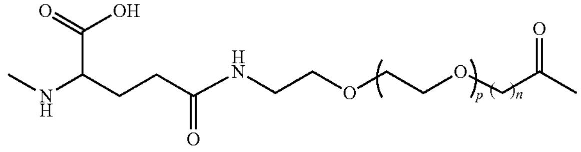

wherein m is 1 or 2; n is 1 or 2; p is any integer from 1 to 5; and the extension part is

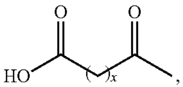
, wherein x is any integer from 4 to 38.

Preferably, the amino acid sequence of the polypeptide analog comprises an amino acid sequence as shown in formula (I):

```
                                    (SEQ ID NO: 113)
X1CNTATCATQRLAX14FLX17HX19X20X21X22X23X24X25ILX28
X29TNVGSX35TX37 formula (I),
```

wherein, $X_1$ is K, $X_{14}$ is D, $X_{17}$ is R, $X_{23}$ is L, $X_{24}$ is selected from G or K, $X_{25}$ is P, $X_{28}$ is P, $X_{29}$ is P, and $X_{37}$ is trans-Hyp; and the linker is:

wherein m is 1 or 2; n is 1 or 2; p is any integer from 1 to 5; and the extension part is

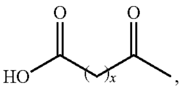
, wherein x is any integer from 4 to 38.

Preferably, the amino acid sequence of the polypeptide analog comprises an amino acid sequence as shown in formula (I):

```
                                    (SEQ ID NO: 114)
X1CNTATCATQRLAX14FLX17HX19X20X21X22X23X24X25ILX28
X29TNVGSX35TX37 formula (I),
```

wherein, $X_1$ is K, $X_{14}$ is D, $X_{17}$ is R, $X_{23}$ is L, $X_{24}$ is K, $X_{25}$ is P, $X_{28}$ is P, $X_{29}$ is P, and $X_{37}$ is trans-Hyp; and the linker is:

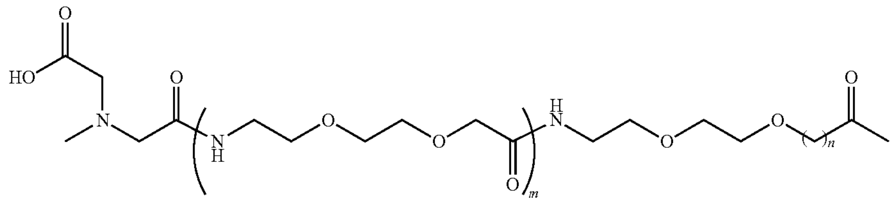
,
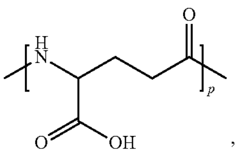
,
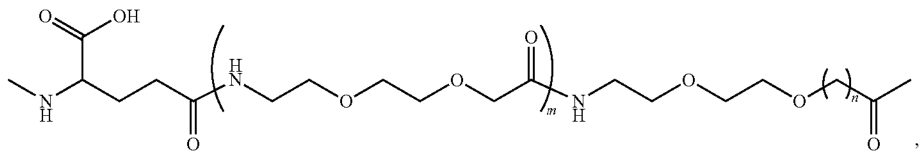
, or
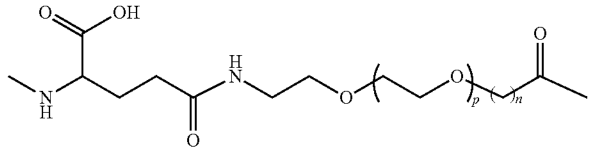

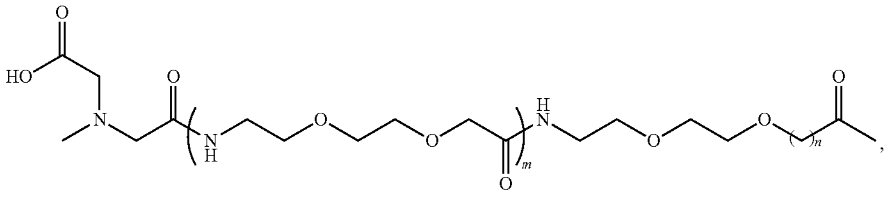,

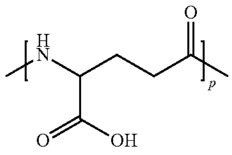

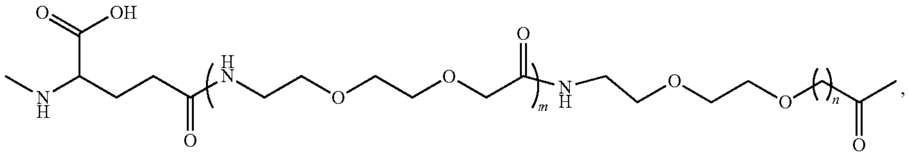, or

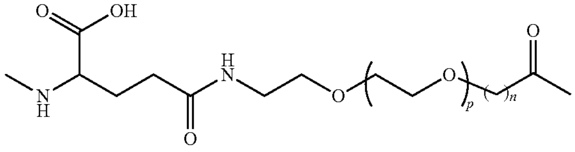

wherein m is 1 or 2; n is 1 or 2; p is any integer from 1 to 5; and the extension part is

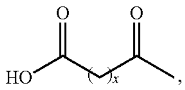, wherein x is any integer from 4 to 38.

Preferably, the amino acid sequence of the polypeptide analog comprises an amino acid sequence as shown in formula (I):

(SEQ ID NO: 115)
$X_1$CNTATCATQRLA$X_{14}$FL$X_{17}$H$X_{19}X_{20}X_{21}X_{22}X_{23}X_{24}X_{25}$IL$X_{28}$ $X_{29}$TNVGS$X_{35}$T$X_{37}$ formula (I), $X_1$ is selected from K, D, Dab, Dap, E, H, Har, Orn or R, or deleted, $X_{14}$ is selected from N, Aad, Dab, Dap, E or D, $X_{17}$ is selected from V, Orn or R, $X_{23}$ is selected from F, L or K, $X_{24}$ is selected from G, R, H, P, D, N, S, K, αK, Dap, Dab, Orn, Cit, Sar, Trx or AOC, $X_{25}$ is selected from A, K or P, $X_{28}$ is selected from S or P, $X_{29}$ is selected from S or P, and $X_{37}$ is selected from P or trans-Hyp; and the linker is:

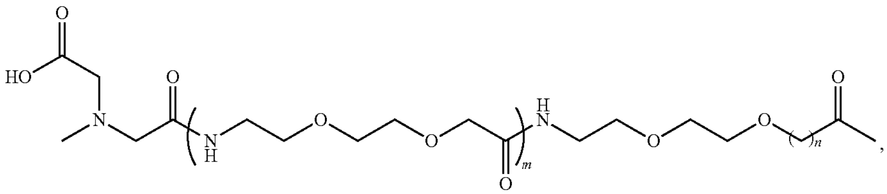,

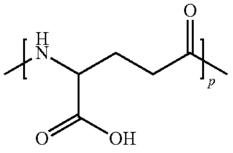

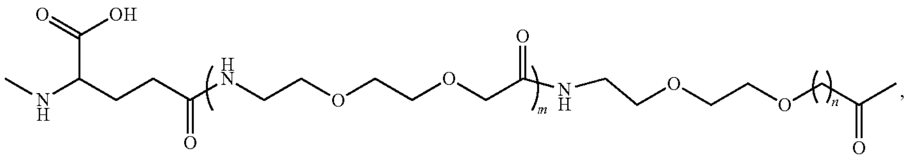, or

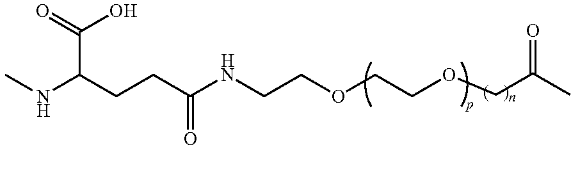

wherein m is 1 or 2; n is 1 or 2; p is any integer from 1 to 5; and the extension part is

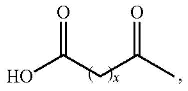

wherein x is any integer from 4 to 38.

Preferably, the amino acid sequence of the polypeptide analog comprises an amino acid sequence as shown in formula (I):

(SEQ ID NO: 116)
$X_1CNTATCATQRLAX_{14}FLX_{17}HX_{19}X_{20}X_{21}X_{22}X_{23}X_{24}X_{25}ILX_{28}X_{29}TNVGSX_{35}TX_{37}$ formula (I), $X_1$ is selected from K or R, $X_{14}$ is selected from N, Aad, Dab, Dap, E or D, $X_{17}$ is selected from V, Orn or R, $X_{23}$ is selected from F, L or K, $X_{24}$ is selected from G, R or K, $X_{25}$ is selected from A, K or P, $X_{28}$ is selected from S or P, $X_{29}$ is selected from S or P, and $X_{37}$ is selected from P or trans-Hyp; and the linker is:

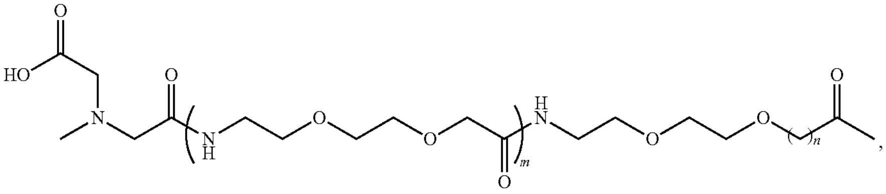
,
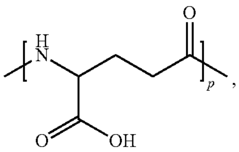
,
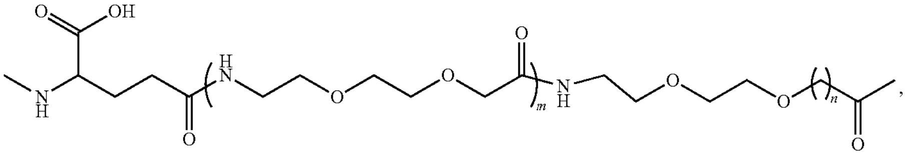
, or
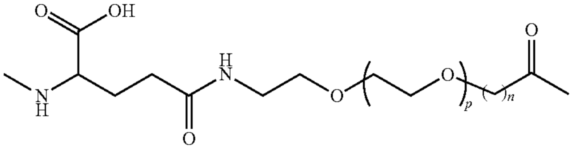

wherein m is 1 or 2; n is 1 or 2; p is any integer from 1 to 5; and the extension part is

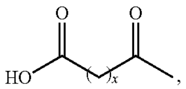

wherein x is any integer from 4 to 38.

In some embodiments, the polypeptide analog derivative of the present disclosure is selected from the following compounds as shown in Table 2, wherein PD065 is a Cagrilintide.

TABLE 2

| Name of compound | Sequence of polypeptide | Modification site | Fatty acid-containing side chain | SEQ ID NO |
|---|---|---|---|---|
| PD001 | RCNTATCATQRLAEFLRHSSKNLGPILPPTNVGSNTP-$NH_2$ | 21K | 2*AEEA + γGlu + C20 diacid | 117 |
| PD002 | RCNTATCATQRLAEFLRHSSNKLGPILPPTNVGSNTP-$NH_2$ | 22K | 2*AEEA + γGlu + C20 diacid | 118 |
| PD003 | RCNTATCATQRLAEFLRHSSNNKGPILPPTNVGSNTP-$NH_2$ | 23K | 2*AEEA + γGlu + C20 diacid | 119 |
| PD004 | RCNTATCATQRLAEFLRHSSNNLKPILPPTNVGSNTP-$NH_2$ | 24K | 2*AEEA + γGlu + C20 diacid | 120 |
| PD005 | RCNTATCATQRLAEFLRHSSNNLGKILPPTNVGSNTP-$NH_2$ | 25K | 2*AEEA + γGlu + C20 diacid | 121 |

TABLE 2-continued

| Name of compound | Sequence of polypeptide | Modification site | Fatty acid-containing side chain | SEQ ID NO |
|---|---|---|---|---|
| PD006 | RCNTATCATQRLAEFLRHSSKNLGPILPPTNVGSNTP-$NH_2$ | 21K | γGlu + C20 diacid | 122 |
| PD007 | RCNTATCATQRLAEFLRHSSNKLGPILPPTNVGSNTP-$NH_2$ | 22K | γGlu + C20 diacid | 123 |
| PD008 | RCNTATCATQRLAEFLRHSSNNKGPILPPTNVGSNTP-$NH_2$ | 23K | γGlu + C20 diacid | 124 |
| PD009 | RCNTATCATQRLAEFLRHSSNNLKPILPPTNVGSNTP-$NH_2$ | 24K | γGlu + C20 diacid | 125 |
| PD010 | RCNTATCATQRLAEFLRHSSNNLGKILPPTNVGSNTP-$NH_2$ | 25K | γGlu + C20 diacid | 126 |
| PD011 | RCNTATCATQRLAEFLRHSSNNLKPILSSTNVGSNTP-$NH_2$ | 24K | γGlu + C20 diacid | 127 |
| PD012 | RCNTATCATQRLAEFLRHSSNNLKAILPSTNVGSNTP-$NH_2$ | 24K | γGlu + C20 diacid | 128 |
| PD013 | RCNTATCATQRLAEFLRHSSNNLKAILSPTNVGSNTP-$NH_2$ | 24K | γGlu + C20 diacid | 129 |
| PD014 | RCNTATCATQRLAEFLRHSSNNLKPILPSTNVGSNTP-$NH_2$ | 24K | γGlu + C20 diacid | 130 |
| PD015 | RCNTATCATQRLAEFLRHSSNNLKPILSPTNVGSNTP-$NH_2$ | 24K | γGlu + C20 diacid | 131 |
| PD016 | RCNTATCATQRLAEFLRHSSNNLKAILPPTNVGSNTP-$NH_2$ | 24K | γGlu + C20 diacid | 132 |
| PD017 | RCNTATCATQRLAEFLRHSSNNLKPILPPTNVGSNTY-$NH_2$ | 24K | γGlu + C20 diacid | 133 |
| PD018 | RCNTATCATQRLAEFLRHSSNNLKAILSSTNVGSNTY-$NH_2$ | 24K | γGlu + C20 diacid | 134 |
| PD019 | RCNTATCATQRLAEFLRHSSNNLKPILSSTNVGSNTY-$NH_2$ | 24K | γGlu + C20 diacid | 135 |
| PD020 | RCNTATCATQRLAEFLRHSSNNLKAILPSTNVGSNTY-$NH_2$ | 24K | γGlu + C20 diacid | 136 |
| PD021 | RCNTATCATQRLAEFLRHSSNNLKAILSPTNVGSNTY-$NH_2$ | 24K | γGlu + C20 diacid | 137 |
| PD022 | RCNTATCATQRLAEFLRHSSNNLKPILPSTNVGSNTY-$NH_2$ | 24K | γGlu + C20 diacid | 138 |
| PD023 | RCNTATCATQRLAEFLRHSSNNLKPILSPTNVGSNTY-$NH_2$ | 24K | γGlu + C20 diacid | 139 |
| PD024 | RCNTATCATQRLAEFLRHSSNNLKAILPPTNVGSNTY-$NH_2$ | 24K | γGlu + C20 diacid | 140 |
| PD025 | RCNTATCATQRLAEFLRHSSNNLKPILPPTNVGSGTP-$NH_2$ | 24K | γGlu + C20 diacid | 141 |
| PD026 | RCNTATCATQRLAEFLRHSSNNLKAILSSTNVGSGTP-$NH_2$ | 24K | γGlu + C20 diacid | 142 |
| PD027 | RCNTATCATQRLAEFLRHSSNNLKPILSSTNVGSGTP-$NH_2$ | 24K | γGlu + C20 diacid | 143 |
| PD028 | RCNTATCATQRLAEFLRHSSNNLKAILPSTNVGSGTP-$NH_2$ | 24K | γGlu + C20 diacid | 144 |
| PD029 | RCNTATCATQRLAEFLRHSSNNLKAILSPTNVGSGTP-$NH_2$ | 24K | γGlu + C20 diacid | 145 |
| PD030 | RCNTATCATQRLAEFLRHSSNNLKPILPSTNVGSGTP-$NH_2$ | 24K | γGlu + C20 diacid | 146 |

TABLE 2-continued

| Name of compound | Sequence of polypeptide | Modification site | Fatty acid-containing side chain | SEQ ID NO |
|---|---|---|---|---|
| PD031 | RCNTATCATQRLAEFLRHSSNNLKPILSPTNV GSGTP-$NH_2$ | 24K | γGlu + C20 diacid | 147 |
| PD032 | RCNTATCATQRLAEFLRHSSNNLKAILPPTN VGSGTP-$NH_2$ | 24K | γGlu + C20 diacid | 148 |
| PD033 | KCNTATCATQRLAEFLRHSSNNLKPILPPTN VGSNTP-$NH_2$ | 24K | γGlu + C20 diacid | 149 |
| PD034 | KCNTATCATQRLAEFLRHSSNNLKPILSSTN VGSNTP-$NH_2$ | 24K | γGlu + C20 diacid | 150 |
| PD035 | KCNTATCATQRLAEFLRHSSNNLKAILPSTN VGSNTP-$NH_2$ | 24K | γGlu + C20 diacid | 151 |
| PD036 | KCNTATCATQRLAEFLRHSSNNLKAILSPTN VGSNTP-$NH_2$ | 24K | γGlu + C20 diacid | 152 |
| PD037 | KCNTATCATQRLAEFLRHSSNNLKPILPSTN VGSNTP-$NH_2$ | 24K | γGlu + C20 diacid | 153 |
| PD038 | KCNTATCATQRLAEFLRHSSNNLKPILSPTN VGSNTP-$NH_2$ | 24K | γGlu + C20 diacid | 154 |
| PD039 | KCNTATCATQRLAEFLRHSSNNLKAILPPTN VGSNTP-$NH_2$ | 24K | γGlu + C20 diacid | 155 |
| PD040 | RCNTATCATQRLAEFLRHSSNNLKPILPPTNV GSNT-trans-Hyp-$NH_2$ | 24K | γGlu + C20 diacid | 156 |
| PD041 | RCNTATCATQRLAEFLRHSSNNLKPILPPTNV GSGT-trans-Hyp-$NH_2$ | 24K | γGlu + C20 diacid | 157 |
| PD042 | RCNTATCATQRLADFLRHSSNNLKPILPPTN VGSNTP-$NH_2$ | 24K | γGlu + C20 diacid | 158 |
| PD043 | RCNTATCATQRLA-Aad-FLRHSSNNLKPILPP TNVGSNTP-$NH_2$ | 24K | γGlu + C20 diacid | 159 |
| PD044 | RCNTATCATQRLA-Dab-FLRHSSNNLKPILPP TNVGSNTP-$NH_2$ | 24K | γGlu + C20 diacid | 160 |
| PD045 | RCNTATCATQRLA-Dap-FLRHSSNNLKPILPP TNVGSNTP-$NH_2$ | 24K | γGlu + C20 diacid | 161 |
| PD046 | RCNTATCATQRLAEFL-Orn-HSSNNLKPILPP TNVGSNTP-$NH_2$ | 24K | γGlu + C20 diacid | 162 |
| PD047 | RCNTATCATQRLAEFLRHSSNNLKPILPPTNV GSNTP-$NH_2$ | 24K | γGlu + C20 diacid | 125 |
| PD048 | RCNTATCATQRLADFLRHSSNNLKPILPPTN VGSNTP-$NH_2$ | 24K | γGlu + C20 diacid | 158 |
| PD049 | CNTATCATORLAEFLRHSSNNLKPILPPTNV GSNTP-$NH_2$ | 23K | γGlu + C20 diacid | 163 |
| PD050 | CNTATCATQRLADFLRHSSNNLKPILPPTNV GSNTP-$NH_2$ | 23K | γGlu + C20 diacid | 164 |
| PD051 | RCNTATCATQRLAEFLRHSSNNLKPILPPTNV GSNT-trans-Hyp-$NH_2$ | 24K | γGlu + C20 diacid | 156 |
| PD052 | RCNTATCATQRLADFLRHSSNNLKPILPPTN VGSNT-trans-Hyp-$NH_2$ | 24K | γGlu + C20 diacid | 165 |
| PD053 | CNTATCATQRLAEFLRHSSNNLKPILPPTNV GSNT-trans-Hyp-$NH_2$ | 23K | γGlu + C20 diacid | 166 |
| PD054 | CNTATCATQRLADFLRHSSNNLKPILPPTNV GSNT-trans-Hyp-$NH_2$ | 23K | γGlu + C20 diacid | 167 |
| PD055 | RCNTATCATQRLAEFLRHSSNNLKPILPPTNV GSNT-cis-Hyp-$NH_2$ | 24K | γGlu + C20 diacid | 168 |

TABLE 2-continued

| Name of compound | Sequence of polypeptide | Modification site | Fatty acid-containing side chain | SEQ ID NO |
|---|---|---|---|---|
| PD056 | RCNTATCATQRLADFLRHSSNNLKPILPPTN VGSNT-cis-Hyp-$NH_2$ | 24K | γGlu + C20 diacid | 169 |
| PD057 | RCNTATCATQRLAEFLRHSSNNLKPILPPTNV GSNT-Pip-$NH_2$ | 24K | γGlu + C20 diacid | 170 |
| PD058 | RCNTATCATQRLADFLRHSSNNLKPILPPTN VGSNT-Pip-$NH_2$ | 24K | γGlu + C20 diacid | 171 |
| PD059 | RCNTATCATQRLAEFLRHSSNNLKPILPPTNV GSNT-Aze-$NH_2$ | 24K | γGlu + C20 diacid | 172 |
| PD060 | RCNTATCATQRLADFLRHSSNNLKPILPPTN VGSNT-Aze-$NH_2$ | 24K | γGlu + C20 diacid | 173 |
| PD061 | RCNTATCATQRLAEFLRHSSNNLKPILPPTNV GSNT-$_3$-Am-Pro-$NH_2$ | 24K | γGlu + C20 diacid | 174 |
| PD062 | RCNTATCATQRLADFLRHSSNNLKPILPPTN VGSNT-$_3$-Am-Pro-$NH_2$ | 24K | γGlu + C20 diacid | 175 |
| PD063 | RCNTATCATQRLAEFLRHSSNNLKPILPPTNV GSNT-aMePro-$NH_2$ | 24K | γGlu + C20 diacid | 176 |
| PD064 | RCNTATCATQRLADFLRHSSNNLKPILPPTN VGSNT-aMePro-$NH_2$ | 24K | γGlu + C20 diacid | 177 |
| PD065 | KCNTATCATQRLAEFLRHSSNNFGPILPPTNV GSNTP-$NH_2$ | N-terminal | γGlu + C20 diacid | 178 |
| PD066 | KCNTATCATQRLAEFLRHSSNNFGPILPPTNV GSNTP-$NH_2$ | 1K-ϵ amino | γGlu + C20 diacid | 179 |
| PD067 | KCNTATCATQRLADFLRHSSNNFGPILPPTN VGSNT-trans-Hyp-$NH_2$ | N-terminal | γGlu + C20 diacid | 180 |
| PD068 | KCNTATCATQRLADFLRHSSNNFGPILPPTN VGSNT-trans-Hyp-$NH_2$ | 1K-ϵ amino | γGlu + C20 diacid | 181 |
| PD069 | KCNTATCATQRLADFLRHSSNNLGPILPPTN VGSNT-trans-Hyp-$NH_2$ | N-terminal | γGlu + C20 diacid | 182 |
| PD070 | KCNTATCATQRLADFLRHSSNNLGPILPPTN VGSNT-trans-Hyp-$NH_2$ | 1K-ϵ amino | γGlu + C20 diacid | 183 |
| PD071 | KCNTATCATQRLADFLRHSSNNLKPILPPTN VGSNT-trans-Hyp-$NH_2$ | N-terminal | γGlu + C20 diacid | 184 |
| PD072 | KCNTATCATQRLADFLRHSSNNLKPILPPTN VGSNT-trans-Hyp-$NH_2$ | 1K-ϵ amino | γGlu + C20 diacid | 185 |
| PD073 | Dap-CNTATCATQRLADFLRHSSNNLKPILPPT NVGSNT-trans-Hyp-$NH_2$ | 24K | γGlu + C20 diacid | 186 |
| PD074 | Dab-CNTATCATQRLADFLRHSSNNLKPILPPT NVGSNT-trans-Hyp-$NH_2$ | 24K | γGlu + C20 diacid | 187 |
| PD075 | Orn-CNTATCATQRLADFLRHSSNNLKPILPPT NVGSNT-trans-Hyp-$NH_2$ | 24K | γGlu + C20 diacid | 188 |
| PD076 | KCNTATCATQRLADFLRHSSNNLKPILPPTN VGSNT-trans-Hyp-$NH_2$ | 24K | γGlu + C20 diacid | 189 |
| PD077 | Har-CNTATCATQRLADFLRHSSNNLKPILPPT NVGSNT-trans-Hyp-$NH_2$ | 24K | γGlu + C20 diacid | 190 |
| PD078 | HCNTATCATQRLADFLRHSSNNLKPILPPTN VGSNT-trans-Hyp-$NH_2$ | 24K | γGlu + C20 diacid | 191 |
| PD079 | DCNTATCATQRLADFLRHSSNNLKPILPPTN VGSNT-trans-Hyp-$NH_2$ | 24K | γGlu + C20 diacid | 192 |
| PD080 | ECNTATCATQRLADFLRHSSNNLKPILPPTN VGSNT-trans-Hyp-$NH_2$ | 24K | γGlu + C20 diacid | 193 |
| PD081 | RCNTATCATQRLADFLRHSSNNLKPILPPTN VGSNT-trans-Hyp-$NH_2$ | 24K | 2*AEEA + γGlu + C20 diacid | 194 |

TABLE 2-continued

| Name of compound | Sequence of polypeptide | Modification site | Fatty acid-containing side chain | SEQ ID NO |
|---|---|---|---|---|
| PD082 | RCNTATCATQRLADFLRHSSNNKGPILPPTN VGSNT-trans-Hyp-$NH_2$ | 23K | γGlu + C20 diacid | 195 |
| PD083 | RCNTATCATQRLADFLRHSSNNKGPILPPTN VGSNT-trans-Hyp-$NH_2$ | 23K | 2*AEEA + γGlu + C20 diacid | 196 |
| PD084 | RCNTATCATQRLADFLRHSSNNKGPILPPTN VGSNT-trans-Hyp-$NH_2$ | 23K | γGlu + C18 diacid | 197 |
| PD085 | RCNTATCATQRLADFLRHSSNNKGPILPPTN VGSNT-trans-Hyp-$NH_2$ | 23K | 2*AEEA + γGlu + C18 diacid | 198 |
| PD086 | RCNTATCATQRLADFLRHSSNKLGPILPPTN VGSNT-trans-Hyp-$NH_2$ | 22K | γGlu + C20 diacid | 199 |
| PD087 | RCNTATCATQRLADFLRHSSNKLGPILPPTN VGSNT-trans-Hyp-$NH_2$ | 22K | 2*AEEA + γGlu + C20 diacid | 200 |
| PD088 | RCNTATCATQRLADFLRHSSNKLGPILPPTN VGSNT-trans-Hyp-$NH_2$ | 22K | γGlu + C18 diacid | 201 |
| PD089 | RCNTATCATQRLADFLRHSSNKLGPILPPTN VGSNT-trans-Hyp-$NH_2$ | 22K | 2*AEEA + γGlu + C18 diacid | 202 |
| PD090 | RCNTATCATQRLADFLRHSSKNLGPILPPTN VGSNT-trans-Hyp-$NH_2$ | 21K | γGlu + C20 diacid | 203 |
| PD091 | RCNTATCATQRLADFLRHSSKNLGPILPPTN VGSNT-trans-Hyp-$NH_2$ | 21K | 2*AEEA + γGlu + C20 diacid | 204 |
| PD092 | RCNTATCATQRLADFLRHSSKNLGPILPPTN VGSNT-trans-Hyp-$NH_2$ | 21K | γGlu + C18 diacid | 205 |
| PD093 | RCNTATCATQRLADFLRHSSKNLGPILPPTN VGSNT-trans-Hyp-$NH_2$ | 21K | 2*AEEA + γGlu + C18 diacid | 206 |
| PD094 | RCNTATCATQRLADFLRHSKNNLGPILPPTN VGSNT-trans-Hyp-$NH_2$ | 20K | γGlu + C20 diacid | 207 |
| PD095 | RCNTATCATQRLADFLRHSKNNLGPILPPTN VGSNT-trans-Hyp-$NH_2$ | 20K | 2*AEEA + γGlu + C20 diacid | 208 |
| PD096 | RCNTATCATQRLADFLRHSKNNLGPILPPTN VGSNT-trans-Hyp-$NH_2$ | 20K | γGlu + C18 diacid | 209 |
| PD097 | RCNTATCATQRLADFLRHSKNNLGPILPPTN VGSNT-trans-Hyp-$NH_2$ | 20K | 2*AEEA + γGlu + C18 diacid | 210 |
| PD098 | RCNTATCATQRLADFLRHKSNNLGPILPPTN VGSNT-trans-Hyp-$NH_2$ | 19K | γGlu + C20 diacid | 211 |
| PD099 | RCNTATCATQRLADFLRHKSNNLGPILPPTN VGSNT-trans-Hyp-$NH_2$ | 19K | 2*AEEA + γGlu + C20 diacid | 212 |
| PD100 | RCNTATCATQRLADFLRHKSNNLGPILPPTN VGSNT-trans-Hyp-$NH_2$ | 19K | γGlu + C18 diacid | 213 |
| PD101 | RCNTATCATQRLADFLRHKSNNLGPILPPTN VGSNT-trans-Hyp-$NH_2$ | 19K | 2*AEEA + γGlu + C18 diacid | 214 |
| PD102 | RCNTATCATQRLADFLRHSSNNLGKILPPTN VGSNT-trans-Hyp-$NH_2$ | 25K | γGlu + C20 diacid | 215 |
| PD103 | RCNTATCATQRLADFLRHSSNNLGKILPPTN VGSNT-trans-Hyp-$NH_2$ | 25K | 2*AEEA + γGlu + C20 diacid | 216 |
| PD104 | RCNTATCATQRLADFLRHSSNNLGKILPPTN VGSNT-trans-Hyp-$NH_2$ | 25K | γGlu + C18 diacid | 217 |
| PD105 | RCNTATCATQRLADFLRHSSNNLGKILPPTN VGSNT-trans-Hyp-$NH_2$ | 25K | 2AEEA + γGlu + C18 diacid | 218 |
| PD106 | RCNTATCATQRLADFLRHSSNNLKPILPPTN VGSNT-trans-Hyp-$NH_2$ | 24K | AEEA + γGlu + C20 diacid | 219 |

TABLE 2-continued

| Name of compound | Sequence of polypeptide | Modification site | Fatty acid-containing side chain | SEQ ID NO |
|---|---|---|---|---|
| PD107 | RCNTATCATQRLADFLRHSSNNLKPILPPTN VGSNT-trans-Hyp-$NH_2$ | 24K | γGlu + C18 diacid | 220 |
| PD108 | RCNTATCATQRLADFLRHSSNNLKPILPPTN VGSNT-trans-Hyp-$NH_2$ | 24K | AEEA + γGlu + C18 diacid | 221 |
| PD109 | RCNTATCATQRLADFLRHSSNNLKPILPPTN VGSNT-trans-Hyp-$NH_2$ | 24K | 2*AEEA + γGlu + C18 diacid | 222 |
| PD110 | RCNTATCATQRLADFLRHSSNNKGPILPPTN VGSNT-trans-Hyp-$NH_2$ | 23K | AEEA + γGlu + C20 diacid | 223 |
| PD111 | RCNTATCATQRLADFLRHSSNNKGPILPPTN VGSNT-trans-Hyp-$NH_2$ | 23K | AEEA + γGlu + C18 diacid | 224 |
| PD112 | RCNTATCATQRLADFLRHSSNKLGPILPPTN VGSNT-trans-Hyp-$NH_2$ | 22K | AEEA + γGlu + C20 diacid | 225 |
| PD113 | RCNTATCATQRLADFLRHSSNKLGPILPPTN VGSNT-trans-Hyp-$NH_2$ | 22K | AEEA + γGlu + C18 diacid | 226 |
| PD114 | RCNTATCATQRLADFLRHSSKNLGPILPPTN VGSNT-trans-Hyp-$NH_2$ | 21K | AEEA + γGlu + C20 diacid | 227 |
| PD115 | RCNTATCATQRLADFLRHSSKNLGPILPPTN VGSNT-trans-Hyp-$NH_2$ | 21K | AEEA + γGlu + C18 diacid | 228 |
| PD116 | RCNTATCATQRLADFLRHSKNNLGPILPPTN VGSNT-trans-Hyp-$NH_2$ | 20K | AEEA + γGlu + C20 diacid | 229 |
| PD117 | RCNTATCATQRLADFLRHSKNNLGPILPPTN VGSNT-trans-Hyp-$NH_2$ | 20K | AEEA + γGlu + C18 diacid | 230 |
| PD118 | RCNTATCATQRLADFLRHKSNNLGPILPPTN VGSNT-trans-Hyp-$NH_2$ | 19K | AEEA + γGlu + C20 diacid | 231 |
| PD119 | RCNTATCATQRLADFLRHKSNNLGPILPPTN VGSNT-trans-Hyp-$NH_2$ | 19K | AEEA + γGlu + C18 diacid | 232 |
| PD120 | RCNTATCATQRLADFLRHSSNNLGKILPPTN VGSNT-trans-Hyp-$NH_2$ | 25K | AEEA + γGlu + C20 diacid | 233 |
| PD121 | RCNTATCATQRLADFLRHSSNNLGKILPPTN VGSNT-trans-Hyp-$NH_2$ | 25K | AEEA + γGlu + C18 diacid | 234 |
| PD122 | KCNTATCATQRLADFLRHSSNNLGPILPPTN VGSNT-trans-Hyp-$NH_2$ | N-terminal | AEEA + γGlu + C20 diacid | 235 |
| PD123 | KCNTATCATQRLADFLRHSSNNLGPILPPTN VGSNT-trans-Hyp-$NH_2$ | N-terminal | 2*AEEA + γGlu + C20 diacid | 236 |
| PD124 | KCNTATCATQRLADFLRHSSNNLGPILPPTN VGSNT-trans-Hyp-$NH_2$ | N-terminal | γGlu + C18 diacid | 237 |
| PD125 | KCNTATCATQRLADFLRHSSNNLGPILPPTN VGSNT-trans-Hyp-$NH_2$ | N-terminal | AEEA + γGlu + C18 diacid | 238 |
| PD126 | KCNTATCATQRLADFLRHSSNNLGPILPPTN VGSNT-trans-Hyp-$NH_2$ | N-terminal | 2*AEEA + γGlu + C18 diacid | 239 |
| PD127 | RCNTATCATQRLADFLRHSSNNLGPILPPTN VGSNT-trans-Hyp-$NH_2$ | N-terminal | γGlu + C20 diacid | 240 |
| PD128 | HCNTATCATQRLADFLRHSSNNLGPILPPTN VGSNT-trans-Hyp-$NH_2$ | N-terminal | γGlu + C20 diacid | 241 |
| PD129 | KCNTATCATQRLADFLRHSSNNLGPILPPTN VGSNT-trans-Hyp-$NH_2$ | N-terminal | C20 diacid | 242 |
| PD130 | KCNTATCATQRLADFLRHSSNNLGPILPPTN VGSNT-trans-Hyp-$NH_2$ | N-terminal | αGlu + C20 diacid | 243 |
| PD131 | KCNTATCATQRLADFLRHSSNNLGPILPPTN VGSNT-trans-Hyp-$NH_2$ | N-terminal | αAsp + C20 diacid | 244 |
| PD132 | KCNTATCATQRLADFLRHSSNNLGPILPPTN VGSNT-trans-Hyp-$NH_2$ | N-terminal | βAsp + C20 diacid | 245 |

TABLE 2-continued

| Name of compound | Sequence of polypeptide | Modification site | Fatty acid-containing side chain | SEQ ID NO |
|---|---|---|---|---|
| PD133 | KCNTATCATQRLADFLRHSSNNLGPILPPTN VGSNT-trans-Hyp-$NH_2$ | N-terminal | Trx + C20 diacid | 246 |
| PD134 | KCNTATCATQRLADFLRHSSNNLGPILPPTN VGSNT-trans-Hyp-$NH_2$ | N-terminal | Inp + C20 diacid | 247 |
| PD135 | KCNTATCATQRLADFLRHSSNNLGPILPPTN VGSNT-trans-Hyp-$NH_2$ | N-terminal, 1K-ϵ | γGlu + C10 diacid | 248 |
| PD136 | KCNTATCATQRLADFLRHSSNNLGPILPPTN VGSNT-trans-Hyp-$NH_2$ | N-terminal, 1K-ϵ | γGlu + C12 diacid | 249 |
| PD137 | KCNTATCATQRLADFLRHSSNNLGPILPPTN VGSNT-trans-Hyp-$NH_2$ | N-terminal, 1K-ϵ | γGlu + C14 diacid | 250 |
| PD138 | KCNTATCATQRLADFLRHSSNNLGPILPPTN VGSNT-trans-Hyp-$NH_2$ | N-terminal, 1K-ϵ | γGlu + C16 diacid | 251 |
| PD139 | KCNTATCATQRLADFLRHSSNNLGPILPPTN VGSNT-trans-Hyp-$NH_2$ | N-terminal, 1K-ϵ | γGlu + C18 diacid | 252 |
| PD140 | RCNTATCATQRLADFLRHSSNNLKPILPPTN VGSNT-trans-Hyp-$NH_2$ | N-terminal | γGlu + C20 diacid | 253 |
| PD141 | HCNTATCATQRLADFLRHSSNNLKPILPPTN VGSNT-trans-Hyp-$NH_2$ | N-terminal | γGlu + C20 diacid | 254 |
| PD142 | KCNTATCATQRLADFLRHSSNNLKPILPPTN VGSNT-trans-Hyp-$NH_2$ | N-terminal | C20 diacid | 255 |
| PD143 | KCNTATCATQRLADFLRHSSNNLKPILPPTN VGSNT-trans-Hyp-$NH_2$ | N-terminal | αGlu + C20 diacid | 256 |
| PD144 | KCNTATCATQRLADFLRHSSNNLKPILPPTN VGSNT-trans-Hyp-$NH_2$ | N-terminal | αAsp + C20 diacid | 257 |
| PD145 | KCNTATCATQRLADFLRHSSNNLKPILPPTN VGSNT-trans-Hyp-$NH_2$ | N-terminal | βAsp + C20 diacid | 258 |
| PD146 | KCNTATCATQRLADFLRHSSNNLKPILPPTN VGSNT-trans-Hyp-$NH_2$ | N-terminal | Trx + C20 diacid | 259 |
| PD147 | KCNTATCATQRLADFLRHSSNNLKPILPPTN VGSNT-trans-Hyp-$NH_2$ | N-terminal | Inp + C20 diacid | 260 |
| PD148 | KCNTATCATQRLADFLRHSSNNLKPILPPTN VGSNT-trans-Hyp-$NH_2$ | N-terminal, 1K-ϵ | γGlu + C10 diacid | 261 |
| PD149 | KCNTATCATQRLADFLRHSSNNLKPILPPTN VGSNT-trans-Hyp-$NH_2$ | N-terminal, 1K-ϵ | γGlu + C12 diacid | 262 |
| PD150 | KCNTATCATQRLADFLRHSSNNLKPILPPTN VGSNT-trans-Hyp-$NH_2$ | N-terminal, 1K-ϵ | γGlu + C14 diacid | 263 |
| PD151 | KCNTATCATQRLADFLRHSSNNLKPILPPTN VGSNT-trans-Hyp-$NH_2$ | N-terminal, 1K-ϵ | γGlu + C16 diacid | 264 |
| PD152 | KCNTATCATQRLADFLRHSSNNLKPILPPTN VGSNT-trans-Hyp-$NH_2$ | N-terminal, 1K-ϵ | γGlu + C18 diacid | 265 |
| PD153 | KCNTATCATQRLANFLVHSSNNFGPILPPTN VGSNTY-$NH_2$ | N-terminal | γGlu + C20 diacid | 266 |
| PD154 | KCNTATCATQ RLADFLRHSS NNLKPILPPT NVGSNT-Aze-$NH_2$ | N-terminal | γGlu + C20 diacid | 267 |
| PD155 | KCNTATCATQ RLADFLRHSS NNLGPILPPT NVGSNT-Aze-$NH_2$ | N-terminal | γGlu + C20 diacid | 268 |
| PD156 | KCNTATCATQ RLANFLVHSS NNFGPILPPT NVGSNTY-$NH_2$ | N-terminal | γGlu + C20 diacid | 266 |
| PD157 | KCNTATCATQ RLADFLRHSS NNLKPILPPT NVGSNT-Aze-$NH_2$ | N-terminal | γGlu + C20 diacid | 267 |

TABLE 2-continued

| Name of compound | Sequence of polypeptide | Modification site | Fatty acid-containing side chain | SEQ ID NO |
|---|---|---|---|---|
| PD158 | KCNTATCATQ RLADFLRHSS NNLRPILPPT NVGSNT-trans-Hyp-$NH_2$ | N-terminal | γGlu + C20 diacid | 269 |
| PD159 | KCNTATCATQ RLADFLRHSS NNLHPILPPT NVGSNT-trans-Hyp-$NH_2$ | N-terminal | γGlu + C20 diacid | 270 |
| PD160 | KCNTATCATQ RLADFLRHSS NNLKPILPPT NVGSNTP-$NH_2$ | N-terminal | γGlu + C20 diacid | 271 |
| PD161 | KCNTATCATQ RLADFLRHSS NNLRPILPPT NVGSNTP-$NH_2$ | N-terminal | γGlu + C20 diacid | 272 |
| PD162 | KCNTATCATQ RLADFLRHSS NNLHPILPPT NVGSNTP-$NH_2$ | N-terminal | γGlu + C20 diacid | 273 |
| PD163 | KCNTATCATQ RLADFLRHSS NNLPPILPPT NVGSNTP-$NH_2$ | N-terminal | γGlu + C20 diacid | 274 |
| PD164 | KCNTATCATQ RLADFLRHSS NNLDPILPPT NVGSNTP-$NH_2$ | N-terminal | γGlu + C20 diacid | 275 |
| PD165 | KCNTATCATQ RLADFLRHSS NNLNPILPPT NVGSNTP-$NH_2$ | N-terminal | γGlu + C20 diacid | 276 |
| PD166 | KCNTATCATQ RLADFLRHSS NNLSPILPPT NVGSNTP-$NH_2$ | N-terminal | γGlu + C20 diacid | 277 |
| PD167 | KCNTATCATQ RLADFLRHSS NNL-aK-PILPPT NVGSNTP-$NH_2$ | N-terminal | γGlu + C20 diacid | 278 |
| PD168 | KCNTATCATQ RLADFLRHSS NNL-Dap-PILPPT NVGSNTP-$NH_2$ | N-terminal | γGlu + C20 diacid | 279 |
| PD169 | KCNTATCATQ RLADFLRHSS NNL-Dab-PILPPT NVGSNTP-$NH_2$ | N-terminal | γGlu + C20 diacid | 280 |
| PD170 | KCNTATCATQ RLADFLRHSS NNL-Orn-PILPPT NVGSNTP-$NH_2$ | N-terminal | γGlu + C20 diacid | 281 |
| PD171 | KCNTATCATQ RLADFLRHSS NNL-Cit-PILPPT NVGSNTP-$NH_2$ | N-terminal | γGlu + C20 diacid | 282 |
| PD172 | KCNTATCATQ RLADFLRHSS NNL-Sar-PILPPT NVGSNTP-$NH_2$ | N-terminal | γGlu + C20 diacid | 283 |
| PD173 | KCNTATCATQ RLADFLRHSS NNL-Trx-PILPPT NVGSNTP-$NH_2$ | N-terminal | γGlu + C20 diacid | 284 |
| PD174 | KCNTATCATQ RLADFLRHSS NNL-AOC-PILPPT NVGSNTP-$NH_2$ | N-terminal | γGlu + C20 diacid | 285 |
| PD175 | KCNTATCATQ RLADFLRHSS NNLGPILPPT NVGSNT-Aze-$NH_2$ | N-terminal | γGlu + C20 diacid | 268 |
| PD176 | KCNTATCATQ RLADFLRHSS NNLKPILPPT NVGSNT-trans-Hyp-$NH_2$ | N-terminal | γGlu + 2*AEEA + C20 diacid | 286 |
| PD177 | KCNTATCATQ RLADFLRHSS NNLKPILPPT NVGSNT-trans-Hyp-$NH_2$ | N-terminal | 2*AEEA + Trx + C20 diacid | 287 |
| PD178 | KCNTATCATQ RLADFLRHSS NNLKPILPPT NVGSNT-trans-Hyp-$NH_2$ | N-terminal | Trx + 2*AEEA + C20 diacid | 288 |
| PD179 | KCNTATCATQ RLADFLRHSS NNLKPILPPT NVGSNT-trans-Hyp-$NH_2$ | N-terminal | 2*AEEA + Inp + C20 diacid | 289 |
| PD180 | KCNTATCATQ RLADFLRHSS NNLKPILPPT NVGSNT-trans-Hyp-$NH_2$ | N-terminal | Inp + 2*AEEA + C20 diacid | 290 |
| PD181 | KCNTATCATQ RLADFLRHSS NNLKPILPPT NVGSNT-trans-Hyp-$NH_2$ | N-terminal | 2*AEEA + αAsp + C20 diacid | 291 |
| PD182 | KCNTATCATQ RLADFLRHSS NNLKPILPPT NVGSNT-trans-Hyp-$NH_2$ | N-terminal | αAsp + 2*AEEA + C20 diacid | 292 |
| PD183 | KCNTATCATQ RLADFLRHSS NNLKPILPPT NVGSNT-trans-Hyp-$NH_2$ | N-terminal | 2*AEEA + βAsp + C20 diacid | 293 |

TABLE 2-continued

| Name of compound | Sequence of polypeptide | Modification site | Fatty acid-containing side chain | SEQ ID NO |
|---|---|---|---|---|
| PD184 | KCNTATCATQ RLADFLRHSS NNLKPILPPT NVGSNT-trans-Hyp-$NH_2$ | N-terminal | βAsp + 2*AEEA + C20 diacid | 294 |
| PD185 | KCNTATCATQ RLADFLRHSS NNLKPILPPT NVGSNT-trans-Hyp-$NH_2$ | N-terminal | 8*PEG + γGlu + C20 diacid | 295 |
| PD186 | KCNTATCATQ RLADFLRHSS NNLKPILPPT NVGSNT-trans-Hyp-$NH_2$ | N-terminal | γGlu + 8*PEG + C20 diacid | 296 |
| PD187 | KCNTATCATQ RLADFLRHSS NNLKPILPPT NVGSNT-trans-Hyp-$NH_2$ | N-terminal | 2*AEEA + C20 diacid | 297 |
| PD188 | KCNTATCATQ RLADFLRHSS NNLKPILPPT NVGSNTP-$NH_2$ | N-terminal | γGlu + 2*AEEA + C20 diacid | 298 |
| PD189 | KCNTATCATQ RLADFLRHSS NNLKPILPPT NVGSNTP-$NH_2$ | N-terminal | 2*AEEA + Trx + C20 diacid | 299 |
| PD190 | KCNTATCATQ RLADFLRHSS NNLKPILPPT NVGSNTP-$NH_2$ | N-terminal | Trx + 2*AEEA + C20 diacid | 300 |
| PD191 | KCNTATCATQ RLADFLRHSS NNLKPILPPT NVGSNTP-$NH_2$ | N-terminal | 2*AEEA + Inp + C20 diacid | 301 |
| PD192 | KCNTATCATQ RLADFLRHSS NNLKPILPPT NVGSNTP-$NH_2$ | N-terminal | Inp + 2*AEEA + C20 diacid | 302 |
| PD193 | KCNTATCATQ RLADFLRHSS NNLKPILPPT NVGSNTP-$NH_2$ | N-terminal | 2*AEEA + αAsp + C20 diacid | 303 |
| PD194 | KCNTATCATQ RLADFLRHSS NNLKPILPPT NVGSNTP-$NH_2$ | N-terminal | αAsp + 2*AEEA + C20 diacid | 304 |
| PD195 | KCNTATCATQ RLADFLRHSS NNLKPILPPT NVGSNTP-$NH_2$ | N-terminal | 2*AEEA + βAsp + C20 diacid | 305 |
| PD196 | KCNTATCATQ RLADFLRHSS NNLKPILPPT NVGSNTP-$NH_2$ | N-terminal | 2*AEEA + βAsp + C20 diacid | 306 |
| PD197 | RCNTA TCATQ RLADF LRHSS NNLRP ILPPT NVGSN TP-$NH_2$ | N-terminal | γGlu + C20 diacid | 307 |
| PD198 | KGGGG RCNTA TCATQ RLADF LRHSS NNLRP ILPPT NVGSN TP-$NH_2$ | N-terminal | γGlu + C20 diacid | 308 |

The compounds PD001 to PD198 represent polypeptide derivatives obtained by modifying the amino acid sequences with the fatty acid-containing side chains, wherein the fatty acid-containing side chain refers to the functional group capable of being used for coupling which is introduced into the amino acid side chain for modifying the amino acid in the present disclosure, such as the derivatives obtained by modifying sequences of corresponding polypeptides with corresponding fatty acid-containing side chains in Table 2. For example, the PD001 is a derivative obtained by modifying an amino acid K in a 21st position of the sequence RCNTATCATQRLAEFLRHSSKNLGPILPPTNVGSNTP-$NH_2$ (SEQ ID NO: 309) with the functional group capable of being used for coupling, that is, the side chain (2*AEEA+γGlu+C20 diacid). In general, C16 to C22 fatty diacid parts are located outside the fatty acid-containing side chain used for modification relative to the amino acid sequence, and at a far end of the side chain linked to the amino acid sequence.

In some embodiments, the polypeptide analog derivative of the present disclosure is preferably selected from the following derivatives: PD069, PD070, PD071, PD072, PD140, PD158, PD160, PD161, PD144, PD145, PD146, PD147 and PD187.

In some embodiments, the polypeptide analog derivative of the present disclosure is the compound PD069, and the PD069 has a structure below (SEQ ID NO: 182),

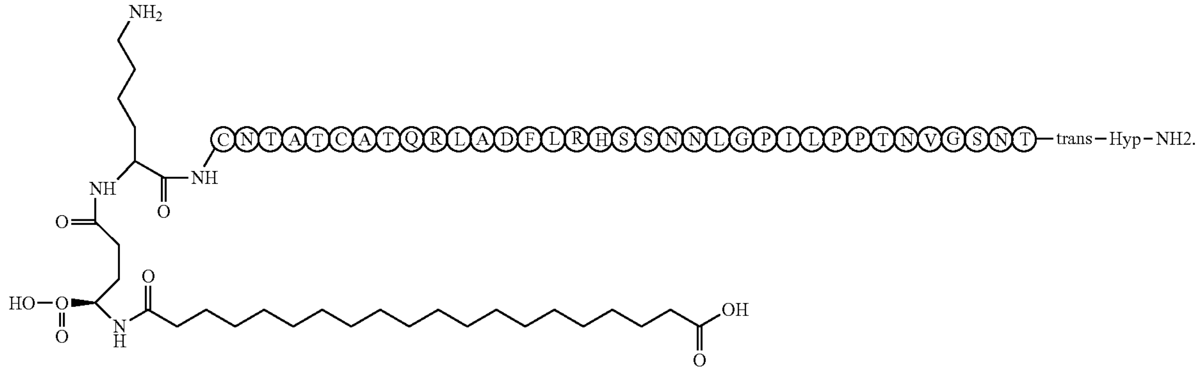

In some embodiments, the polypeptide analog derivative of the present disclosure is the compound PD070, and the PD070 has a structure below (SEQ ID NO: 183),

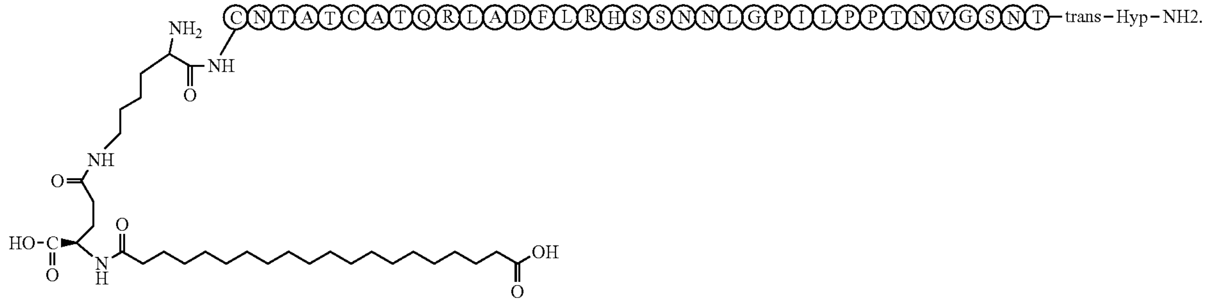

In some embodiments, the polypeptide analog derivative of the present disclosure is the compound PD071, and the PD071 has a structure below (SEQ ID NO: 184),

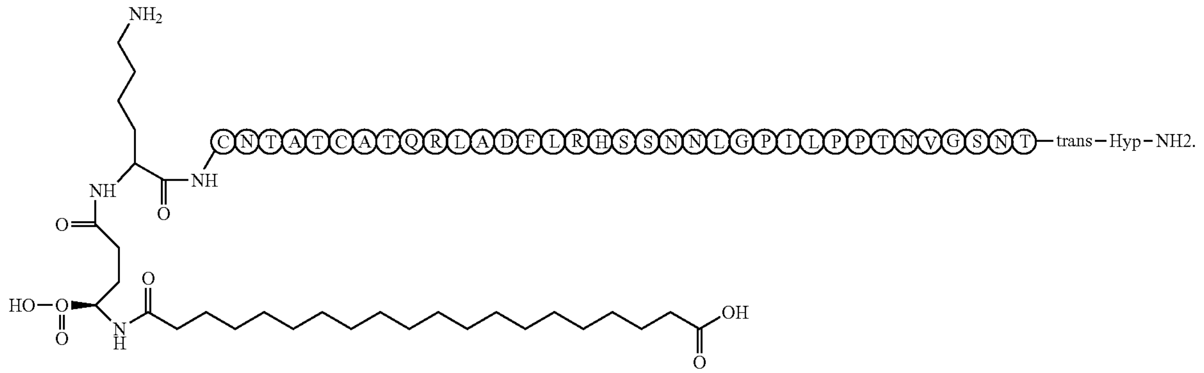

In some embodiments, the polypeptide analog derivative of the present disclosure is the compound PD072, and the PD072 has a structure below (SEQ ID NO: 185),

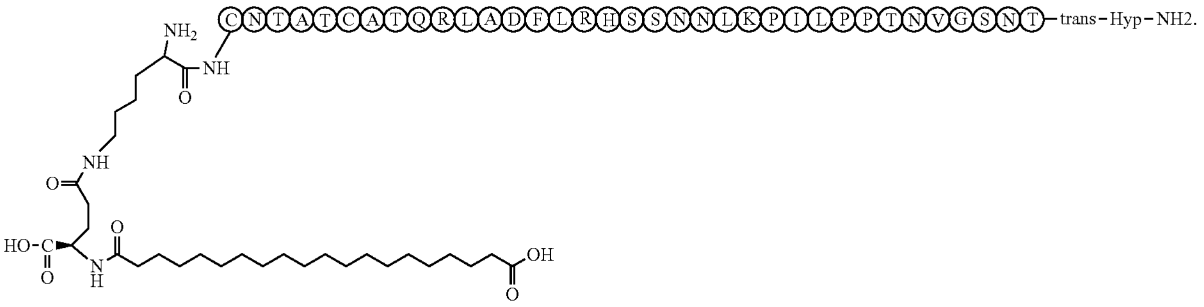

One aspect of the present disclosure further relates to a preparation method of the new amylin analog or the derivative thereof.

In some embodiments, the preparation of the new amylin analog or the derivative thereof may be implemented by conventional methods known to those skilled in the art. In general, a polypeptide molecule may be prepared by a chemical synthesis method or a biological fermentation method, or a combination of the two methods. For example, the polypeptide may be synthesized through a polypeptide gene sequence during synthesis, a corresponding polypeptide gene with a tag is inserted into a plasmid by a conventional method of genetic engineering to construct an expression plasmid, the expression plasmid is transferred into competent cells to construct expression cells, the expression cells containing a target polypeptide gene are screened, then cultured under suitable culture conditions, a culture product is collected, and a target polypeptide is finally obtained by a purification method. Further, an amino acid side chain of the target polypeptide may be modified by a chemical modification method, and the polypeptide analog derivative is obtained by purification.

In one aspect, the present disclosure further relates to a medicament or a pharmaceutical composition comprising the amylin analog or the derivative thereof above and a pharmaceutically acceptable salt of the above substance.

In some embodiments, the pharmaceutical composition of the present disclosure further comprises one or more oral delivery agents; preferably, the oral delivery agent is N-[8-(2-hydroxybenzoyl)amino]octanoic acid (NAC) salt; and further preferably, the oral delivery agent is PNAC, that is, potassium N-[8-(2-hydroxybenzoyl)amino]octanoate. The NAC salt or the PNAC salt of the oral delivery agent in the present disclosure should be understood as any crystal form capable of satisfying an oral delivery form of the composition of the present disclosure, such as the form in CN112661663B.

The PNAC salt has a structural formula (II) below:

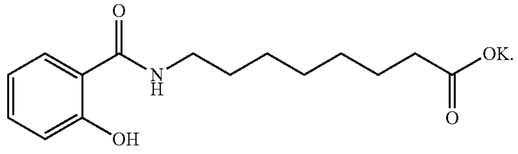

The NAC salt has a structural formula (I) below:

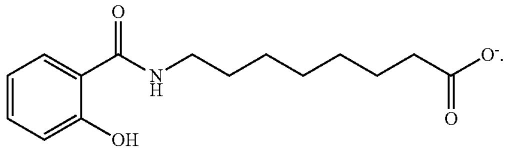

In some embodiments, the pharmaceutical composition of the present disclosure further comprises another or more pharmacologically active substances.

In some embodiments, the composition of the present disclosure further comprises a pharmaceutically acceptable excipient, preferably, the pharmaceutically acceptable excipient comprises, but is not limited to, one or more of a pharmaceutically acceptable carrier, a stabilizer, a dispersant, a cosolvent, a shaping agent, and the like. Generally, these substances are non-toxic, inert and pharmaceutically acceptable inactive substances.

In one aspect, the present disclosure provides use of the amylin analog or the derivative thereof, or the pharmaceutical composition above in preparation of a medicament for preventing and/or treating a disease, preferably, the use comprises a use in preparation of a medicament for preventing and/or treating an amylin receptor-related disease, and further preferably, the use comprises a use in preparation of a medicament for preventing and/or treating fat metabolism disorder, blood glucose metabolism disorder, a cardiovascular disease, a brain system disease, a mental system disease or a nervous system disease, comprising, but being not limited to, weight abnormality, hyperlipidemia, hypertension, arteriosclerosis, fatty liver, dyslipidemia, liver cirrhosis, a coronary heart disease, angina pectoris, myocardial infarction, an inflammatory bowel disease, dyspepsia and gastrointestinal ulcer, hyperglycemia, diabetes, impaired glucose tolerance, syndrome X, cognitive impairment, and stroke, preferably, the disease is the weight abnormality or the blood glucose metabolism disorder, and further preferably, the disease is the weight abnormality, comprising, but being not limited to, obesity or overweight.

In one aspect, the present disclosure provides a method for treating or/and preventing a disease, wherein the method comprises administering the amylin analog or the derivative thereof, the medicament or the pharmaceutical composition in the present disclosure to a subject in need, the disease is an amylin receptor-related disease, preferably, the disease is fat metabolism disorder, blood glucose metabolism disorder, a cardiovascular disease, a brain system disease, a mental system disease or a nervous system disease, comprising, but being not limited to, weight abnormality, hyperlipidemia, hypertension, arteriosclerosis, fatty liver, dyslipidemia, liver cirrhosis, a coronary heart disease, angina pectoris, myocardial infarction, an inflammatory bowel disease, dyspepsia and gastrointestinal ulcer, hyperglycemia, diabetes, impaired glucose tolerance, syndrome X, cognitive impairment, and stroke, further preferably, the disease is the weight abnormality or the blood glucose metabolism disorder, and more preferably, the disease is the weight abnormality, comprising, but being not limited to, obesity or overweight.

The amylin analog or the derivative thereof, the medicament or the pharmaceutical composition in the present disclosure may also be administered in combination with another or more pharmacologically active substances, the pharmacologically active substance comprises, but not is limited to, a body weight regulator, an anti-obesity agent, a lipid metabolism regulator, a blood glucose regulator, a hypertension therapeutic agent, a cardiovascular regulator, a brain system regulator, a mental system regulator or a nervous system regulator, preferably, the pharmacologically active substance is selected from: a GLP-1 receptor agonist (comprising, but being not limited to, GLP-1, a GLP-1 analog and a GLP-1 derivative), a GIP receptor agonist (comprising, but being not limited to, GIP, a GIP analog and a GIP derivative) and an insulin receptor agonist (comprising, but being not limited to, insulin, an insulin analog and an insulin derivative).

Effects of Invention

The polypeptide analog or the derivative thereof provided by the present disclosure has good agonistic activity on the insulin amyloid polypeptide receptor, has the characteristics of good stability, high activity, etc. at the same time, and can be used for treating and preventing diseases related to the insulin amyloid polypeptide receptor, such as body weight abnormality, especially obesity and overweight.

DESCRIPTION OF THE DRAWINGS

The drawings are used for better understanding of the present disclosure, and do not constitute improper limitations to the present disclosure. In the drawings.

EMBODIMENT

Figure 1:
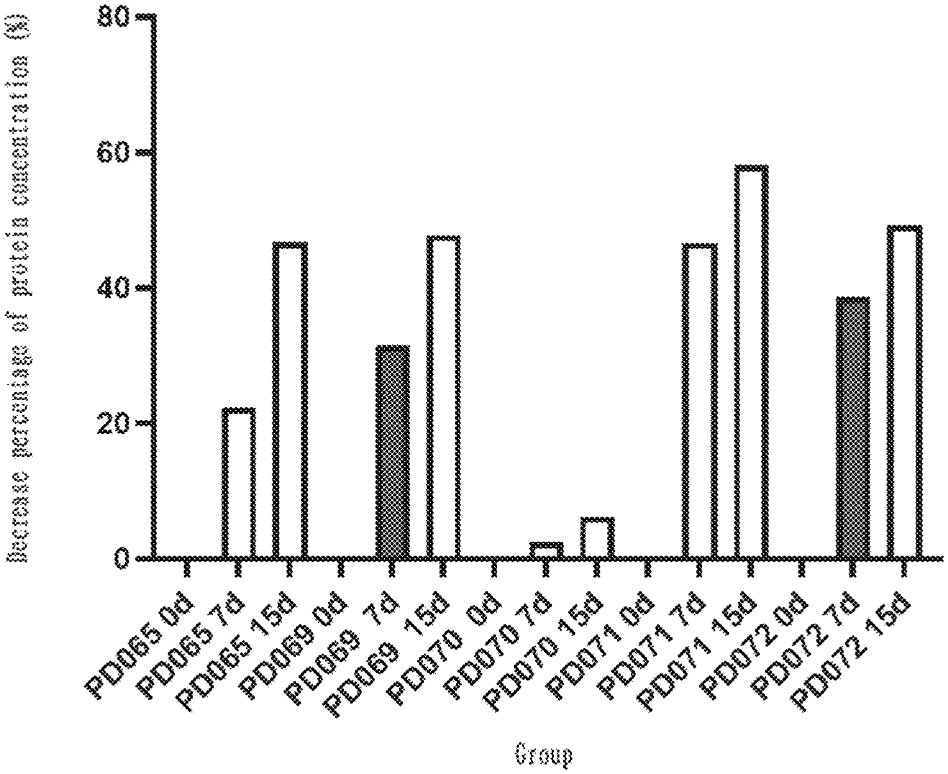
FIG. 1 shows stability experiment results of compounds PD065, PD069, PD070, PD071 and PD072 at 40° C. on the 0 day, the 7$^{th}$ day and the 15$^{th}$ day respectively.
Figure 2A:
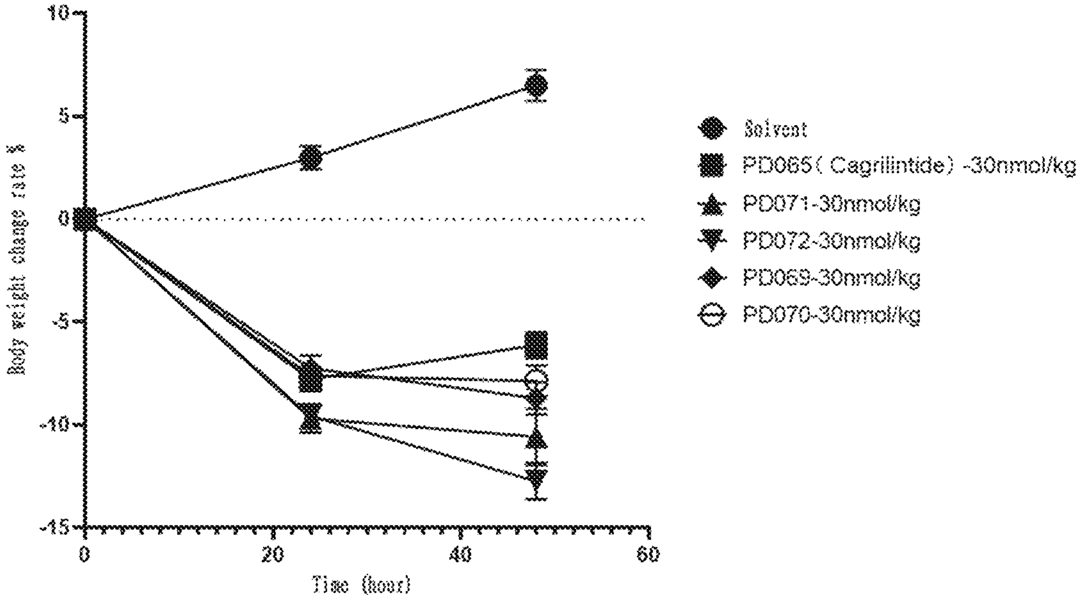
FIG. 2A shows change trends of weight loss effects of different derivatives in SD rats with time.
Figure 2B:
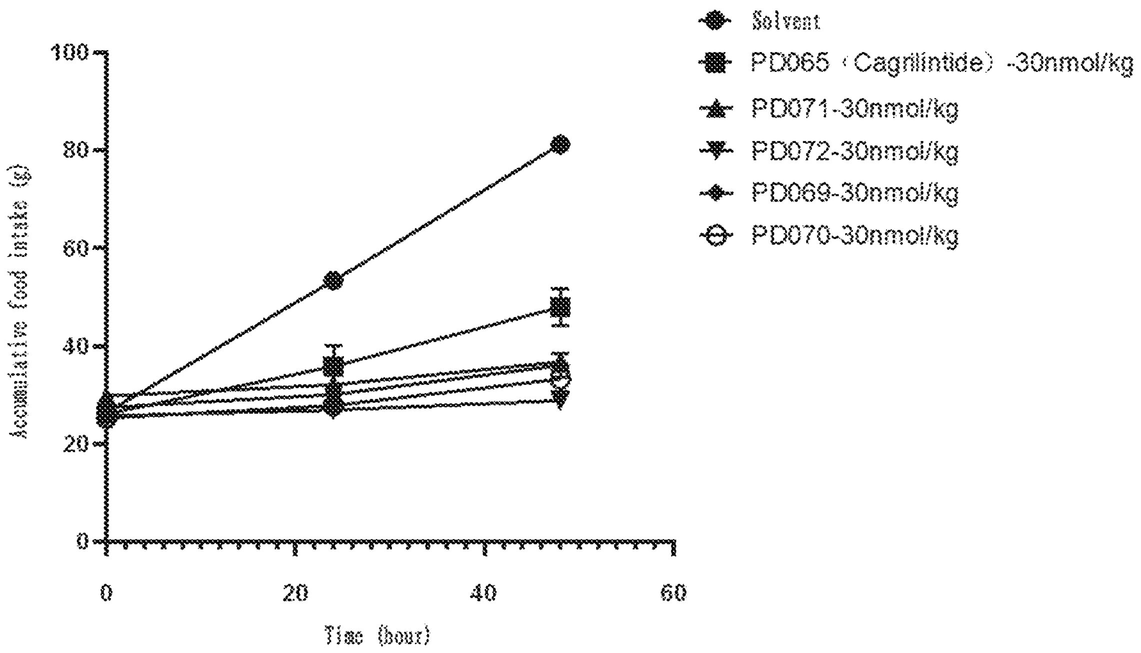
FIG. 2B shows change trends of influences of different derivatives on food intake in SD rats with time.
Figure 2C:
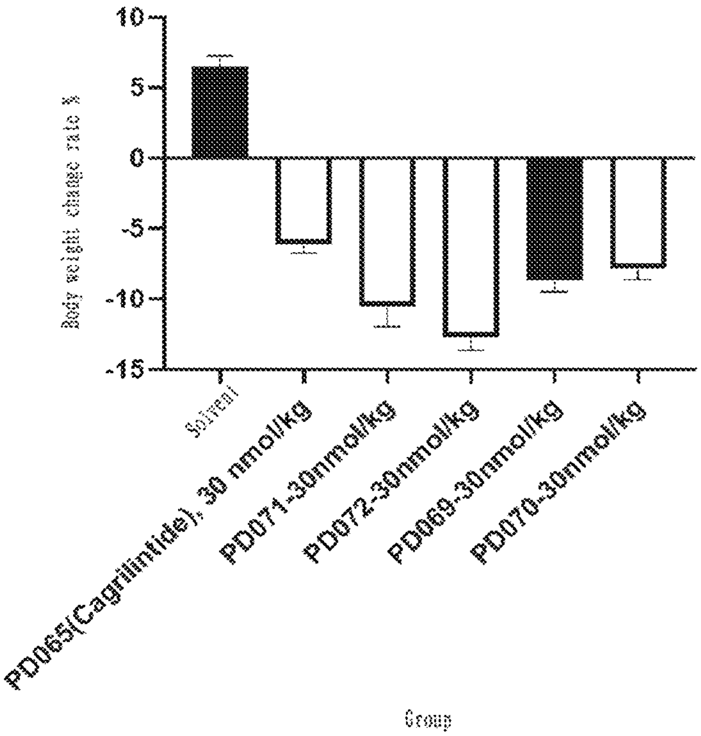
FIG. 2C shows weight change rates of SD rats in different derivative treatment groups in a group A at the 48th hour.
Figure 2D:
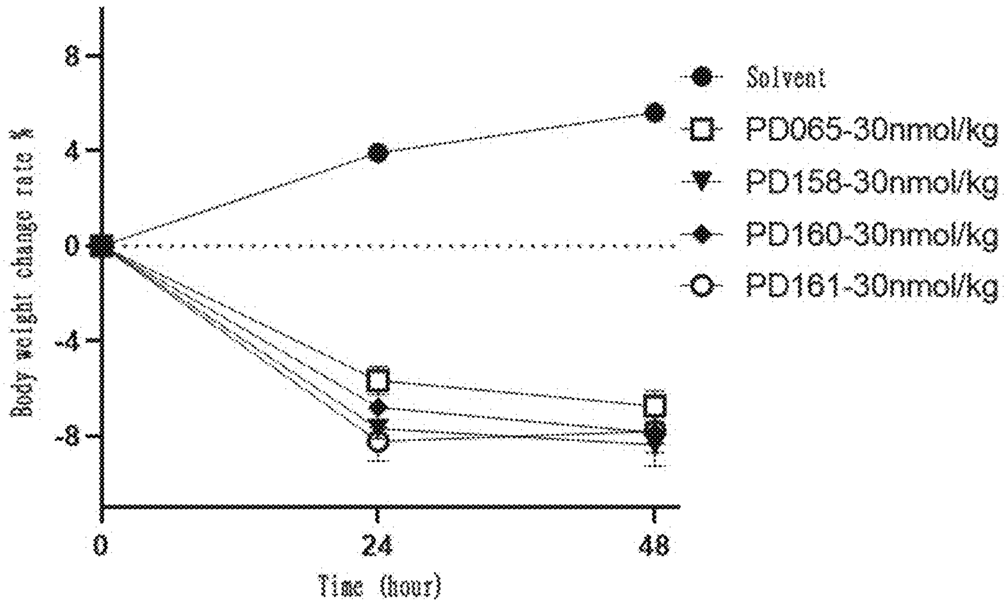
FIG. 2D shows weight change rates of SD rats in different derivative treatment groups in a group B at the 48th hour.
Figure 3A:
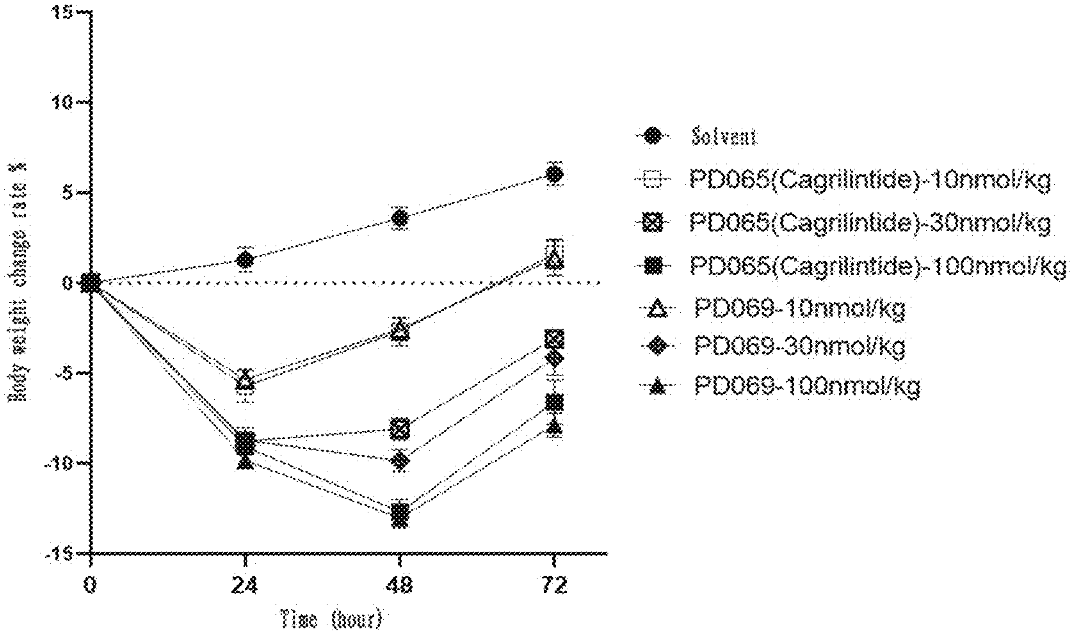
FIG. 3A shows change trends of weight loss effects of the compounds PD065 and PD069 at different concentrations in SD rats with time.
Figure 3B:
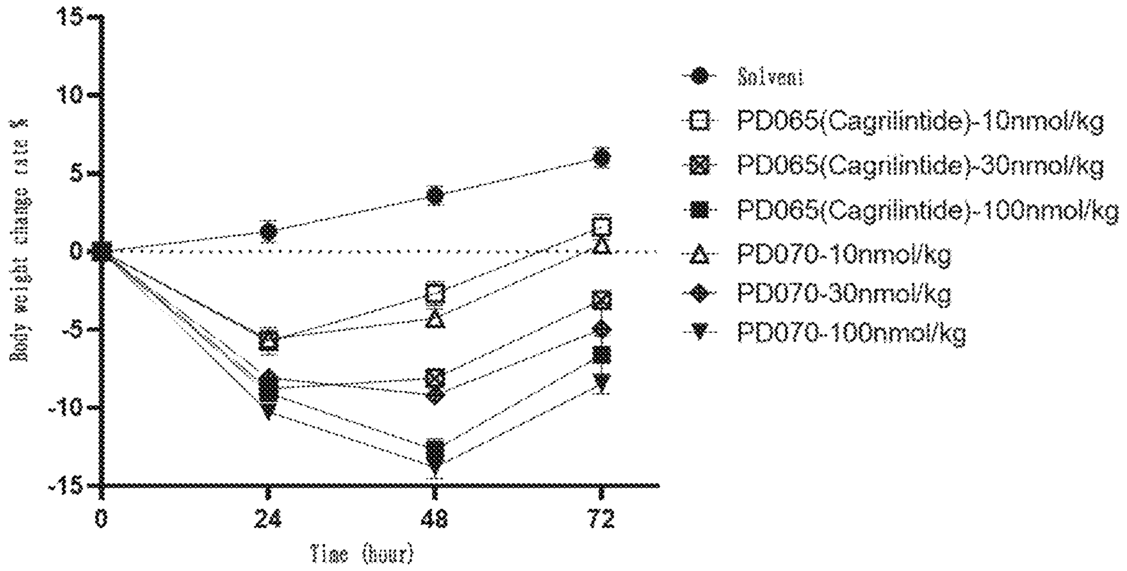
FIG. 3B shows change trends of weight loss effects of the compounds PD065 and PD070 at different concentrations in SD rats with time.
Figure 3C:
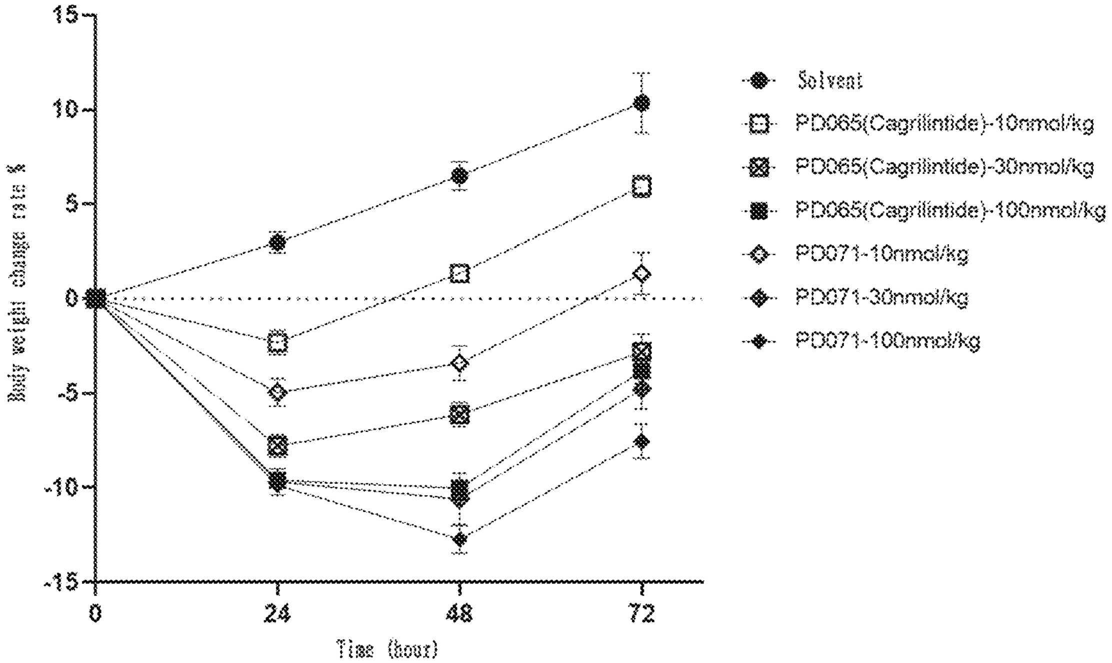
FIG. 3C shows change trends of weight loss effects of the compounds PD065 and PD071 at different concentrations in SD rats with time.
Figure 3D:
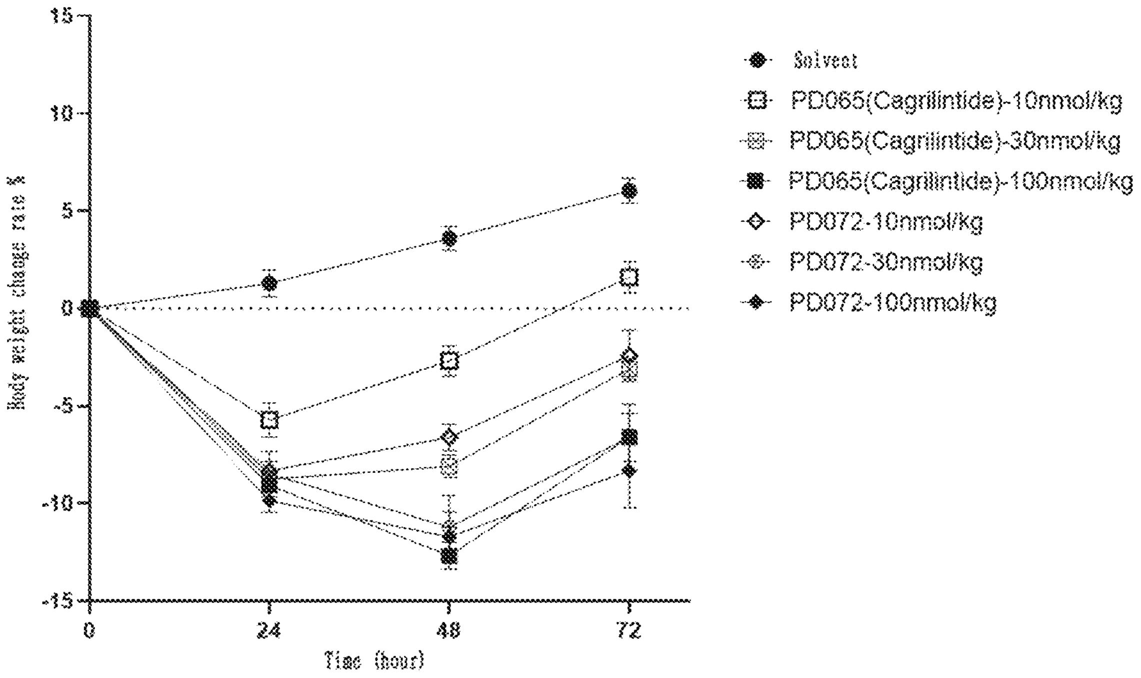
FIG. 3D shows change trends of weight loss effects of the compounds PD065 and PD072 at different concentrations in SD rats with time.
Figure 4A:
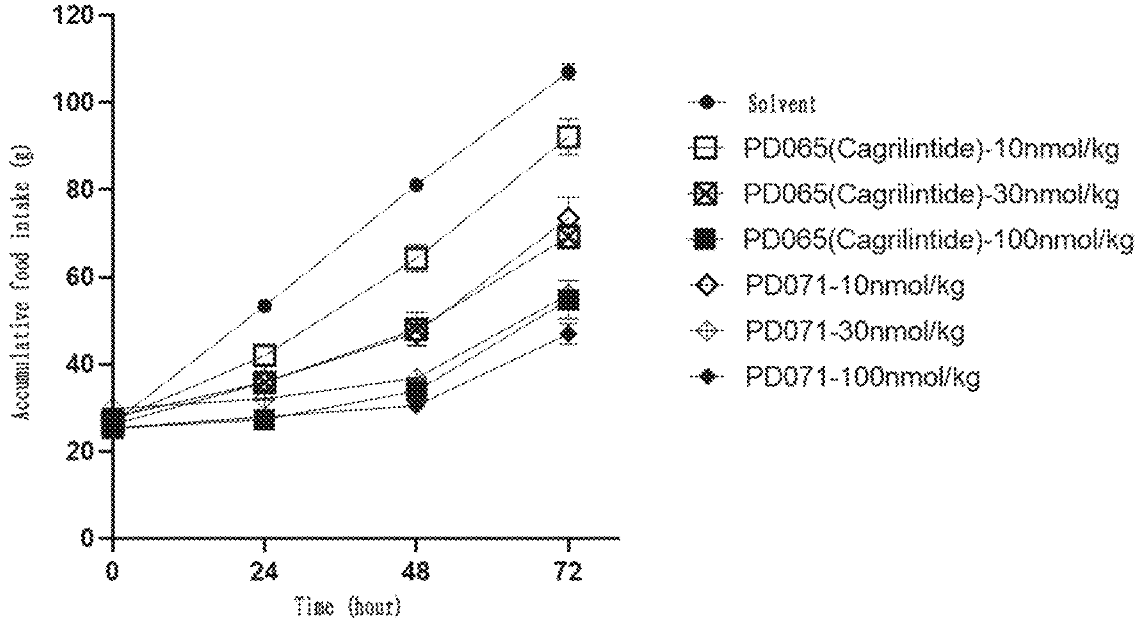
FIG. 4A shows change trends of influences of the compounds PD065 and PD071 at different concentrations on food intake in SD rats with time.
Figure 4B:
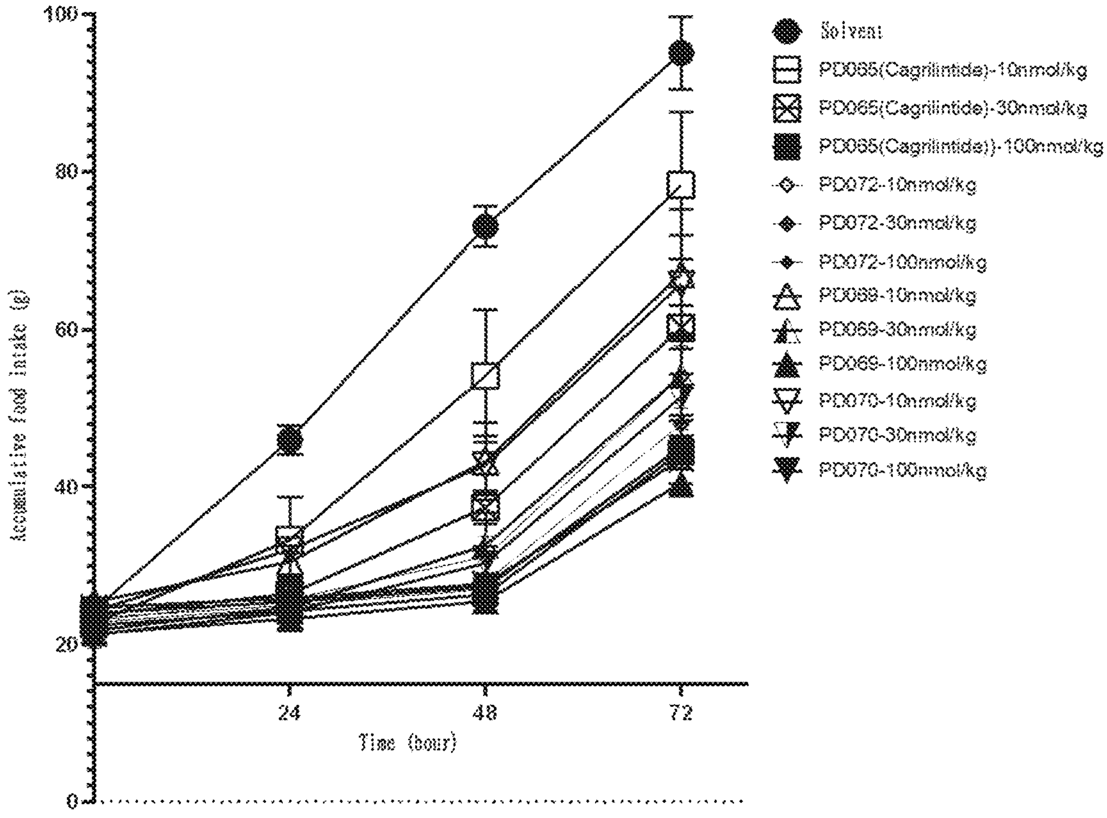
FIG. 4B shows change trends of influences of different derivative treatment groups at different concentrations on food intake in SD rats with time.

Exemplary embodiments of the present disclosure are described hereinafter, and various details of the embodiments of the present application are included to help understanding, which should be considered as being exemplary only. Therefore, those of ordinary skills in the art should realize that various changes and modifications may be made to the embodiments described herein without departing from the scope and spirit of the present disclosure. In the same way, for the purpose of clarity and conciseness, the descriptions of well-known functions and structures are omitted in the following description.

Abbreviation

Corresponding names or structural forms of some abbreviations used in the embodiments of the present disclosure are as shown in Table 3 below:

TABLE 3

| Abbreviation | Structural formula |
|---|---|
| trans-Hyp | 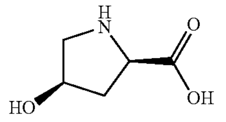 |
| cis-Hyp | 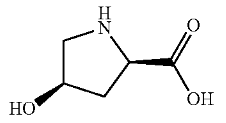 |
| 3-Am-Pro | 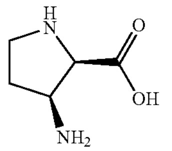 |
| Aad | 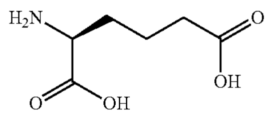 [SMILES: N[C@@H](CCCC(=O)O)C(=O)O] |
| Orn | 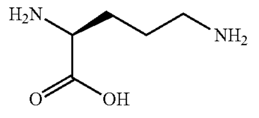 |
| Dab | 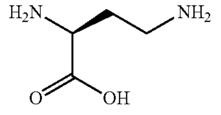 |

TABLE 3-continued

| Abbreviation | Structural formula |
|---|---|
| Dap | 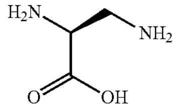 |
| Har | 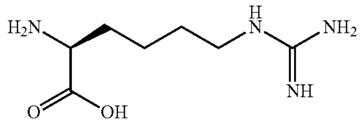 [SMILES: N=C(N)NCCCC[C@H](N)C(=O)O] |
| Pip | 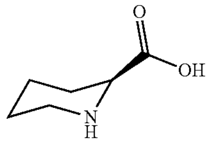 |
| Aze | 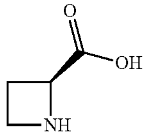 |
| aMePro | 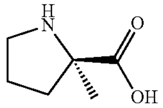 |
| Trx | 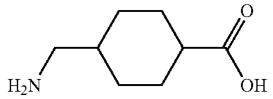 |
| Inp | 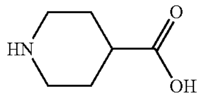 |
| AEEA | 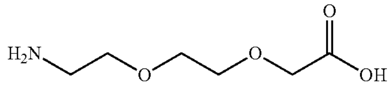 |

AA: Amino Acid;
Boc: t-Butyloxy carbonyl;
DCM: dichloromethane;
DMF: N,N-Dimethyl formamide;
DIEA: N,N-Diisopropylethylamine;
EDT: 1,2-Ethanedithiol;
Fmoc: 9-fluorenylmethyloxycarbonyl;
OtBu: tertiary butyl ester group;
Pbf: 2,2,4,6,7-Pentamethyldihydrobenzofuran-5-sulfonyl chloride;
Pip: Piperidine;
TBTU: O-(Benzotriazol-1-yl)-N,N,N,N,-tetramethyluronium Tetrafluoroborate;
tBu: tertiary butyl;
TFA: Trifluoroacetic acid;
TIS: Triisopropylsilane;
Trt: Triphenylmethyl.

Definition

The “Amylin” or “Amylin polypeptide” or “amylin” or “islet amyloid polypeptide” as used herein refers to a sequence of Lys-Cys-Asn-Thr-Ala-Thr-Cys-Ala-Thr-Gln-Arg-Leu-Ala-Asn-Phe-Leu-Val-His-Ser-Ser-Asn-Asn-Phe-Gly-Ala-Ile-Leu-Ser-Ser-Thr-Asn-Val-Gly-Ser-Asn-Thr-Tyr (SEQ ID NO: 310), or a variant/analog, fragment or fusion protein of the above sequence which has basically maintaining the agon-ism of an amylin receptor.

The “analog” as used herein refers to a compound in which at least one amino acid residue of a specific polypeptide molecule has been substituted by another amino acid residue, and/or at least one amino acid residue has been deleted, and/or at least one amino acid residue has been added to an N-terminal or a C-terminal, and/or at least one amino acid residue has been inserted between any two amino acids.

Unless otherwise clearly indicated in the context, the name of the specific polypeptide in the present disclosure, such as “Amylin”, and the terms “polypeptide”, “analog” and “variant” are interchangeable.

The “derivative” as used herein refers to a product obtained by modifying a functional group (such as an amino acid residue) of a biological macromolecule (such as a polypeptide and a protein) with certain compound or molecule. The modification comprises, but is not limited to, acylation, amidation, esterification and thioesterification.

The pharmaceutical composition according to the present disclosure may be administered in any suitable way, such as oral administration, nasal administration, intradermal administration, subcutaneous administration, intramuscular administration or intravenous administration.

The disease related to “fat metabolism disorder” in the present disclosure is a general name of related diseases caused by fat metabolism disorder, and the common disease is weight abnormality, such as obesity, and further comprises, for example, hyperlipidemia, hypertension, atherosclerosis, fatty liver, liver cirrhosis, a coronary heart disease, angina pectoris, myocardial infarction, an inflammatory bowel disease, dyspepsia, gastrointestinal ulcer, and the like.

The “weight abnormality” in the present disclosure means that, in the same evaluation system, a weight evaluation index of an object is beyond a normal average range of its population. In some embodiments, the weight abnormality refers to obesity. In some embodiments, the “weight loss” refers to reducing overweight or obesity.

EXAMPLES

The present disclosure may be better understood with reference to the following examples. However, it should be understood that the following examples are only for illustrative purposes and should not be construed as limiting the scope of protection of the present disclosure in any way. Unless otherwise specified, the present disclosure may be implemented according to the methods listed in the experimental manuals such as “Molecular Cloning: A Laboratory Manual” and “Cell: A Laboratory Manual” as well as in the experimental guidelines of CFDA, which are familiar to those skilled in the art. The reagent raw materials used are all commercially available, and may be purchased through open channels.

Example 1 Preparation of Amylin Derivative

A polypeptide was synthesized by a solid-phase organic synthesis method according to a Fmoc-protected amino acid strategy and an SPPS solid-phase synthesis technology, and was lysed, oxidized and purified to obtain a target product.

Taking a compound PD065 (Cagrilintide) as an example, a structural formula of the compound is as follows (SEQ ID NO: 178):

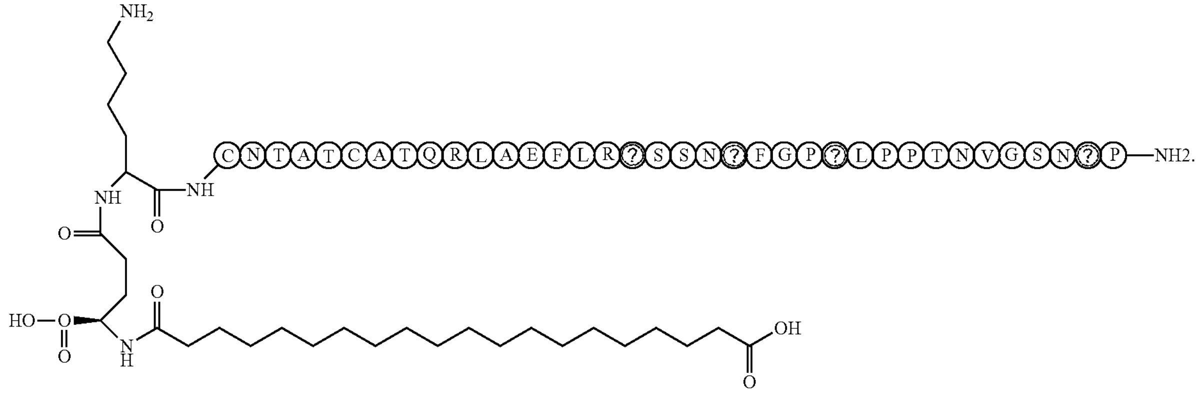

The synthesis process was as follows.

Solid-phase synthesis: amino acid connection was condensed from a C-terminal to an N-terminal (from right to left) by a method as shown in Table 4 with Fmoc-Linker MBHA Resin S=0.32 mmol/g through an Fmoc/tBu process according to the above sequence.

TABLE 4

| List of synthesis procedures | | | |
|---|---|---|---|
| Procedure number | Solvent | Number of times | Time (min/time) |
| 1 | 20% Pip/DMF | 1 | 10 |
| 2 | 20% Pip/DMF | 1 | 5 |
| 3 | DMF | 5 | 1 |
| 4 | Sample and color development detection | | |
| 5 | AA/DIEA/TBTU | 1 | 60 |
| 6 | DMF | 4 | 1 |
| 7 | Sample and color development detection | | |
| Procedure description | 1. The procedures 1 to 7 were repeated until the synthesis of linear peptide was finished. | | |

An amino acid coupling order was as follows: A-01Fmoc-Pro-OH, A-02Fmoc-Thr(tBu)-OH, A-03Fmoc-Asn(Trt)-OH, A-04Fmoc-Ser(tBu)-OH, A-05Fmoc-Gly-OH, A-06Fmoc-Val-OH, A-07Fmoc-Asn (Trt)-OH, A-08Fmoc-Thr(tBu)-OH, A-09Fmoc-Pro-OH, A-10Fmoc-Pro-OH, A-11Fmoc-Leu-OH, A-12Fmoc-Ile-OH, A-13Fmoc-Pro-OH, A-14Fmoc-Gly-OH, A-15Fmoc-Phe-OH, A-16Fmoc-Asn(Trt)-OH, A-17Fmoc-Asn(Trt)-OH, A-18Fmoc-Ser(tBu)-OH, A-19Fmoc-Ser(tBu)-OH, A-20Fmoc-His(Trt)-OH, A-21Fmoc-Arg(Pbf)-OH, A-22Fmoc-Leu-OH, A-23Fmoc-Phe-OH, A-24Fmoc-Glu (OtBu)-OH, A-25Fmoc-Ala-OH, A-26Fmoc-Leu-OH, A-27Fmoc-Arg(Pbf)-OH, A-28Fmoc-Gln(Trt)-OH, A-29Fmoc-Thr(tBu)-OH, A-30Fmoc-Ala-OH, A-31Fmoc-Cys(Trt)-OH, A-32Fmoc-Thr(tBu)-OH, A-33Fmoc-Ala-OH, A-34Fmoc-Thr(tBu)-OH, A-35Fmoc-Asn(Trt)-OH, A-36Fmoc-Cys(Trt)-OH, A-37Fmoc-Lys(Boc)-OH, A-38Fmoc-Glu-otbu, A-39C20 diacid.

Finally, the polypeptide derivative resin was formed, and the polypeptide derivative resin (peptide resin) was washed, transferred out, and dried to a constant weight to be lysed. Lysis of Peptide Resin:

Preparation of lysis reagents: amount of the lysis reagents was calculated according to 1 g peptide resin: 10 ml±2 ml, TFA:$H_2O$:EDT:TIS=95:1:2:2. Required lysis reagents $H_2O$, TFA, EDT and TIS were sequentially added into a lysis reaction bottle, and a temperature of the lysis reagents was controlled at 0° C. to 10° C.; the lysis reagents were added into the peptide resin under stirring. After the temperature of the system was stabilized, the temperature of the lysis reagents was controlled at 25° C. to 30° C., and the lysis reagents reacted under stirring for 2.5 hours. The lysis reagents were filtered out and precipitated with 5 times of liquid volume of glacial ethyl ether, and the precipitate was filtered out, washed with 3 times of liquid volume of glacial ethyl ether for 3 times, and dried at room temperature under a reduced pressure to obtain a solid crude product.

Oxidation of polypeptide: the crude product was finely ground, purified water was prepared, the finely ground crude product was slowly added under stirring, and an acetonitrile aqueous solution was dropwise added at the same time. After the crude product was completely added and dissolved, an iodine methanol solution was added and stirred for half an hour.

Purification and freeze-drying: the above oxidized liquid was filtered with a 0.45 μm microporous filtering membrane. The crude product was purified by a C-18 packing preparative column, and separated and purified at room temperature according to an appropriate gradient, and a target product was collected, analyzed and detected, and classified. The purity was required to be greater than or equal to 90%, an unqualified target product was collected, and separated and purified again according to an appropriate gradient, and then a qualified liquid peak was collected. The above qualified liquid sample was freeze-dried under reduced pressure to obtain refined polypeptide freeze-dried powder.

Compounds as shown in Table 2 were prepared by methods and steps similar to those of the compound PD065 (Cagrilintide).

Example 2 In-Vitro Efficacy Detection of Amylin Derivatives

The experiment was intended to detect the activity or efficacy of the amylin derivatives on a human amylin receptor in vitro by luciferase assay.

2.1 Construction of Amylin Receptor/CRE-Luc Cell Line

CHO-K1/Ga15/AMY3 cells (a calcitonin receptor and a receptor-activated modified peptide RAMP had been constructed and purchased from GenScript) were transfected with a plasmid containing a luciferase expression cassette driven by multiple copies of cAMP response elements (CRE) by a standard method, and cultured in an F12 medium containing 200 μg/ml zeocin, 2 μg/mL puromycin, 100

μg/mL hygromycin and 400 μg/ml G418 to obtain the amylin receptor/CRE-luc cell line with stable transfection.

2.2 Luciferase Assay of Amylin

50 μL of growth medium (F12 medium containing 10% FBS) was added into each well of a white 96-well plate, and the stably transfected amylin/CRE-luc CHO cells were inoculated into the white 96-well plate at a density of about 20,000 cells/well for activity determination.

The freeze-dried powder obtained in Example 1 was dissolved in 20 mM phosphate buffer solution at pH 7.0, and diluted with the F12 medium containing 10% FBS to obtain a derivative sample at an initial concentration of 100 nM, the derivative sample was diluted with the F12 medium containing 10% FBS in gradient to obtain samples at 7 concentrations which were different by 10 times from 100 nM to $10^{-5}$ nM, 50 μL of sample determination solution at a corresponding concentration was added into each well, incubated at 37° C. and 5% under $CO_2$ for 24 hours, then added with 100 μL of Luciferase per well, incubated for 3 minutes, and finally, a luminescence was determined on SpectraMax L (Molecular Devices) with SoftMax Pro 7.0.3 GxP software, and a standard curve was drawn according to a fluorescence value to calculate EC50. Results were shown in Table 5.

TABLE 5

| Serial number of compound | EC50/nM |
|---|---|
| PD001 | 0.042 |
| PD002 | 0.119 |
| PD003 | 0.14 |
| PD004 | 0.102 |
| PD006 | 0.129 |
| PD007 | 0.205 |
| PD008 | 0.281 |
| PD009 | 0.067 |
| PD017 | 0.772 |
| PD040 | 0.118 |
| PD041 | 0.259 |
| PD042 | 0.111 |
| PD043 | 1.13 |
| PD044 | 2.617 |
| PD045 | 0.364 |
| PD046 | 1.676 |
| PD047 | 0.073 |
| PD048 | 0.047 |
| PD049 | 0.215 |
| PD050 | 0.098 |
| PD051 | 0.039 |
| PD052 | 0.03 |
| PD053 | 0.075 |
| PD054 | 0.049 |
| PD055 | 0.909 |
| PD056 | 0.586 |
| PD057 | 0.793 |
| PD058 | 0.319 |
| PD059 | 0.939 |
| PD060 | 0.246 |
| PD061 | 0.815 |
| PD062 | 0.374 |
| PD063 | 0.101 |
| PD064 | 0.055 |
| PD065 | 0.038 |
| PD066 | 0.044 |
| PD067 | 0.034 |
| PD068 | 0.032 |
| PD069 | 0.039 |
| PD070 | 0.038 |
| PD071 | 0.028 |
| PD072 | 0.027 |
| PD073 | 0.063 |
| PD074 | 0.066 |
| PD075 | 0.048 |

TABLE 5-continued

| Serial number of compound | EC50/nM |
|---|---|
| PD076 | 0.04 |
| PD077 | 0.034 |
| PD078 | 0.035 |
| PD079 | 0.131 |
| PD080 | 0.11 |
| PD081 | 0.031 |
| PD082 | 0.038 |
| PD083 | 0.037 |
| PD084 | 0.008 |
| PD085 | 0.005 |
| PD086 | 0.033 |
| PD087 | 0.032 |
| PD088 | 0.013 |
| PD089 | 0.018 |
| PD090 | 0.031 |
| PD091 | 0.03 |
| PD092 | 0.016 |
| PD093 | 0.019 |
| PD094 | 0.034 |
| PD095 | 0.047 |
| PD096 | 0.042 |
| PD097 | 0.014 |
| PD098 | 0.077 |
| PD099 | 0.033 |
| PD100 | 0.06 |
| PD101 | 0.012 |
| PD102 | 0.033 |
| PD103 | 0.033 |
| PD104 | 0.011 |
| PD105 | 0.033 |
| PD106 | 0.026 |
| PD107 | 0.027 |
| PD108 | 0.028 |
| PD109 | 0.01 |
| PD110 | 0.039 |
| PD111 | 0.008 |
| PD112 | 0.03 |
| PD113 | 0.017 |
| PD114 | 0.029 |
| PD115 | 0.011 |
| PD116 | 0.033 |
| PD117 | 0.014 |
| PD118 | 0.032 |
| PD119 | 0.024 |
| PD120 | 0.023 |
| PD121 | 0.018 |
| PD122 | 0.048 |
| PD123 | 0.068 |
| PD124 | 0.008 |
| PD125 | 0.01 |
| PD126 | 0.028 |
| PD156 | 0.029 |
| PD158 | 0.022 |
| PD159 | 0.037 |
| PD160 | 0.035 |
| PD161 | 0.026 |
| PD162 | 0.035 |
| PD163 | 0.084 |
| PD164 | 0.111 |
| PD165 | 0.05 |
| PD166 | 0.054 |
| PD167 | 0.05 |
| PD168 | 0.041 |
| PD169 | 0.039 |
| PD170 | 0.041 |
| PD171 | 0.053 |
| PD172 | 0.075 |
| PD173 | 0.064 |
| PD174 | 0.046 |
| PD176 | 0.029 |
| PD177 | 0.024 |
| PD178 | 0.017 |
| PD179 | 0.017 |
| PD180 | 0.016 |
| PD181 | 0.022 |
| PD182 | 0.034 |

TABLE 5-continued

| Serial number of compound | EC50/nM |
|---|---|
| PD183 | 0.04 |
| PD184 | 0.037 |
| PD186 | 0.052 |
| PD187 | 0.016 |
| PD188 | 0.025 |
| PD189 | 0.029 |
| PD190 | 0.017 |
| PD191 | 0.061 |
| PD192 | 0.087 |
| PD193 | 0.074 |
| PD194 | 0.074 |
| PD195 | 0.025 |
| PD196 | 0.064 |
| PD197 | 0.025 |
| PD198 | 0.029 |
| / | / |
| / | / |
| / | / |
| / | / |
| / | / |
| / | / |
| / | / |
| / | / |
| / | / |
| / | / |
| / | / |
| / | / |
| / | / |
| / | / |
| / | / |
| / | / |
| / | / |
| / | / |
| / | / |
| / | / |
| / | / |
| / | / |
| / | / |
| / | / |

Results in Table 5 showed that the polypeptide derivatives of the present disclosure all had good activity to the human amylin receptor.

Example 3 Freeze-Thaw Stability of Derivatives

The freeze-dried powder of the polypeptide analog derivative prepared in Example 1 was mixed with a buffer solution according to a mass-volume ratio of 0.2 mg/ml, the polypeptide was dissolved with 20 mM phosphate buffer solution (PB) (pH 7.0), the sample was stored at −20° C. for overnight storage, and then the sample was taken out to be restored to room temperature for thawing. During the experiment, property changes of the polypeptide after dissolution and freezing and thawing were observed and recorded respectively, and concentrations of the polypeptide before and after the freezing and thawing were detected by the following liquid chromatography method:

Materials and equipment: high-performance liquid chromatographic instrument (Agilent 1200), ultrapure water (18.2 M (2 self-manufactured ultrapure water), acetonitrile (HPLC grade), and trifluoroacetic acid (HPLC grade); and reversed-phase chromatographic column: Sepax Bio-C4 4.6*100 mm 5 μm 300 Å.

Sample preparation: a certain amount of polypeptide was dissolved with 20 mM PB buffer solution at pH 7.4, and in the case of poor solubility, a small amount of 0.1 M NaOH could be added to adjust the pH to 8.0 for complete dissolution, and a concentration of the solution was controlled between 0.5 mg/ml and 2 mg/ml. A sample to be tested was centrifuged at 10,000 rpm and 4° C. for 3 minutes, and a supernatant was taken and added into a liquid-phase sample injection bottle.

Chromatographic conditions: flow rate: 1.0 ml/min; automatic sample injection temperature: 15° C.; column temperature: 15° C.; detection wavelength: 280 nm; mobile phase A: 100% $H_2O$+0.05% TFA; and mobile phase b: 100% CAN. Elution gradients were as shown in the following table:

TABLE 6

List of elution gradients of liquid chromatography

| | Time (min) | | | | |
|---|---|---|---|---|---|
| | 0 | 10 | 14 | 15 | 25 |
| B % | 5 | 35 | 70 | 5 | 5 |

A freeze-thaw yield was calculated by the following formula: freeze-thaw yield=concentration of polypeptide after the freezing and thawing/concentration of polypeptide before the freezing and thawing. Related results were as shown in Table 7.

TABLE 7

| Name of compound | Dissolution property | Freeze storage property | Freeze storage yield |
|---|---|---|---|
| PD001 | Clear | Clear | / |
| PD002 | Clear | Clear | / |
| PD003 | Clear | Clear | / |
| PD004 | Clear | Clear | / |
| PD005 | Clear | Clear | / |
| PD006 | Clear | Clear | / |
| PD007 | Clear | Clear | / |
| PD008 | Clear | Clear | / |
| PD009 | Clear | Clear | / |
| PD010 | Clear | Clear | / |
| PD011 | Clear | Slightly muddy | 15.33% |
| PD012 | Muddy | Muddy | 0.00% |
| PD013 | Clear | Muddy | 18.78% |
| PD014 | Clear | Clear | 95.77% |
| PD015 | Clear | Slightly muddy | 0.00% |
| PD016 | Clear | Clear | 75.53% |
| PD017 | Clear | Muddy | 100.81% |
| PD018 | Muddy | Muddy | 33.24% |
| PD019 | Muddy | Muddy | No peak |
| PD020 | Slightly muddy | Muddy | 0.00% |
| PD021 | Muddy | Muddy | 21.35% |
| PD022 | Muddy | Muddy | 72.10% |
| PD023 | Muddy | Muddy | 64.54% |
| PD024 | Muddy | Muddy | 79.10% |
| PD025 | Clear | Muddy | 102.64% |
| PD026 | / | / | / |
| PD027 | Muddy | Muddy | 58.88% |
| PD028 | Muddy | Muddy | 0.00% |
| PD029 | Muddy | Muddy | 27.17% |
| PD030 | Clear | Clear | 94.86% |
| PD031 | Muddy | Muddy | 81.43% |
| PD032 | Clear | Clear | 103.57% |
| PD033 | Clear | Clear | 69.52% |
| PD034 | Clear | Muddy | 89.35% |
| PD035 | Muddy | Muddy | 0.00% |
| PD036 | Muddy | Muddy | 0.00% |
| PD037 | Muddy | Muddy | 98.81% |
| PD038 | Muddy | Muddy | 100.87% |
| PD039 | Clear | Clear | 96.97% |
| PD040 | Clear | Clear | 95.62% |
| PD041 | Clear | Clear | 96.58% |

TABLE 7-continued

| Name of compound | Dissolution property | Freeze storage property | Freeze storage yield |
|---|---|---|---|
| PD042 | Clear | Clear | 95.19% |
| PD043 | Clear | Clear | 49.45% |
| PD044 | Clear | Clear | 84.90% |
| PD045 | Clear | Clear | 95.59% |
| PD046 | Clear | Clear | 101.35% |
| PD047 | Clear | Clear | 0.00% |
| PD048 | Clear | Clear | 102.16% |
| PD049 | Clear | Clear | 99.00% |
| PD050 | Clear | Clear | 99.66% |
| PD051 | Clear | Clear | 99.71% |
| PD052 | Clear | Clear | 96.53% |
| PD053 | Clear | Clear | 104.17% |
| PD054 | Clear | Clear | 103.78% |
| PD055 | Clear | Clear | 99.75% |
| PD056 | Clear | Clear | 101.22% |
| PD057 | Clear | Clear | 99.70% |
| PD058 | Clear | Clear | 98.34% |
| PD059 | Clear | Clear | 103.57% |
| PD060 | Clear | Clear | 104.35% |
| PD061 | Clear | Clear | 100.32% |
| PD062 | Clear | Clear | 102.63% |
| PD063 | Clear | Clear | 107.52% |
| PD064 | Clear | Clear | 103.04% |
| PD065 | Clear | Clear | 93.44% |
| PD066 | Clear | Clear | 93.44% |
| PD067 | Clear | Clear | 98.84% |
| PD068 | Clear | Clear | 97.55% |
| PD069 | Clear | Clear | 100.00% |
| PD070 | Clear | Clear | 100.00% |
| PD071 | Clear | Clear | 100.80% |
| PD072 | Clear | Clear | 103.19% |
| PD073 | Clear | Clear | 155.32% |
| PD074 | Clear | Clear | 66.34% |
| PD075 | Clear | Clear | 56.70% |
| PD076 | Clear | Clear | 52.18% |
| PD077 | Clear | Clear | 85.60% |
| PD078 | Clear | Clear | 67.85% |
| PD079 | Clear | Clear | 96.15% |
| PD080 | Clear | Clear | 90.06% |
| PD081 | Clear | Clear | 76.82% |
| PD082 | / | / | / |
| PD083 | Clear | Clear | 79.98% |
| PD084 | / | / | / |
| PD085 | Clear | Clear | 76.70% |
| PD086 | Clear | Clear | 69.09% |
| PD087 | Clear | Clear | 102.65% |
| PD088 | Clear | Clear | 120.04% |
| PD089 | Clear | Clear | 101.91% |
| PD090 | Clear | Clear | 99.24% |
| PD091 | Clear | Clear | 101.14% |
| PD092 | Clear | Clear | 101.74% |
| PD093 | Clear | Clear | 99.86% |
| PD094 | Clear | Clear | 102.94% |
| PD095 | Clear | Clear | 95.26% |
| PD096 | Clear | Clear | 101.99% |
| PD097 | Clear | Clear | 98.20% |
| PD098 | / | / | / |
| PD099 | Clear | Clear | 102.80% |
| PD100 | Clear | Clear | 102.97% |
| PD101 | Clear | Clear | 97.67% |
| PD102 | Clear | Clear | 97.43% |
| PD103 | Clear | Clear | 98.68% |
| PD104 | Clear | Clear | 99.05% |
| PD105 | Clear | Clear | 111.06% |
| PD106 | Clear | Clear | 99.24% |
| PD107 | Clear | Clear | 111.06% |
| PD108 | Clear | Clear | 96.86% |
| PD109 | Clear | Clear | 100.53% |
| PD110 | Clear | Clear | 109.34% |
| PD111 | Clear | Clear | 105.17% |
| PD112 | Clear | Clear | 98.62% |
| PD113 | Clear | Clear | 77.90% |
| PD114 | Clear | Clear | 101.02% |
| PD115 | Clear | Clear | 104.27% |
| PD116 | Clear | Clear | 102.48% |
| PD117 | Clear | Clear | 93.49% |

TABLE 7-continued

| Name of compound | Dissolution property | Freeze storage property | Freeze storage yield |
|---|---|---|---|
| PD118 | Clear | Clear | 104.70% |
| PD119 | Clear | Clear | 103.04% |
| PD120 | Clear | Clear | 103.41% |
| PD121 | Clear | Clear | 102.87% |
| PD122 | Clear | Clear | 103.66% |
| PD123 | Clear | Clear | 102.11% |
| PD124 | Clear | Clear | 91.04% |
| PD125 | Clear | Clear | 95.59% |
| PD126 | Clear | Clear | 99.24% |
| PD127 | Clear | Clear | 101.18% |
| PD128 | Clear | Clear | 97.05% |
| PD129 | Clear | Clear | 106.67% |
| PD130 | Clear | Clear | 107.64% |
| PD131 | Clear | Clear | 108.14% |
| PD132 | Clear | Clear | 101.01% |
| PD133 | Clear | Clear | 98.24% |
| PD134 | Clear | Clear | 101.39% |
| PD135 | Clear | Clear | 110.57% |
| PD136 | Clear | Clear | 108.07% |
| PD137 | Clear | Clear | 102.20% |
| PD138 | Clear | Clear | 106.03% |
| PD139 | Clear | Clear | 104.78% |
| PD140 | Clear | Clear | 100.18% |
| PD141 | Clear | Clear | 96.57% |
| PD142 | Clear | Clear | 101.09% |
| PD143 | Clear | Clear | 118.11% |
| PD144 | Clear | Clear | 101.98% |
| PD145 | Clear | Clear | 100.88% |
| PD146 | Clear | Clear | 101.09% |
| PD147 | Clear | Clear | 106.44% |
| PD148 | Clear | Clear | 103.34% |
| PD149 | Clear | Clear | 99.99% |
| PD150 | Clear | Clear | 103.74% |
| PD151 | Clear | Clear | 101.88% |
| PD152 | Clear | Clear | 97.96% |
| PD153 | / | / | / |
| PD154 | / | / | / |

As shown in Table 7, most of the polypeptide derivatives in the present disclosure had good freeze-thaw stability and yield.

Example 4 Study on 40° C. Stability of Derivatives

Compound PD065, PD069, PD070, PD071 or PD072 was mixed with sodium dihydrogen phosphate (1.42 mg/ml) according to 1.34 mg/ml, and dissolved in ultrapure water, pH of the solution was adjusted to about 7.4 with hydrochloric acid/sodium hydroxide, and then the solution was filtered into a sterilized penicillin bottle with a 0.22 μm sterile filter in an ultra-clean workbench. The penicillin bottle after covering was placed in a stability test box at 40° C.

Before testing, a sample was centrifuged at 10,000 rpm and 4° C. for 3 minutes, and a supernatant was taken and added into a liquid-phase sample injection bottle. The sample was detected by the liquid phase method in Example 3. Results were as shown in Table 8 and FIG. 1.

TABLE 8

| Name of sample and number of days | Retention time (min) | Protein concentration (mg/ml) | Decrease percentage of protein concentration |
|---|---|---|---|
| PD065 (0d) | 12.95 | 0.81 | 0.00% |
| PD065 (7d) | 12.96 | 0.63 | 22.35% |
| PD065 (15d) | 12.972 | 0.43 | 46.78% |
| PD069 (0d) | 12.842 | 1.01 | 0.00% |
| PD069 (7d) | 12.853 | 0.69 | 31.57% |

TABLE 8-continued

| Name of sample and number of days | Retention time (min) | Protein concentration (mg/ml) | Decrease percentage of protein concentration |
|---|---|---|---|
| PD069 (15d) | 12.86 | 0.52 | 47.84% |
| PD070 (0d) | 13.007 | 0.98 | 0.00% |
| PD070 (7d) | 13.01 | 0.95 | 2.53% |
| PD070 (15d) | 13.01 | 0.92 | 6.28% |
| PD071 (0d) | 12.718 | 0.71 | 0.00% |
| PD071 (7d) | 12.745 | 0.38 | 46.69% |
| PD071 (15d) | 12.768 | 0.30 | 58.16% |
| PD072 (0d) | 12.867 | 0.96 | 0.00% |
| PD072 (7d) | 12.893 | 0.59 | 38.60% |
| PD072 (15d) | 12.883 | 0.49 | 49.27% |

As shown in Table 8, the thermal stability of the polypeptide derivatives in the present disclosure was basically equivalent to the thermal stability of the PD065, and surprisingly, the compound PD070 showed an extremely low decrease percentage of protein concentration. Example 5 Study on weight loss efficacy of derivatives SD (Sprague Dawley) rats weighing 200 g to 250 g were selected for this experimental study. Before the experiment, the rats arrived for at least 10 days to 14 days to adapt to the experimental environment. During this period, the rats were fed for two weeks in a reversed light/dark stage (meaning that the light was turned off during the day and turned on during the night) after arrival, and were fed separately in the first week of arrival to ensure accurate data and high test sensitivity, and the rats were free to obtain food and water during the whole adaptation period and experimental period. There were an experimental group A: A1, A2, A3, A4, A5 and A6, and an experimental group B: B1, B2, B3, B4 and B5, with 5 to 8 rats in each treatment group of the derivative, and the rats in each group were subcutaneously administered with a derivative or a solvent by a dosage of 30 nmol/kg. The administration time of each group was recorded. After administration, the rats were put back into their cages in which the rats could get food and water. Food consumption and weight changes of the rats were recorded every 24 hours by online recording or manual recording.

Weight and food intake changes of the SD rats in each group were as shown in FIG. 2A to FIG. 2D, Table 9 and Table 10.

TABLE 9

| Group | Treatment group | Weight change rate at $48^{th}$ hour |
|---|---|---|
| A1 | Solvent | 6.50 |
| A2 | PD065 (Cagrilintide) | −6.13 |
| A3 | PD069 | −8.70 |
| A4 | PD070 | −7.86 |
| A5 | PD071 | −10.58 |
| A6 | PD072 | −12.75 |

TABLE 10

| Group | Treatment group | Weight change rate at $48^{th}$ hour |
|---|---|---|
| B1 | Solvent | 5.61 |
| B2 | PD065 (Cagrilintide) | −6.74 |
| B3 | PD158 | −8.37 |
| B4 | PD160 | −7.87 |
| B5 | PD161 | −7.81 |

Experimental results showed that, compared with a weight reduction effect of the PD065, the polypeptide derivatives in the present disclosure showed better weight reduction ability, which could even reach more than twice the weight reduction effect of the PD065.

Example 6 Study on Weight Loss Effect of Dosage of Derivatives

SD rats obtained by the same method as in Example 5 were used in this experimental study. There were an experimental group C: C1 to C13, and an experimental group D: D1 to D7, with 5 to 8 rats in each group of the derivative test, and according to administration schemes as shown in Table 11 and Table 12, the rats in each group were subcutaneously administered with a derivative or a solvent by a dosage of 10 nmol/kg, 20 nmol/kg or 30 nmol/kg. The administration time of each group was recorded. After administration, the rats were put back into their cages in which the rats could get food and water. Food consumption and weight changes of the rats were recorded every 24 hours by online recording or manual recording.

Weight and cumulative food intake changes of the SD rats in each group were as shown in FIG. 3A to FIG. 3D, FIG. 4A to FIG. 4B, Table 11 and Table 12.

TABLE 11

| Group | Active ingredient and dosage | Weight change rate at $72^{nd}$ hour (%) | Cumulative food intake at $72^{nd}$ hour (g) |
|---|---|---|---|
| C1 | Solvent | 6.03 | 95.11 |
| C2 | PD065 (Cagrilintide), 10 nmol/kg | 1.59 | 78.31 |
| C3 | PD065 (Cagrilintide), 30 nmol/kg | 0.46 | 60.22 |
| C4 | PD065 (Cagrilintide), 100 nmol/kg | −6.61 | 44.41 |
| C5 | PD069, 10 nmol/kg | 1.36 | 67.05 |
| C6 | PD069, 30 nmol/kg | −4.16 | 54.14 |
| C7 | PD069, 100 nmol/kg | −7.88 | 40.5 |
| C8 | PD070, 10 nmol/kg | 0.47 | 65.71 |
| C9 | PD070, 30 nmol/kg | −4.96 | 51.4 |
| C10 | PD070, 100 nmol/kg | −8.47 | 45.04 |
| C11 | PD072, 10 nmol/kg | −2.43 | 53.99 |
| C12 | PD072, 30 nmol/kg | −6.61 | 47.96 |
| C13 | PD072, 100 nmol/kg | −8.30 | 44.84 |

TABLE 12

| Group | Active ingredient and dosage | Weight change rate at $72^{nd}$ hour (%) | Cumulative food intake at $72^{nd}$ hour (g) |
|---|---|---|---|
| D1 | Solvent | 10.36 | 81.17 |
| D2 | PD065 (Cagrilintide), 10 nmol/kg | 5.95 | 64.27 |
| D3 | PD065 (Cagrilintide), 30 nmol/kg | 2.81 | 48.00 |
| D4 | PD065 (Cagrilintide), 100 nmol/kg | −3.81 | 33.89 |
| D5 | PD071, 10 nmol/kg | 1.34 | 47.17 |
| D6 | PD071, 30 nmol/kg | −4.77 | 36.81 |
| D7 | PD071, 100 nmol/kg | −7.54 | 30.54 |

It could be seen from experimental results that, compared with the PD065 (Cagrilintide), the polypeptide derivative molecule in the present disclosure had better weight reduction effect under the same conditions.

Example 7. Study on Fatty Acid Side Chain of Derivatives

Figure 5A:
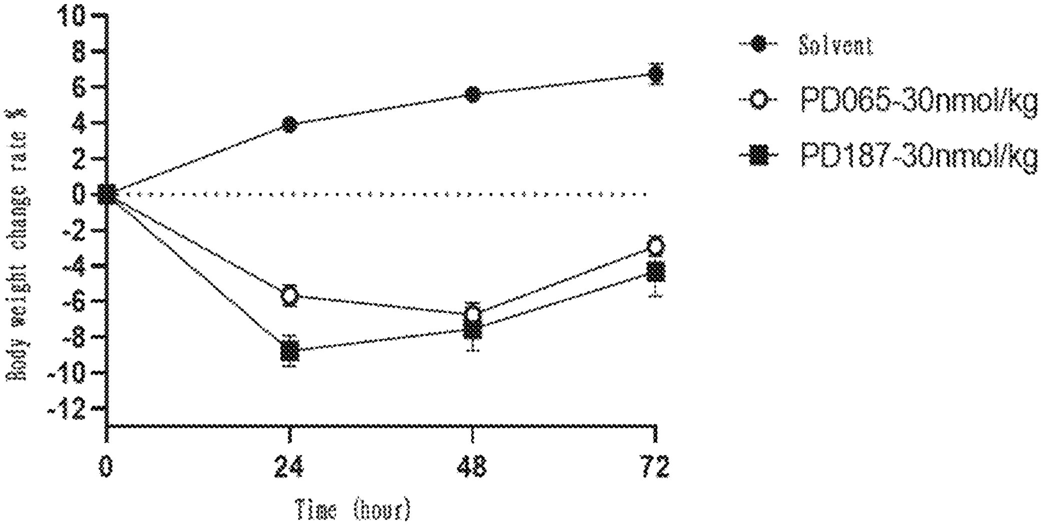
FIG. 5A shows change trends of weight loss effects of the compounds PD065 and PD187 in SD rats with time.
Figure 5B:
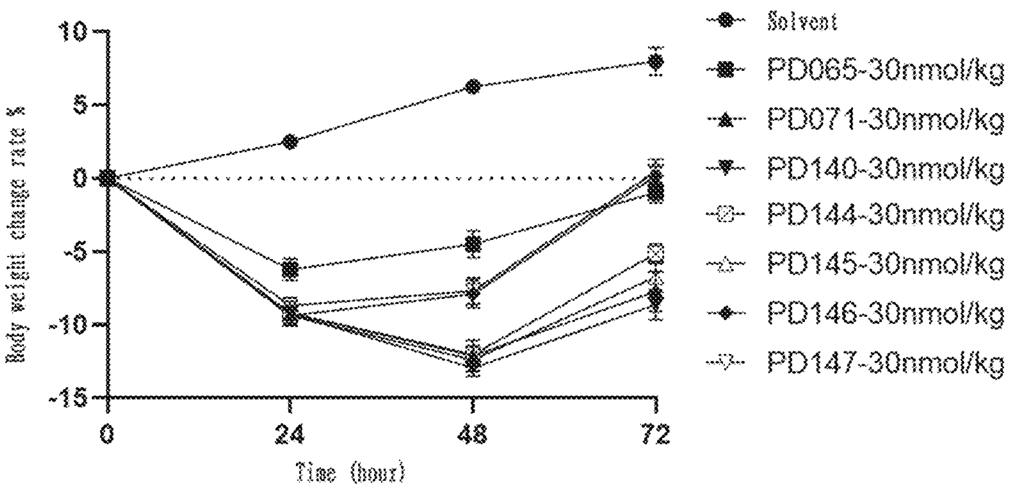
FIG. 5B shows change trends of weight loss effects of corresponding compounds in SD rats with time.
Figure 5C:
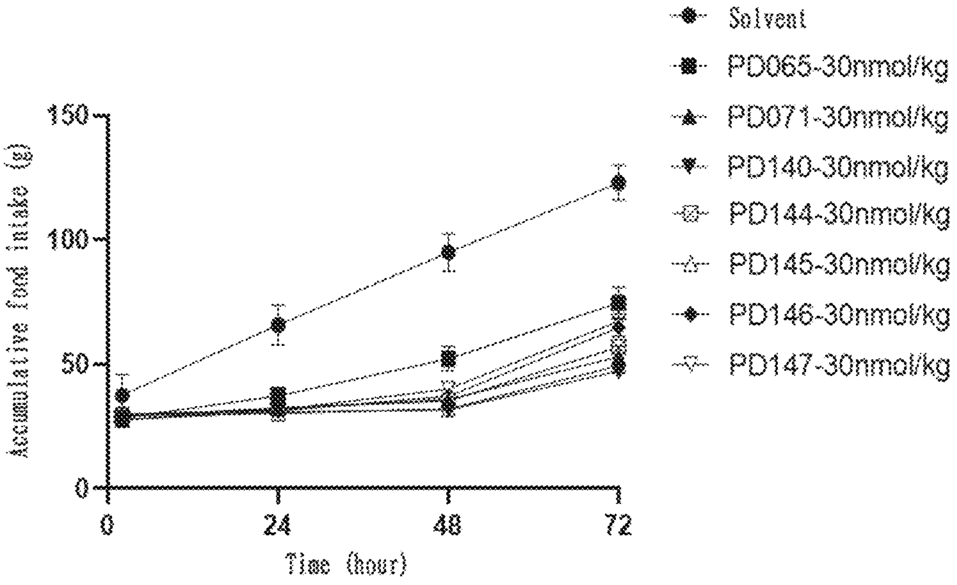
FIG. 5C shows change trends of influences of corresponding compounds on food intake in SD rats with time.

SD rats obtained by the same method as in Example 5 were used in this experimental study. There were an experimental group E: for testing weight reduction effects of the compounds PD065 and PD187, and an experimental group F: for testing the compounds PD065, PD071, PD140, PD144, PD145, PD146 and PD147, with 5 to 8 rats in each group of the derivative test, and the rats in each group were subcutaneously administered with a derivative or a solvent by a dosage of 30 nmol/kg. The administration time of each group was recorded. After administration, the rats were put back into their cages in which food and water available for the rats were placed. Food consumption and weight changes of the rats were recorded every 24 hours by online recording or manual recording. Results of the experimental group E were as shown in FIG. 5A, and results of the experimental group F were as shown in FIG. 5B and FIG. 5C.

Results of the animal experiment showed that, when an N-terminal was R (PD140), the activity was better than that of the PD065.

In order to further evaluate the effect of the fatty acid side chain on polypeptide activity, the PD071 (SEQ ID NO. 3) was used as a peptide backbone, and results showed that, when linkers of different fatty acids, such as 2AEEA+C20 diacid (PD187), αAsp+C20 diacid (PD144), BAsp+C20 diacid (PD145), Trx+C20 diacid (PD146) and Inp+C20 diacid (PD147) were used, the activity of the polypeptides was better than that of the PD065.

Example 8. Preparation of Polypeptide Derivative Tablet Containing Fatty Acid Side Chain A polypeptide derivative containing a fatty acid side chain was prepared into an oral tablet, and the tablet contained the same content of oral delivery agent PNAC. A preparation method of the PNAC was as follows.

N-[8-(2-hydroxybenzoyl)amino]octanoic acid (NAC) was prepared according to the method in Example 1 of the international patent application WO2008/028859. Isopropanol (22070.0 ml, 4.0 vol) was added into a 50 L reaction kettle, started to stir, and added with the NAC (5518 g, 1.0 eq). The system was heated to 50° C., and the prepared 50% potassium hydroxide solution (1304.0 g, 1.0 eq) was dropwise added into the system. After dropwise adding, the system turned into a clear and transparent yellow solution, and reacted under thermal insulation at 50° C. for 1 hour. The reaction solution was concentrated in batches at 40° C., and a crude product was light orange yellow in color.

The crude product was added with isopropanol (19310.0 ml, 3.5 vol) in batches for pulping for 1 hour. The system was filtered, and a filter cake was eluted with isopropanol (2760.0 ml, 0.5 vol). The filter cake was transferred to a vacuum drying oven to be dried under a nitrogen cylinder pressure at 60° C. for 16 hours, and then transferred to the vacuum drying oven again to be dried at 100° C. for 24 hours. After drying, a total of 4.52 kg of product was obtained with a yield of 72.8%, which was a white powdery solid, that was, the PNAC.

Contents of main ingredients of the polypeptide derivative tablet containing the fatty acid side chain were as shown in Table 13:

TABLE 13

| Example of polypeptide derivative tablet prepared in the present application | | | | |
|---|---|---|---|---|
| Composition | API (polypeptide) Mass (mg/ tablet) | Delivery agent (PNAC) Mass (mg/ tablet) | Lubricant (such as magnesium stearate) Mass (mg/ tablet) | Total weight Mass (mg/ tablet) |
| 1 | 7 | 300 | 8 | 315 |

A preparation method of the polypeptide derivative tablet containing the fatty acid side chain was as follows: the polypeptide derivative and the PNAC were sieved, evenly mixed with excipients and directly tabletted.

Example 9. Study on Pharmacokinetical (PK) Characteristics of Polypeptide Derivative Tablet Containing Fatty Acid Side Chain Male Beagle dogs (9 kg to 12 kg) aged 10 months to 15 months were orally administrated with oral tablets prepared in Example 4 once a day for 5 consecutive days, and the dosages of the polypeptide derivatives (i.e. PD065, PD187 and PD183) containing the fatty acid side chains were respectively 7 mg/dog (n=5). The date of the first oral administration was recorded as Day 1, and the date of the last oral administration was recorded as Day 5. On the Day 1, whole blood of the animals before administration (~10 minutes) and at the 2nd hour, the 4th hour and the 8th hour after administration was collected and plasma was prepared (with heparin sodium serving as an anticoagulant); on the Day 2 to the Day 4, whole blood of the animals before administration (~10 minutes) and at the 2nd hour and the 4th hour after administration was collected and plasma was prepared (with heparin sodium serving as an anticoagulant); and on the Day 5, whole blood of the animals before administration (~10 minutes) and at the $2^{nd}$ hour, the $4^{th}$ hour, the $8^{th}$ hour, $24^{th}$ hour, $48^{th}$ hour and $72^{nd}$ hour after administration was collected and plasma was prepared (with heparin sodium serving as an anticoagulant). The plasma was stored at −80° C. and used for subsequent analysis. A drug content in the plasma was analyzed by LC-MS/MS (Waters ACQUITY I Class Premier UPLC tandem with Sciex 6500+QQQ). Experimental data were drawn by GraphPad Prism9.3.1. After the three polypeptide derivative tablets were administrated respectively, results of plasma concentrations of the three polypeptide derivatives (i.e. PD065, PD187 and PD183) measured at the time points respectively were as shown in FIG. 6.

Charge-to-mass ratio was a ratio of a charge of charged particles to a mass of the charged particles. A charge-to-mass ratio of ion pairs used in the PD065 was 1102.9/1074.5, a charge-to-mass ratio of ion pairs used in the PD187 was 1153/1120.9, and a charge-to-mass ratio of ion pairs used in the PD183 was 945.6/919.8.

Figure 6:
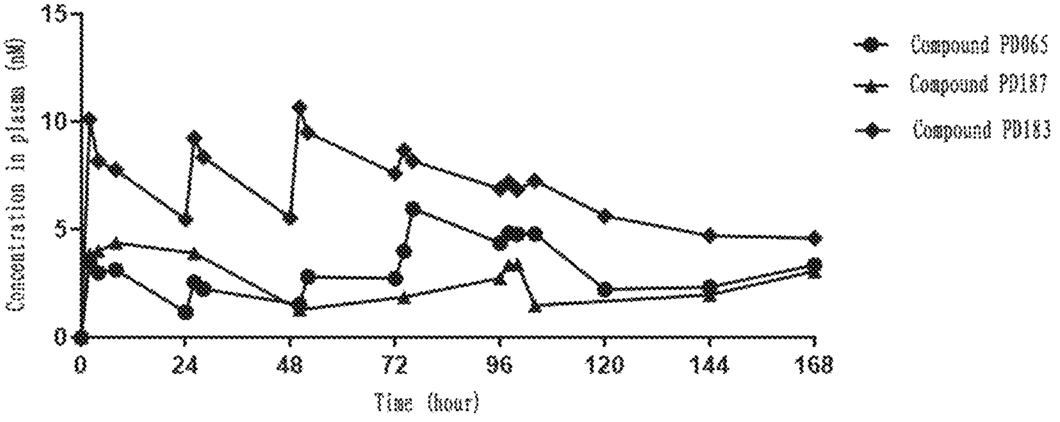
FIG. 6 shows pharmacokinetics of various polypeptides after Beagle dogs are orally administered with orally delivered compositions respectively containing different polypeptide derivatives.

It could be seen from the results as shown in FIG. 6 that: although the compounds PD187 and PD183 both had better weight reduction effect, in the same delivery environment, compared with the compound PD065-contained tablet group, the oral availability was not improved; and surprisingly, the compound PD183 molecule showed a special synergistic effect in the tablets of the PNAC, showing a very high oral bioavailability.

Although the examples of the present disclosure are described above, the present disclosure is not limited to the above specific examples and application fields, and the above specific examples are only illustrative and instructive, and are not restrictive. Under the inspiration of the specification, those of ordinary skills in the art may also make many forms without departing from the scope of protection of the claims of the present disclosure, all of which belong to the protection of the present disclosure.

What is claimed is:

1. An amylin polypeptide analog or a derivative thereof, comprising the amino acid sequence: KCNTATCATQ RLADFLRHSS NNLKPILPPT NVGSNT-trans-Hyp-$NH_2$ (SEQ ID NO: 101).

2. The amylin polypeptide analog of claim 1, wherein the amylin polypeptide analog consists of the amino acid sequence: KCNTATCATQ RLADFLRHSS NNLKPILPPT NVGSNT-trans-Hyp-$NH_2$ (SEQ ID NO: 101).

3. The amylin polypeptide analog of claim 1, further comprising a fatty acid side chain.

4. A pharmaceutical composition, comprising the amylin polypeptide analog or the derivative thereof according to claim 1 and an oral delivery agent.

5. The pharmaceutical composition of claim 4, wherein the oral delivery agent comprises N-[8-(2-hydroxybenzoyl)amino]octanoic acid (NAC) salt

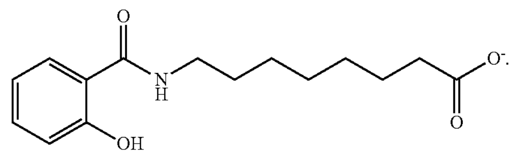

6. The pharmaceutical composition of claim 4, wherein the oral delivery agent comprises potassium N-[8-(2-hydroxybenzoyl)amino]octanoate

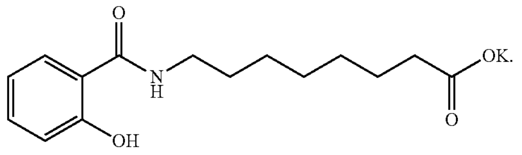

7. The pharmaceutical composition of claim 4, further comprising one or more pharmacologically active substances.

* * * * *